United States Patent
Lira et al.

(10) Patent No.: US 9,062,284 B2
(45) Date of Patent: *Jun. 23, 2015

(54) USES AND DETECTION OF HERBICIDE RESISTANCE GENES FOR RESISTANCE TO ARYLOXYALKANOATE HERBICIDES

(71) Applicant: Dow ArgoSciences LLC, Indianapolis, IN (US)

(72) Inventors: Justin M. Lira, Zionsville, IN (US); Erika Snodderley, Avon, IN (US); Andrew E. Robinson, Brownsburg, IN (US); Terry R. Wright, Carmel, IN (US); Donald Merlo, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 195 days.

This patent is subject to a terminal disclaimer.

(21) Appl. No.: 13/633,515

(22) Filed: Oct. 2, 2012

(65) Prior Publication Data

US 2013/0040815 A1    Feb. 14, 2013

Related U.S. Application Data

(63) Continuation of application No. 12/599,385, filed as application No. PCT/US2008/063212 on May 9, 2008, now Pat. No. 8,278,505.

(60) Provisional application No. 60/928,303, filed on May 9, 2007.

(51) Int. Cl.
*A01H 5/00* (2006.01)
*C12N 9/02* (2006.01)
*C12N 15/82* (2006.01)

(52) U.S. Cl.
CPC .......... *C12N 9/0004* (2013.01); *C12N 15/8274* (2013.01); *C12N 15/8275* (2013.01)

(58) Field of Classification Search
CPC ........... C12N 15/8274; C12N 15/8275; C12Y 113/11; C12Q 1/26; C12Q 1/00; C12Q 2521/00; C12Q 2561/00; C07K 14/195
See application file for complete search history.

(56) References Cited

U.S. PATENT DOCUMENTS

| 6,376,754 B1 | 4/2002 | Schillinger et al. |
| 7,105,724 B2 | 9/2006 | Weeks et al. |
| 7,316,990 B2 | 1/2008 | Tank et al. |
| 8,278,505 B2 * | 10/2012 | Lira et al. ............ 800/278 |

FOREIGN PATENT DOCUMENTS

| WO | WO 2005/107437 A2 | 11/2005 |
| WO | WO 2007/053482 A2 | 5/2007 |

OTHER PUBLICATIONS

Database GenEmbl, Accession No. DQ406818, Mar. 14, 2006.
Muller, et al., Genetic Analysis of Phenoxyalkanoic Acid Degradation in *Sphingomonas herbicidovorans* MH, Applied and Environmental Microbiology, Oct. 2004, p. 6066-6075, Abstract, p. 6071, Table 1, EMBL accession No. AJ628860.
Koehler, GenBank Submission Q700X4_9SPHN, Jul. 5, 2004, [Retrieved from the Internet on Nov. 11, 2008: <URL:http://www.expasy.org/uniprot/Q700X4_9SPHN>].
Koehler, *Sphingomonas herbicidovarans* MH: A versatile phenoxyalkanoic acid herbicide degrader, Journal of Industrial Microbiology and Biotechnology, vol. 23, No. 4-5, Oct. 1999, pp. 336-340, XP002587234.
Schleinitz, Localization and characterization of two novel genes encoding stereospecific dioxygenases catalyzing 2(2,4-dichlorophenoxy) propion ate cleavage in *Delftia acidovorans* MC1, Applied and Environmental Microbiology, American Society for Microbiology, vol. 70, No. 9, Sep. 1, 2004, pp. 5357-5365, XP002549093.
Gollop, et al., Regulation of the leucoanthocyanidin diosygenase gene expression in *Vitis vinifera*, Plant Science, 2001, 161(3); 579-588.

* cited by examiner

*Primary Examiner* — Eileen B O Hara
(74) *Attorney, Agent, or Firm* — James Daly, IV; Faegre Baker Daniels LLP

(57) ABSTRACT

The subject invention provides novel plants that are not only resistant to 2,4-D, but also to a pyridyloxyacetate herbicide. The subject invention also includes plants that produce one or more enzymes of the subject invention "stacked" together with one or more other herbicide resistance genes. The subject invention enables novel combinations of herbicides to be used in new ways. Furthermore, the subject invention provides novel methods of preventing the development of, and controlling, strains of weeds that are resistant to one or more herbicides such as glyphosate. The preferred enzyme and gene for use according to the subject invention are referred to herein as AAD-13 (AryloxyAlkanoate Dioxygenase). This highly novel discovery is the basis of significant herbicide tolerant crop trait and selectable marker opportunities.

12 Claims, 3 Drawing Sheets

■Addition of O₂ is *stereospecific*
■Breakdown of intermediate to phenol + glyoxylate is spontaneous

```
                10        20        30        40        50        60
       ....|....|....|....|....|....|....|....|....|....|....|....|
aad 13   1 ----------MSPAFDIAPLDATFGAVVTGVKLAD-LDDAGWLDLQAAWLEYALLVFPDQ
aad 12   1 ----------MQTTLQITPTGATLGATVTGVHLAT-LDDAGFAALHAAWLQHALLIFPGQ
aad  1   1 MHAALSPLSQRFERIAVQPLTGVLGAEITGVDLREPLDDSTWNEILDAFHTYQVIYFPGQ
aad  2   1 ------------MTIAIRQLQTHFVGQVSGLDLRKPLTPGEAREVESAMDKYAVLVFHDQ
tfdA     1 ------------MSVVANPLHPLFAAGVEDIDLREALGSTEVREIERLMDEKSVLVFRGQ
tauD     1 ----------MSERLSITPLGPYIGAQISGADLTRPLSDNQFEQLYHAVLRHQVYFLRDQ 70        80        90       100       110       120
       ....|....|....|....|....|....|....|....|....|....|....|....|
aad 13  50 HLTREQQIAFARRFGPLE----------------FEMAAISNVRPDGSLRVES--DNDD
aad 12  50 HLSNDQQITFAKRFGAIER------------IGGGDIVAISNVKADGTVRQHSPAEWDD
aad  1  61 AITNEQHIAFSRRFGPVDP--------------VPLLKSIEGYPEVQMIRREA------
aad  2  49 DITDEQQMAFALNFGQREDARGGTVTKEKDYRLQ-SGLNDVSNLGKDGKPLAKD----SR
tfdA    49 PLSQDQQIAFARNFGPLEG--GFIKVNQRPSRFKYAELADISNVSLDGKVAQRD----AR
tauD    51 AITPQQQRALAQRFGELHI--------------HPVYPHAEGVDEIIVLDTHN------

130       140       150       160       170       180
       ....|....|....|....|....|....|....|....|....|....|....|....|
aad 13  91 MMKILKGNMGWHADSTYMPVQAKGAVFSAEVVPSVGGQTGFADMRAAYDALDEDLKARVE
aad 12  97 MMKVIVGNMAWHADSTYMPVMAQGAVFSAEVVPAVGGRTCFADMRAAYDALDEATRALVH
aad  1 100 NESGRVIGDDWHTDSTFLDAPPAAVVMRAIDVPEHGGDTGFLSMYTAWETLSPTMQATIE
aad  2 104 THLFNLGNCLWHSDSSFRPIPAKFSLLSARVVNPTGGNTEFADMRAAYDALDDETKAEIE
tfdA   103 EVVGNFANQLWHSDSSFQQPAARYSMLSAVVVPPSGGDTEFCDMRAAYDALPRDLQSELE
tauD    90 DNPP--DNDNWHTDVTFIETPPAGAILAAKELPSTGGDTLWTSGIAAYEALSVPFRQLLS 190       200       210       220       230       240
       ....|....|....|....|....|....|....|....|....|....|....|....|
aad 13 151 TLQARHSLHYSQS---KLGHQTKAADGEYSGYGLHDGPVPLRPLVKIHPETGRKSLLIGR
aad 12 157 QRSARHSLVYSQS---KLGHVQQAGS-AYIGYGMDTTATPLRPLVKVHPETGRPSLLIGR
aad  1 160 GLNVVHSATRVFGSLYQAQNRRFSNTSVKVMDVDAGDRETVHPLVVTHPGSGRKGLYVNQ
aad  2 164 DLVCEHSLMYSRG---SLGFT------EYTDEEKQMFKPVLQRLVRTHPVHRRKSLYLSS
tfdA   163 GLRAEHYALNSRF---LLGDT------DYSEAQRNAMPPVNWPLVRTHAGSGRKFLFIGA
tauD   148 GLRAEHDFRKSFP---EYKYRKTEEEHQRWREAVAKNPPLLHPVVRTHPVSGKQALFVNE 250       260       270       280       290       300
       ....|....|....|....|....|....|....|....|....|....|....|....|
aad 13 207 -HAHAIPGLEPAESERLLQQLIDFACQPPRIYHHDWAPGDAVLWDNRCLLHQATPWDMTQ
aad 12 212 -HAHAIPGMDAAESERFLEGLVDWACQAPRVHAHQWAAGDVVVWDNRCLLHRAEPWDFKL
aad  1 220 VYCQRIEGMTDAESKPLLQFLYEHATRFDFTCRVRWKKDQVLVWDNLCTMHRAVPDYAGK
aad  2 214 -HAGKIASMSVPEGRLLLRDLNEHATQPEFVYVHKWKLHDLVMWDNRQTMHRVRRYDQSQ
tfdA   213 -HASHVEGLPVAEGRMLLAELLEHATQREFVYRHRWNVGDLVMWDNRCVLHRGRRYDISA
tauD   205 GFTTRIVDVSEKESEALLSFLFAHITKPEFQVRWRWQPNDIAIWDNRVTQHYANADYLPQ 310       320
       ....|....|....|....|..
aad 13 267 KRIMWHSRIAGDPASETALAH-
aad 12 272 PRVMWHSRLAGRPETEGAALV-
aad  1 280 FRYLTRTTVGGVRPAR------
aad  2 274 PRDMRRATVAGTEPTVQQQAAE
tfdA   273 RRELRRATTLDDAVV-------
tauD   265 RRIMHRATILGDKPFYRAG---
```

FIGURE 2

USES AND DETECTION OF HERBICIDE RESISTANCE GENES FOR RESISTANCE TO ARYLOXYALKANOATE HERBICIDES

CROSS-REFERENCE TO RELATED APPLICATION

This application is a continuation of U.S. patent application Ser. No. 12/599,385, filed Nov. 9, 2009, issued Oct. 2, 2012 as U.S. Pat. No. 8,278,505, which claims the benefit of PCT International Application Serial No. PCT/US2008/63212, filed May 9, 2008, which claims the benefit of U.S. Provisional Application Ser. No. 60/928,303, filed May 9, 2007, the disclosures each of which are expressly incorporated herein by reference.

BACKGROUND OF THE INVENTION

Weeds can quickly deplete soil of valuable nutrients needed by crops and other desirable plants. There are many different types of herbicides presently used for the control of weeds. One extremely popular herbicide is glyphosate.

Crops, such as corn, soybeans, canola, cotton, sugar beets, wheat, turf, and rice, have been developed that are resistant to glyphosate. Thus, fields with actively growing glyphosate resistant soybeans, for example, can be sprayed to control weeds without significantly damaging the soybean plants.

With the introduction of genetically engineered, glyphosate tolerant crops (GTCs) in the mid-1990's, growers were enabled with a simple, convenient, flexible, and inexpensive tool for controlling a wide spectrum of broadleaf and grass weeds unparalleled in agriculture. Consequently, producers were quick to adopt GTCs and in many instances abandon many of the accepted best agronomic practices such as crop rotation, herbicide mode of action rotation, tank mixing, incorporation of mechanical with chemical and cultural weed control. Currently glyphosate tolerant soybean, cotton, corn, and canola are commercially available in the United States and elsewhere in the Western Hemisphere. Alfalfa was the first perennial GTC introduced, furthering the opportunity for repeated use of glyphosate on the same crop and fields repeatedly over a period of years. More GTCs (e.g., wheat, rice, sugar beets, turf, etc.) are poised for introduction pending global market acceptance. Many other glyphosate resistant species are in experimental to development stages (e.g., sugar cane, sunflower, beets, peas, carrot, cucumber, lettuce, onion, strawberry, tomato, and tobacco; forestry species like poplar and sweetgum; and horticultural species like marigold, petunia, and begonias; see "isb.vt.edu/cfdocs/fieldtests1.cfm, 2005" website). Additionally, the cost of glyphosate has dropped dramatically in recent years to the point that few conventional weed control programs can effectively compete on price and performance with glyphosate GTC systems.

Glyphosate has been used successfully in burndown and other non-crop areas for total vegetation control for more than 15 years. In many instances, as with GTCs, glyphosate has been used 1-3 times per year for 3, 5, 10, up to 15 years in a row. These circumstances have led to an over-reliance on glyphosate and GTC technology and have placed a heavy selection pressure on native weed species for plants that are naturally more tolerant to glyphosate or which have developed a mechanism to resist glyphosate's herbicidal activity.

Extensive use of glyphosate-only weed control programs is resulting in the selection of glyphosate-resistant weeds, and is selecting for the propagation of weed species that are inherently more tolerant to glyphosate than most target species (i.e., weed shifts). (Powles and Preston, 2006, Ng et al., 2003; Simarmata et al., 2003; Lorraine-Colwill et al., 2003; Sfiligoj, 2004; Miller et al., 2003; Heap, 2005; Murphy et al., 2002; Martin et al., 2002.) Although glyphosate has been widely used globally for more than 15 years, only a handful of weeds have been reported to have developed resistance to glyphosate (Heap, 2005); however, most of these have been identified in the past five years. Resistant weeds include both grass and broadleaf species—*Lolium rigidum, Lolium multiflorum, Eleusine indica, Sorghum halepense, Ambrosia artemisiifolia, Conyza canadensis, Conyza bonariensis, Plantago lanceolata, Amaranthus palmerii*, and *Amaranthus rudis*. Additionally, weeds that had previously not been an agronomic problem prior to the wide use of GTCs are now becoming more prevalent and difficult to control in the context of GTCs, which comprise >80% of U.S. cotton and soybean acres and >20% of U.S. corn acres (Gianessi, 2005). These weed shifts are occurring predominantly with (but not exclusively) difficult-to-control broadleaf weeds. Some examples include *Ipomoea, Amaranthus, Chenopodium, Taraxacum*, and *Commelina* species.

In areas where growers are faced with glyphosate resistant weeds or a shift to more difficult-to-control weed species, growers can compensate for glyphosate's weaknesses by tank mixing or alternating with other herbicides that will control the missed weeds. One popular and efficacious tankmix partner for controlling broadleaf escapes in many instances has been 2,4-dichlorophenoxyacetic acid (2,4-D). 2,4-D has been used agronomically and in non-crop situations for broad spectrum, broadleaf weed control for more than 60 years. Individual cases of more tolerant species have been reported, but 2,4-D remains one of the most widely used herbicides globally. A limitation to further use of 2,4-D is that its selectivity in dicot crops like soybean or cotton is very poor, and hence 2,4-D is not typically used on (and generally not near) sensitive dicot crops. Additionally, 2,4-D's use in grass crops is somewhat limited by the nature of crop injury that can occur. 2,4-D in combination with glyphosate has been used to provide a more robust burndown treatment prior to planting no-till soybeans and cotton; however, due to these dicot species' sensitivity to 2,4-D, these burndown treatments must occur at least 14-30 days prior to planting (Agriliance, 2005).

2,4-D is in the phenoxy acid class of herbicides, as is MCPA. 2,4-D has been used in many monocot crops (such as corn, wheat, and rice) for the selective control of broadleaf weeds without severely damaging the desired crop plants. 2,4-D is a synthetic auxin derivative that acts to deregulate normal cell-hormone homeostasis and impede balanced, controlled growth; however, the exact mode of action is still not known. Triclopyr and fluoroxypyr are pyridyloxyacetic acid herbicides whose mode of action is as a synthetic auxin, also.

These herbicides have different levels of selectivity on certain plants (e.g., dicots are more sensitive than grasses). Differential metabolism by different plants is one explanation for varying levels of selectivity. In general, plants metabolize 2,4-D slowly, so varying plant response to 2,4-D may be more likely explained by different activity at the target site(s) (WSSA, 2002). Plant metabolism of 2,4-D typically occurs via a two-phase mechanism, typically hydroxylation followed by conjugation with amino acids or glucose (WSSA, 2002).

Over time, microbial populations have developed an alternative and efficient pathway for degradation of this particular xenobiotic, which results in the complete mineralization of 2,4-D. Successive applications of the herbicide select for microbes that can utilize the herbicide as a carbon source for growth, giving them a competitive advantage in the soil. For this reason, 2,4-D currently formulated has a relatively short soil half-life, and no significant carryover effects to subsequent crops are encountered. This adds to the herbicidal utility of 2,4-D.

One organism that has been extensively researched for its ability to degrade 2,4-D is *Ralstonia eutropha* (Streber et al., 1987). The gene that codes for the first enzymatic step in the mineralization pathway is tfdA. See U.S. Pat. No. 6,153,401 and GENBANK Acc. No. M16730. TfdA catalyzes the conversion of 2,4-D acid to dichlorophenol (DCP) via an α-ketoglutarate-dependent dioxygenase reaction (Smejkal et al., 2001). DCP has little herbicidal activity compared to 2,4-D. TfdA has been used in transgenic plants to impart 2,4-D resistance in dicot plants (e.g., cotton and tobacco) normally sensitive to 2,4-D (Streber et al. (1989), Lyon et al. (1989), Lyon (1993), and U.S. Pat. No. 5,608,147).

A large number of tfdA-type genes that encode proteins capable of degrading 2,4-D have been identified from the environment and deposited into the Genbank database. Many homologues are similar to tfdA (>85% amino acid identity) and have similar enzymatic properties to tfdA. However, there are a number of homologues that have a significantly lower identity to tfdA (25-50%), yet have the characteristic residues associated with α-ketoglutarate dioxygenase $Fe^{+2}$ dioxygenases. It is therefore not obvious what the substrate specificities of these divergent dioxygenases are.

One unique example with low homology to tfdA (35% amino acid identity) is sdpA from *Sphingobium herbicidovorans* (Kohler et al., 1999, Westendorf et al., 2002, Westendorf et al., 2003). This enzyme has been shown to catalyze the first step in (S)-dichlorprop (and other (S)-phenoxypropionic acids) as well as 2,4-D (a phenoxyacetic acid) mineralization (Westendorf et al., 2003). Transformation of this gene into plants has not heretofore been reported.

Development of new herbicide-tolerant crop (HTC) technologies has been limited in success due largely to the efficacy, low cost, and convenience of GTCs. Consequently, a very high rate of adoption for GTCs has occurred among producers. This created little incentive for developing new HTC technologies.

Aryloxyalkanoate chemical substructures are a common entity of many commercialized herbicides including the phenoxyacetate auxins (such as 2,4-D and dichlorprop), pyridyloxyacetate auxins (such as fluoroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac). However, these classes of herbicides are all quite distinct, and no evidence exists in the current literature for common degradation pathways among these chemical classes. A multifunctional enzyme for the degradation of herbicides covering multiple modes of action has recently been described (PCT US/2005/014737; filed May 2, 2005). Another unique multifunctional enzyme and potential uses are described hereafter.

BRIEF SUMMARY OF THE INVENTION

The subject invention provides novel plants that are not only resistant to 2,4-D, but also to pyridyloxyacetate herbicides. Heretofore, there was no expectation or suggestion that a plant with both of these advantageous properties could be produced by the introduction of a single gene. The subject invention also includes plants that produce one or more enzymes of the subject invention "stacked" together with one or more other herbicide resistance genes, including, but not limited to, glyphosate-, ALS- (imidazolinone, sulfonylurea), aryloxyalkanoate-, HPPD-, PPO-, and glufosinate-resistance genes, so as to provide herbicide-tolerant plants compatible with broader and more robust weed control and herbicide resistance management options. The present invention further includes methods and compositions utilizing homologues of the genes and proteins exemplified herein.

In some embodiments, the invention provides monocot and dicot plants tolerant to 2,4-D, MCPA fluoroxypyr, and one or more commercially available herbicides (e.g., glyphosate, glufosinate, paraquat, ALS-inhibitors (e.g., sulfonylureas, imidazolinones, triazolopyrimidine sulfonanilides, et al), HPPD inhibitors (e.g, mesotrione, isoxaflutole, et al.), dicamba, bromoxynil, aryloxyphenoxypropionates, and others). Vectors comprising nucleic acid sequences responsible for such herbicide tolerance are also disclosed, as are methods of using such tolerant plants and combinations of herbicides for weed control and prevention of weed population shifts. The subject invention enables novel combinations of herbicides to be used in new ways. Furthermore, the subject invention provides novel methods of preventing the development of, and controlling, strains of weeds that are resistant to one or more herbicides such as glyphosate. The subject invention enables novel uses of novel combinations of herbicides and crops, including preplant application to an area to be planted immediately prior to planting with seed for plants that would otherwise be sensitive to that herbicide (such as 2,4-D).

The subject invention relates in part to the identification of an enzyme that is not only able to degrade 2,4-D, but also surprisingly possesses novel properties, which distinguish the enzyme of the subject invention from previously known tfdA-type proteins, for example. More specifically, the subject invention relates to the use of an enzyme that is capable of degrading both 2,4-D and pyridyloxyacetate herbicides. No α-ketoglutarate-dependent dioxygenase enzyme has previously been reported to have the ability to degrade herbicides of both the phenoxyacetate and pyridyloxyacetates auxin herbicides. The preferred enzyme and gene for use according to the subject invention are referred to herein as AAD-13 (AryloxyAlkanoate Dioxygenase). This highly novel discovery is the basis of significant herbicide-tolerant crop (HTC) trait and selectable marker opportunities. Plants of the subject invention can be resistant throughout their entire life cycle.

There was no prior motivation to produce plants comprising an AAD-13 gene (preferably an AAD-13 polynucleotide that has a sequence optimized for expression in one or more types of plants, as exemplified herein), and there was no expectation that such plants could effectively produce an AAD-13 enzyme to render the plants resistant a phenoxyacetic acid herbicide (such as 2,4-D) and/or one or more pyridyloxyacetates herbicides such as triclopyr and fluoroxypyr. Thus, the subject invention provides many advantages that were not heretofore thought to be possible in the art.

This invention also relates in part to the identification and use of genes encoding aryloxyalkanoate dioxygenase enzymes that are capable of degrading phenoxyacetate auxin and/or pyridyloxyacetates auxin herbicides. Methods of screening proteins for these activities are within the scope of the subject invention. Thus, the subject invention includes degradation of 2,4-dichlorophenoxyacetic acid and other aryloxyalkanoate auxin herbicides by a recombinantly expressed AAD-13 enzyme. The subject invention also includes methods of controlling weeds wherein said methods comprise applying one or more pyridyloxyacetate or phenoxyacetate auxin herbicides to plants comprising an AAD-13 gene. The subject invention also provides methods of using an AAD-13 gene as a selectable marker for identifying plant cells and whole plants transformed with AAD-13, optionally including one, two, or more exogenous genes simultaneously inserted into target plant cells. Methods of the subject invention include selecting transformed cells that are resistant to appropriate levels of an herbicide. The subject invention further includes methods of preparing a polypeptide, having the biological activity of aryloxyalkanoate dioxygenase, by culturing plants and/or cells of the subject invention.

BRIEF DESCRIPTION OF THE FIGURES

FIG. 2 is a ClustalW alignment of a-ketoglutarate dioxygenases. Residues conserved in 80% of the sequences are highlighted. (Identical and similar residues are highlighted.) SEQ ID NO:2 provides the sequence of the aad 13 sequence in FIG. 2. SEQ ID NO:12 provides the sequence of the aad 12 sequence in FIG. 2. SEQ ID NO:13 provides the sequence of the aad 1 sequence in FIG. 2. SEQ ID NO:14 provides the sequence of the aad 2 sequence in FIG. 2. SEQ ID NO:15 provides the sequence of the tfdA sequence in FIG. 2. SEQ ID NO:16 provides the sequence of the tauD sequence in FIG. 2.

BRIEF DESCRIPTION OF THE SEQUENCES

SEQ ID NO:1 is the native nucleotide sequence of AAD-13 from *Sphingobium herbicidovorans*.

SEQ ID NO:2 is the translated protein sequence encoded by SEQ ID NO:1. SEQ ID NO:3 is the plant optimized nucleotide sequence of AAD-13 (v1).

SEQ ID NO:4 is the translated protein sequence encoded by SEQ ID NO:3.

SEQ ID NO:5 is the *E. coli* optimized nucleotide sequence of AAD-13 (v2).

SEQ ID NO:6 shows the sequence of the "sdpacodF" AAD-13 (v1) primer.

SEQ ID NO:7 shows the sequence of the "sdpacodR" AAD-13 (v1) primer.

SEQ ID NO:8 shows the sequence of the "sucCD" primer.
SEQ ID NO:9 shows the sequence of the "sucCD" primer.
SEQ ID NO:10 shows the sequence of the AAD-13 (v2) primer.
SEQ ID NO:11 shows the sequence of the AAD-13 (v2) primer.
SEQ ID NO:12 shows the sequence of aad 12 as in FIG. 2.
SEQ ID NO:13 shows the sequence of aad 1 as in FIG. 2.
SEQ ID NO:14 shows the sequence of aad 2 as in FIG. 2.
SEQ ID NO:15 shows the sequence of tfdA as in FIG. 2.
SEQ ID NO:16 shows the sequence of tauD as in FIG. 2.

DETAILED DESCRIPTION OF THE INVENTION

Figure 1:
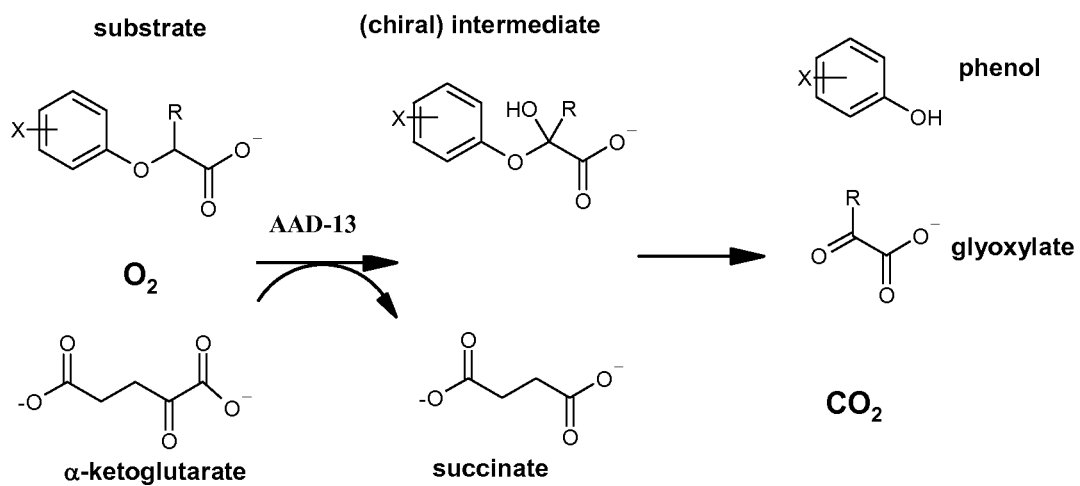
FIG. 1 illustrates the general chemical reaction that is catalyzed by AAD-13 enzymes of the subject invention.

The subject development of a 2,4-D resistance gene and subsequent resistant crops provides excellent options for controlling broadleaf, glyphosate-resistant (or highly tolerant and shifted) weed species for in-crop applications. 2,4-D is a broad-spectrum, relatively inexpensive, and robust broadleaf herbicide that would provide excellent utility for growers if greater crop tolerance could be provided in dicot and monocot crops alike. 2,4-D-tolerant transgenic dicot crops would also have greater flexibility in the timing and rate of application. An additional utility of the subject herbicide tolerance trait for 2,4-D is its utility to prevent damage to normally sensitive crops from 2,4-D drift, volatilization, inversion (or other off-site movement phenomenon), misapplication, vandalism, and the like. An additional benefit of the AAD-13 gene is that unlike all tfdA homologues characterized to date, AAD-13 is able to degrade the pyridyloxyacetates auxin (e.g., fluoroxypyr) in addition to achiral phenoxy auxins (e.g., 2,4-D, MCPA, 4-chlorophenoxyacetic acid). See Table 1. A general illustration of the chemical reactions catalyzed by the subject AAD-13 enzyme is shown in FIG. 1. (Addition of $O_2$ is stereospecific; breakdown of intermediate to phenol and glyoxylate is spontaneous.) It should be understood that the chemical structures in FIG. 1 illustrate the molecular backbones and that various R groups and the like (such as those shown in Table 1) are included but are not necessarily specifically illustrated in FIG. 1. Multiple mixes of different phenoxy auxin combinations have been used globally to address specific weed spectra and environmental conditions in various regions. Use of the AAD-13 gene in plants affords protection to a much wider spectrum of auxin herbicides, thereby increasing the flexibility and spectra of weeds that can be controlled. The subject invention can also be used to protect from drift or other off-site synthetic auxin herbicide injury for the full breadth of commercially available phenoxy auxins. Table 1 defines commercially available pyridyloxy and phenoxy auxins and provides relevant chemical structures.

TABLE 1

Commercially available phenoxyacetate and pyridyloxyacetate auxins.

| Chemical name | CAS no | Possible use rate ranges (g ae/ha) | Preferred use rate ranges (g ae/ha) | Structure |
| --- | --- | --- | --- | --- |
| 2,4-D | 94-75-7 | 25-4000 | 280-1120 | 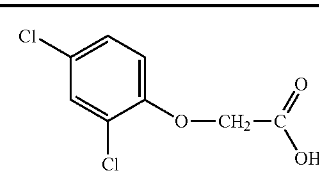 |

TABLE 1-continued

Commercially available phenoxyacetate and pyridyloxyacetate auxins.

| Chemical name | CAS no | Possible use rate ranges (g ae/ha) | Preferred use rate ranges (g ae/ha) | Structure |
|---|---|---|---|---|
| 2,4,5-T | 93-76-5 | 25-4000 | 25-4000 | 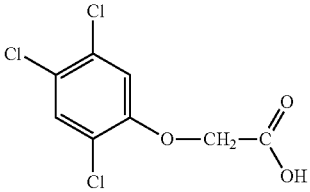 [SMILES: O=C(O)COc1cc(Cl)c(Cl)cc1Cl] |
| 4-CPA | 122-88-3 | 25-4000 | 25-4000 | 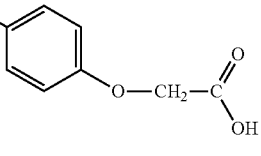 |
| 3,4-DA | 588-22-7 | 25-4000 | 25-4000 | 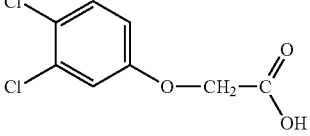 |
| MCPA | 94-74-6 | 25-4000 | 125-1550 | 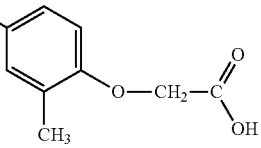 |
| Triclopyr | 55335-06-3 | 50-2000 | 70-840 | 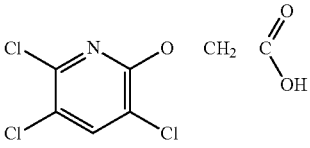 |
| Fluroxypyr | 69377-81-7 | 25-2000 | 35-560 | 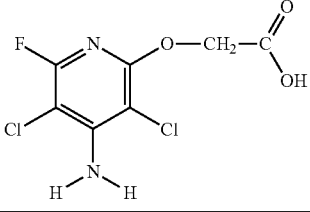 |

Reference to phenoxy auxin and pyridyloxy auxin herbicides is generally made to the active acid but some are commercially formulated as any of a variety of corresponding ester formulations and these are likewise considered as substrates for AAD-13 enzyme in planta as general plant esterases convert these esters to the active acids in planta. Likewise reference can also be for the corresponding organic or inorganic salt of the corresponding acid. Possible use rate ranges can be as stand-alone treatments or in combination with other herbicides in both crop and non-crop uses.

A single gene (AAD-13) has now been identified which, when genetically engineered for expression in plants, has the properties to allow the use of phenoxy auxin herbicides in plants where inherent tolerance never existed or was not sufficiently high to allow use of these herbicides. Additionally, AAD-13 can provide protection in planta to pyridyloxyacetate herbicides where natural tolerance also was not sufficient to allow selectivity, expanding the potential utility of these herbicides. Plants containing AAD-13 alone now may be treated sequentially or tank mixed with one, two, or a combination of several phenoxy auxin herbicides. The rate for each phenoxy auxin herbicide may range from 25 to 4000 g ae/ha, and more typically from 100 to 2000 g ae/ha for the control of a broad spectrum of dicot weeds. Likewise, one, two, or a mixture of several pyridyloxyacetate auxin compounds may be applied to plants expressing AAD-13 with reduced risk of injury from said herbicides. The rate for each pyridyloxyacetate herbicide may range from 25 to 2000 g ae/ha, and more typically from 35-840 g ae/ha for the control of additional dicot weeds.

Glyphosate is used extensively because it controls a very wide spectrum of broadleaf and grass weed species. However, repeated use of glyphosate in GTCs and in non-crop applications has, and will continue to, select for weed shifts to naturally more tolerant species or glyphosate-resistant biotypes. Tankmix herbicide partners used at efficacious rates that offer control of the same species but having different modes of action is prescribed by most herbicide resistance management strategies as a method to delay the appearance of resistant weeds. Stacking AAD-13 with a glyphosate tolerance trait (and/or with other herbicide-tolerance traits) could provide a mechanism to allow for the control of glyphosate resistant dicot weed species in GTCs by enabling the use of glyphosate, phenoxy auxin(s) (e.g., 2,4-D) and pyridyloxyacetates auxin herbicides (e.g., fluoroxypyr)—selectively in the same crop. Applications of these herbicides could be simultaneously in a tank mixture comprising two or more herbicides of different modes of action; individual applications of single herbicide composition in sequential applications as pre-plant, preemergence, or postemergence and split timing of applications ranging from approximately 2 hours to approximately 3 months; or, alternatively, any combination of any number of herbicides representing each chemical class can be applied at any timing within about 7 months of planting the crop up to harvest of the crop (or the preharvest interval for the individual herbicide, whichever is shortest).

It is important to have flexibility in controlling a broad spectrum of grass and broadleaf weeds in terms of timing of application, rate of individual herbicides, and the ability to control difficult or resistant weeds. Glyphosate applications in a crop with a glyphosate resistance gene/AAD-13 stack could range from about 250-2500 g ae/ha; phenoxy auxin herbicide(s) (one or more) could be applied from about 25-4000 g ae/ha; and pyridyloxyacetates auxin herbicide(s) (one or more) could be applied from 25-2000 g ae/ha. The optimal combination(s) and timing of these application(s) will depend on the particular situation, species, and environment, and will be best determined by a person skilled in the art of weed control and having the benefit of the subject disclosure.

Plantlets are typically resistant throughout the entire growing cycle. Transformed plants will typically be resistant to new herbicide application at any time the gene is expressed. Tolerance is shown herein to 2,4-D across the life cycle using the constitutive promoters tested thus far (primarily CsVMV and AtUbi 10). One would typically expect this, but it is an improvement upon other non-metabolic activities where tolerance can be significantly impacted by the reduced expression of a site of action mechanism of resistance, for example. One example is Roundup Ready cotton, where the plants were tolerant if sprayed early, but if sprayed too late the glyphosate concentrated in the meristems (because it is not metabolized and is translocated); viral promoters Monsanto used are not well expressed in the flowers. The subject invention provides an improvement in these regards.

Herbicide formulations (e.g., ester, acid, or salt formulation; or soluble concentrate, emulsifiable concentrate, or soluble liquid) and tankmix additives (e.g., adjuvants, surfactants, drift retardants, or compatibility agents) can significantly affect weed control from a given herbicide or combination of one or more herbicides. Any combination of these with any of the aforementioned herbicide chemistries is within the scope of this invention.

One skilled in the art would also see the benefit of combining two or more modes of action for increasing the spectrum of weeds controlled and/or for the control of naturally more tolerant or resistant weed species. This could also extend to chemistries for which herbicide tolerance was enabled in crops through human involvement (either transgenically or non-transgenically) beyond GTCs. Indeed, traits encoding glyphosate resistance (e.g., resistant plant or bacterial EPSPS (including Agro. strain CP4), glyphosate oxidoreductase (GOX), GAT), glufosinate resistance (e.g., Pat, bar), aceto- lactate synthase (ALS)-inhibiting herbicide resistance (e.g., imidazolinone, sulfonylurea, triazolopyrimidine sulfonanilide, pyrmidinylthiobenzoates, and other chemistries=AHAS, Csr1, SurA, et al.), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes. In vivo modified EPSPS can be used in some preferred embodiments, as well as Class I, Class II, and Class III glyphosate resistance genes.

Regarding additional herbicides, some additional preferred ALS inhibitors include but are not limited to the sulfonylureas (such as chlorsulfuron, halosulfuron, nicosulfuron, sulfometuron, sulfosulfuron, trifloxysulfuron), imidazolonintones (such as imazamox, imazethapyr, imazaquin), triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some preferred HPPD inhibitors include but are not limited to mesotrione, isoxaflutole, and sulcotrione. Some preferred PPO inhibitors include but are not limited to flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Additionally, AAD-13 alone or stacked with one or more additional HTC traits can be stacked with one or more additional input (e.g., insect resistance, fungal resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

The subject invention relates in part to the identification of an enzyme that is not only able to degrade 2,4-D, but also surprisingly possesses novel properties, which distinguish the enzyme of the subject invention from previously known tfdA proteins, for example. Even though this enzyme has very low homology to tfdA, the genes of the subject invention can still be generally classified in the same overall family of α-ketoglutarate-dependent dioxygenases. This family of proteins is characterized by three conserved histidine residues in a "$HX(D/E)X_{23-26}(T/S)X_{114-183}HX_{10-13}R$" motif which comprises the active site. The histidines coordinate $Fe^{+2}$ ion in the active site that is essential for catalytic activity (Hogan et al., 2000). The preliminary in vitro expression experiments discussed herein were tailored to help select for novel attributes. These experiments also indicate the AAD-13 enzyme is unique from another disparate enzyme of the same class, disclosed in a previously filed patent application (PCT US/2005/014737; filed May 2, 2005). The AAD-1 enzyme of that application shares only about 25% sequence identity with the subject AAD-13 protein.

More specifically, the subject invention relates in part to the use of an enzyme that is not only capable of degrading 2,4-D, but also pyridyloxyacetate herbicides. No α-ketoglutarate-dependent dioxygenase enzyme, besides the previously identified AAD-1 and AAD-12 enzymes (subject of patent applications PCT US/2005/014737 (WO 2005/107437) and WO 2007/053482, respectively), has previously been reported to have the ability to degrade herbicides of different chemical classes with different modes of action. Preferred enzymes and genes for use according to the subject invention are referred to herein as AAD-13 (AryloxyAlkanoate Dioxygenase) genes and proteins.

This invention also relates in part to the identification and use of genes encoding aryloxyalkanoate dioxygenase enzymes that are capable of degrading phenoxy auxin and pyridyloxyacetate herbicides. Thus, the subject invention relates in part to the degradation of 2,4-dichlorophenoxyacetic acid, other phenoxyacetic acids, and pyridyloxyacetic acid herbicides by a recombinantly expressed AAD-13 enzyme.

The subject proteins tested positive for 2,4-D conversion to 2,4-dichlorophenol ("DCP"; herbicidally inactive) in analytical assays. Partially purified proteins of the subject invention can rapidly convert 2,4-D to DCP in vitro. An additional advantage that AAD-13 transformed plants provide is that parent herbicide(s) are metabolized to inactive forms, thereby reducing the potential for harvesting herbicidal residues in grain or stover.

The subject invention also includes methods of controlling weeds wherein said methods comprise applying a pyridyloxyacetate and/or a phenoxy auxin herbicide to plants comprising an AAD-13 gene.

In light of these discoveries, novel plants that comprise a polynucleotide encoding this type of enzyme are now provided. Heretofore, there was no motivation to produce such plants, and there was no expectation that such plants could effectively produce this enzyme to render the plants resistant to not only phenoxy acid herbicides (such as 2,4-D) but also pyridyloxyacetate herbicides. Thus, the subject invention provides many advantages that were not heretofore thought to be possible in the art.

Publicly available strains (deposited in culture collections like ATCC or DSMZ) can be acquired and screened, using techniques disclosed herein, for novel genes. Sequences disclosed herein can be used to amplify and clone the homologous genes into a recombinant expression system for further screening and testing according to the subject invention.

As discussed above in the Background section, one organism that has been extensively researched for its ability to degrade 2,4-D is *Ralstonia eutropha* (Streber et al., 1987). The gene that codes for the first enzyme in the degradation pathway is tfdA. See U.S. Pat. No. 6,153,401 and GENBANK Acc. No. M16730. TfdA catalyzes the conversion of 2,4-D acid to herbicidally inactive DCP via an α-ketoglutarate-dependent dioxygenase reaction (Smejkal et al., 2001). TfdA has been used in transgenic plants to impart 2,4-D resistance in dicot plants (e.g., cotton and tobacco) normally sensitive to 2,4-D (Streber et al., 1989; Lyon et al., 1989; Lyon et al., 1993). A large number of tfdA-type genes that encode proteins capable of degrading 2,4-D have been identified from the environment and deposited into the NCBI database. Many homologues are quite similar to tfdA (>85% amino acid identity) and have similar enzymatic properties to tfdA. However, a small collection of α-ketoglutarate-dependent dioxygenase homologues are presently identified that have a low level of homology to tfdA.

The subject invention relates in part to surprising discoveries of new uses for and functions of a distantly related enzyme, sdpA, from *Sphingobium herbicidovorans* (Westendorf et al., 2002, 2003) with low homology to tfdA (35% amino acid identity) and low homology to the recently-identified AAD-1 (27% amino acid identity). This α-ketoglutarate-dependent dioxygenase enzyme purified in its native form had previously been shown to degrade 2,4-D and S-dichlorprop (Westendorf et al., 2002 and 2003). However, no α-ketoglutarate-dependent dioxygenase enzyme has previously been reported to have the ability to degrade a selective herbicide of the pyridyloxyacetate chemical class. SdpA (from *Sphingobium herbicidovorans*) has never been expressed in plants, nor was there any motivation to do so in part because development of new HTC technologies has been limited due largely to the efficacy, low cost, and convenience of GTCs (Devine, 2005).

In light of the novel activity, proteins and genes of the subject invention are referred to herein as AAD-13 proteins and genes. AAD-13 was presently confirmed to degrade a variety of phenoxyacetate auxin herbicides in vitro. See Table 5.4.4-1 in Example 5, below. Additionally, this enzyme, as reported for the first time herein, was surprisingly found to also be capable of degrading additional substrates of the class of aryloxyalkanoate molecules. Substrates of significant agronomic importance include the pyridyloxyacetate auxin herbicides. This highly novel discovery is the basis of significant Herbicide Tolerant Crop (HTC) and selectable marker trait opportunities. This enzyme is unique in its ability to deliver herbicide degradative activity to a range of broad spectrum broadleaf herbicides (phenoxyacetate and pyridyloxyacetate auxins).

Thus, the subject invention relates in part to the degradation of 2,4-dichlorophenoxyacetic acid, other phenoxyacetic auxin herbicides, and pyridyloxyacetate herbicides by a recombinantly expressed aryloxyalkanoate dioxygenase enzyme (AAD-13). This invention also relates in part to identification and uses of genes encoding an aryloxyalkanoate dioxygenase degrading enzyme (AAD-13) capable of degrading phenoxy and/or pyridyloxy auxin herbicides.

The subject enzyme enables transgenic expression resulting in tolerance to combinations of herbicides that would control nearly all broadleaf weeds. AAD-13 can serve as an excellent herbicide tolerant crop (HTC) trait to stack with other HTC traits [e.g., glyphosate resistance, glufosinate resistance, ALS-inhibitor (e.g., imidazolinone, sulfonylurea, triazolopyrimidine sulfonanilide) resistance, bromoxynil resistance, HPPD-inhibitor resistance, PPO-inhibitor resistance, et al.], and insect resistance traits (Cry1F, Cry1Ab, Cry 34/45, other Bt. Proteins, or insecticidal proteins of a non-*Bacillis* origin, et al.) for example. Additionally, AAD-13 can serve as a selectable marker to aid in selection of primary transformants of plants genetically engineered with a second gene or group of genes.

In addition, the subject microbial gene has been redesigned such that the protein is encoded by codons having a bias toward both monocot and dicot plant usage (hemicot). *Arabidopsis*, corn, tobacco, cotton, soybean, canola, and rice have been transformed with AAD-13-containing constructs and have demonstrated high levels of resistance to both the phenoxy and pyridyloxy auxin herbicides. Thus, the subject invention also relates to "plant optimized" genes that encode proteins of the subject invention.

Oxyalkanoate groups are useful for introducing a stable acid functionality into herbicides. The acidic group can impart phloem mobility by "acid trapping," a desirable attribute for herbicide action and therefore could be incorporated into new herbicides for mobility purposes. Aspects of the subject invention also provide a mechanism of creating HTCs. There exist many potential commercial and experimental herbicides that can serve as substrates for AAD-13. Thus, the use of the subject genes can also result in herbicide tolerance to those other herbicides as well.

HTC traits of the subject invention can be used in novel combinations with other HTC traits (including but not limited to glyphosate tolerance). These combinations of traits give rise to novel methods of controlling weed (and like) species, due to the newly acquired resistance or inherent tolerance to herbicides (e.g., glyphosate). Thus, in addition to the HTC traits, novel methods for controlling weeds using herbicides, for which herbicide tolerance was created by said enzyme in transgenic crops, are within the scope of the invention.

This invention can be applied in the context of commercializing a 2,4-D resistance trait stacked with current glyphosate resistance traits in soybeans, for example. Thus, this invention provides a tool to combat broadleaf weed species shifts and/or selection of herbicide resistant broadleaf weeds, which culminates from extremely high reliance by growers on glyphosate for weed control with various crops.

The transgenic expression of the subject AAD-13 gene is exemplified in, for example, *Arabidopsis* and tobacco. Soybeans are a preferred crop for transformation according to the subject invention. However, this invention can be utilized in multiple other monocot (such as pasture grasses or turf grass) and dicot crops like alfalfa, clover, tree species, et al. Likewise, 2,4-D (or other AAD-13-substrates) can be more positively utilized in grass crops where tolerance is moderate, and increased tolerance via this trait would provide growers the opportunity to use these herbicides at more efficacious rates and over a wider application timing without the risk of crop injury.

Still further, the subject invention provides a single gene that can provide resistance to herbicides that control broadleaf weed. This gene may be utilized in multiple crops to enable the use of a broad spectrum herbicide combination. The subject invention can also control weeds resistant to current chemicals, and aids in the control of shifting weed spectra resulting from current agronomic practices. The subject AAD-13 can also be used in efforts to effectively detoxify additional herbicide substrates to non-herbicidal forms. Thus, the subject invention provides for the development of additional HTC traits and/or selectable marker technology.

Separate from, or in addition to, using the subject genes to produce HTCs, the subject genes can also be used as selectable markers for successfully selecting transformants in cell cultures, greenhouses, and in the field. There is high inherent value for the subject genes simply as a selectable marker for biotechnology projects. The promiscuity of AAD-13 for other aryloxyalkanoate auxinic herbicides provides many opportunities to utilize this gene for HTC and/or selectable marker purposes.

Proteins (and Source Isolates) of the Subject Invention.

The present invention provides functional proteins. By "functional activity" (or "active") it is meant herein that the proteins/enzymes for use according to the subject invention have the ability to degrade or diminish the activity of a herbicide (alone or in combination with other proteins). Plants producing proteins of the subject invention will preferably produce "an effective amount" of the protein so that when the plant is treated with a herbicide, the level of protein expression is sufficient to render the plant completely or partially resistant or tolerant to the herbicide (at a typical rate, unless otherwise specified; typical application rates can be found in the well-known Herbicide Handbook (Weed Science Society of America, Eighth Edition, 2002), for example). The herbicide can be applied at rates that would normally kill the target plant, at normal field use rates and concentrations. (Because of the subject invention, the level and/or concentration can optionally be higher than those that were previously used.) Preferably, plant cells and plants of the subject invention are protected against growth inhibition or injury caused by herbicide treatment. Transformed plants and plant cells of the subject invention are preferably rendered resistant or tolerant to an herbicide, as discussed herein, meaning that the transformed plant and plant cells can grow in the presence of effective amounts of one or more herbicides as discussed herein. Preferred proteins of the subject invention have catalytic activity to metabolize one or more aryloxyalkanoate compounds.

One cannot easily discuss the term "resistance" and not use the verb "tolerate" or the adjective "tolerant." The industry has spent innumerable hours debating Herbicide Tolerant Crops (HTC) versus Herbicide Resistant Crops (HRC). HTC is a preferred term in the industry. However, the official Weed Science Society of America definition of resistance is "the inherited ability of a plant to survive and reproduce following exposure to a dose of herbicide normally lethal to the wild type. In a plant, resistance may be naturally occurring or induced by such techniques as genetic engineering or selection of variants produced by tissue culture or mutagenesis." As used herein unless otherwise indicated, herbicide "resistance" is heritable and allows a plant to grow and reproduce in the presence of a typical herbicidally effective treatment by an herbicide for a given plant, as suggested by the current edition of *The Herbicide Handbook* as of the filing of the subject disclosure. As is recognized by those skilled in the art, a plant may still be considered "resistant" even though some degree of plant injury from herbicidal exposure is apparent. As used herein, the term "tolerance" is broader than the term "resistance," and includes "resistance" as defined herein, as well an improved capacity of a particular plant to withstand the various degrees of herbicidally induced injury that typically result in wild-type plants of the same genotype at the same herbicidal dose.

Transfer of the functional activity to plant or bacterial systems can involve a nucleic acid sequence, encoding the amino acid sequence for a protein of the subject invention, integrated into a protein expression vector appropriate to the host in which the vector will reside. One way to obtain a nucleic acid sequence encoding a protein with functional activity is to isolate the native genetic material from the bacterial species which produce the protein of interest, using information deduced from the protein's amino acid sequence, as disclosed herein. The native sequences can be optimized for expression in plants, for example, as discussed in more detail below. An optimized polynucleotide can also be designed based on the protein sequence.

The subject invention provides classes of proteins having novel activities as identified herein. One way to characterize these classes of proteins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining proteins for use according to the subject invention. For example, antibodies to the proteins disclosed herein can be used to identify and isolate other proteins from a mixture of proteins. Specifically, antibodies may be raised to the portions of the proteins that are most conserved or most distinct, as compared to other related proteins. These antibodies can then be used to specifically identify equivalent proteins with the characteristic activity by immunoprecipitation, enzyme linked immunosorbent assay (ELISA), or immuno-blotting. Antibodies to the proteins disclosed herein, or to equivalent proteins, or to fragments of these proteins, can be readily prepared using standard procedures. Such antibodies are an aspect of the subject invention. Antibodies of the subject invention include monoclonal and polyclonal antibodies, preferably produced in response to an exemplified or suggested protein.

One skilled in the art would readily recognize that proteins (and genes) of the subject invention can be obtained from a variety of sources. Since entire herbicide degradation operons are known to be encoded on transposable elements such as plasmids, as well as genomically integrated, proteins of the subject invention can be obtained from a wide variety of microorganisms, for example, including recombinant and/or wild-type bacteria.

Mutants of bacterial isolates can be made by procedures that are well known in the art. For example, asporogenous mutants can be obtained through ethylmethane sulfonate (EMS) mutagenesis of an isolate. The mutant strains can also be made using ultraviolet light and nitrosoguanidine by procedures well known in the art.

A protein "from" or "obtainable from" any of the subject isolates referred to or suggested herein means that the protein (or a similar protein) can be obtained from the isolate or some other source, such as another bacterial strain or a plant. "Derived from" also has this connotation, and includes proteins obtainable from a given type of bacterium that are modified for expression in a plant, for example. One skilled in the art will readily recognize that, given the disclosure of a bacterial gene and protein, a plant can be engineered to produce the protein. Antibody preparations, nucleic acid probes (DNA, RNA, or PNA, for example), and the like can be prepared using the polynucleotide and/or amino acid sequences disclosed herein and used to screen and recover other related genes from other (natural) sources.

Standard molecular biology techniques may be used to clone and sequence the proteins and genes described herein. Additional information may be found in Sambrook et al., 1989, which is incorporated herein by reference.

Polynucleotides and Probes.

The subject invention further provides nucleic acid sequences that encode proteins for use according to the subject invention. The subject invention further provides methods of identifying and characterizing genes that encode proteins having the desired herbicidal activity. In one embodiment, the subject invention provides unique nucleotide sequences that are useful as hybridization probes and/or primers for PCR techniques. The primers produce characteristic gene fragments that can be used in the identification, characterization, and/or isolation of specific genes of interest. The nucleotide sequences of the subject invention encode proteins that are distinct from previously described proteins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art. The level of gene expression and temporal/tissue specific expression can greatly impact the utility of the invention. Generally, greater levels of protein expression of a degradative gene will result in faster and more complete degradation of a substrate (in this case a target herbicide). Promoters will be desired to express the target gene at high levels unless the high expression has a consequential negative impact on the health of the plant. Typically, one would wish to have the AAD-13 gene constitutively expressed in all tissues for complete protection of the plant at all growth stages. However, one could alternatively use a vegetatively expressed resistance gene; this would allow use of the target herbicide in-crop for weed control and would subsequently control sexual reproduction of the target crop by application during the flowering stage. In addition, desired levels and times of expression can also depend on the type of plant and the level of tolerance desired. Some preferred embodiments use strong constitutive promoters combined with transcription enhancers and the like to increase expression levels and to enhance tolerance to desired levels. Some such applications are discussed in more detail below, before the Examples section.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA molecules are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of genes of interest will be amplified by the procedure, thus identifying the presence of the gene(s) of interest.

Further aspects of the subject invention include genes and isolates identified using the methods and nucleotide sequences disclosed herein. The genes thus identified can encode herbicidal resistance proteins of the subject invention.

Proteins and genes for use according to the subject invention can be identified and obtained by using oligonucleotide probes, for example. These probes are detectable nucleotide sequences that can be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes) and/or other synthetic (non-natural) bases. Thus, where a synthetic, degenerate oligonucleotide is referred to herein, and "N" or "n" is used generically, "N" or "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1× SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water, adjusting pH to 7.0 with 10 N NaOH, then adjusting the volume to 1 liter. 10% SDS can be prepared by dissolving 10 g of SDS in 50 ml of autoclaved water, then diluting to 100 ml.

Detection of the probe provides a means for determining in a known manner whether hybridization has been maintained. Such a probe analysis provides a rapid method for identifying genes of the subject invention. The nucleotide segments used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein. That is, one way to define a gene (and the protein it encodes), for example, is by its ability to hybridize (under any of the conditions specifically disclosed herein) with a known or specifically exemplified gene.

As used herein, "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes can be performed by standard methods (see, e.g., Maniatis et al. 1982). In general, hybridization and subsequent washes can be carried out under conditions that allow for detection of target sequences. For double-stranded DNA gene probes, hybridization can be carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. 1983):

$$Tm=81.5° C.+16.6 \text{ Log } [Na+]+0.41(\% G+C)-0.61(\% \text{ formamide})-600/\text{length of duplex in base pairs.}$$

Washes can typically be carried out as follows:
(1) Twice at room temperature for 15 minutes in 1×SSPE, 0.1% SDS (low stringency wash).
(2) Once at Tm-20° C. for 15 minutes in 0.2×SSPE, 0.1% SDS (moderate stringency wash).

For oligonucleotide probes, hybridization can be carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

$$Tm(° C.)=2(\text{number } T/A \text{ base pairs})+4(\text{number } G/C \text{ base pairs})$$

(Suggs et al., 1981).
Washes can typically be out as follows:
(1) Twice at room temperature for 15 minutes 1×SSPE, 0.1% SDS (low stringency wash).
(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:
Low: 1 or 2×SSPE, room temperature
Low: 1 or 2×SSPE, 42° C.
Moderate: 0.2× or 1×SSPE, 65° C.
High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR Technology.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are preferably oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

Exemplified DNA sequences, or segments thereof, can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of Genes and Proteins.

The subject genes and proteins can be fused to other genes and proteins to produce chimeric or fusion proteins. The genes and proteins useful according to the subject invention include not only the specifically exemplified full-length sequences, but also portions, segments and/or fragments (including contiguous fragments and internal and/or terminal deletions compared to the full-length molecules) of these sequences, variants, mutants, chimerics, and fusions thereof. Proteins of the subject invention can have substituted amino acids so long as they retain desired functional activity. "Variant" genes have nucleotide sequences that encode the same proteins or equivalent proteins having activity equivalent or similar to an exemplified protein.

The terms "variant proteins" and "equivalent proteins" refer to proteins having the same or essentially the same biological/functional activity against the target substrates and equivalent sequences as the exemplified proteins. As used herein, reference to an "equivalent" sequence refers to sequences having amino acid substitutions, deletions, additions, or insertions that improve or do not adversely affect activity to a significant extent. Fragments retaining activity are also included in this definition. Fragments and other equivalents that retain the same or similar function or activity as a corresponding fragment of an exemplified protein are within the scope of the subject invention. Changes, such as amino acid substitutions or additions, can be made for a variety of purposes, such as increasing (or decreasing) protease stability of the protein (without materially/substantially decreasing the functional activity of the protein), removing or adding a restriction site, and the like. Variations of genes may be readily constructed using standard techniques for making point mutations, for example.

In addition, U.S. Pat. No. 5,605,793, for example, describes methods for generating additional molecular diversity by using DNA reassembly after random or focused fragmentation. This can be referred to as gene "shuffling," which typically involves mixing fragments (of a desired size) of two or more different DNA molecules, followed by repeated rounds of renaturation. This can improve the activity of a protein encoded by a starting gene. The result is a chimeric protein having improved activity, altered substrate specificity, increased enzyme stability, altered stereospecificity, or other characteristics.

"Shuffling" can be designed and targeted after obtaining and examining the atomic 3D (three dimensional) coordinates and crystal structure of a protein of interest. Thus, "focused shuffling" can be directed to certain segments of a protein that are ideal for modification, such as surface-exposed segments, and preferably not internal segments that are involved with protein folding and essential 3D structural integrity.

Specific changes to the "active site" of the enzyme can be made to affect the inherent functionality with respect to activity or stereospecificity (see alignment FIG. 2) Muller et. al. (2006). The known tauD crystal structure was used as a model dioxygenase to determine active site residues while bound to its inherent substrate taurine. Elkins et al. (2002) "X-ray crystal structure of *Escherichia coli* taurine/alpha-ketoglutarate dioxygenase complexed to ferrous iron and substrates," *Biochemistry* 41(16):5185-5192. Regarding sequence optimization and designability of enzyme active sites, see Chakrabarti et al., PNAS, (Aug. 23, 2005), 102(34):12035-12040.

Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques, for example, can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, or 288 contiguous residues (amino acid or nucleotide), corresponding to a segment (of the same size) in any of the exemplified or suggested sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes that encode active fragments may be obtained using a variety of restriction enzymes. Proteases may be used to directly obtain active fragments of these proteins.

It is within the scope of the invention as disclosed herein that proteins can be truncated and still retain functional activity. By "truncated protein" it is meant that a portion of a protein may be cleaved off while the remaining truncated protein retains and exhibits the desired activity after cleavage. Cleavage can be achieved by various proteases. Furthermore, effectively cleaved proteins can be produced using molecular biology techniques wherein the DNA bases encoding said protein are removed either through digestion with restriction endonucleases or other techniques available to the skilled artisan. After truncation, said proteins can be expressed in heterologous systems such as *E. coli*, baculoviruses, plant-based viral systems, yeast, and the like and then placed in insect assays as disclosed herein to determine activity. It is well-known in the art that truncated proteins can be successfully produced so that they retain functional activity while having less than the entire, full-length sequence. For example, B.t. proteins can be used in a truncated (core protein) form (see, e.g., Höfte et al. (1989), and Adang et al. (1985)). As used herein, the term "protein" can include functionally active truncations.

In some cases, especially for expression in plants, it can be advantageous to use truncated genes that express truncated proteins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length protein.

Certain proteins of the subject invention have been specifically exemplified herein. As these proteins are merely exemplary of the proteins of the subject invention, it should be readily apparent that the subject invention comprises variant or equivalent proteins (and nucleotide sequences coding for equivalents thereof) having the same or similar activity of the exemplified proteins. Equivalent proteins will have amino acid similarity (and/or homology) with an exemplified protein. The amino acid identity will typically be at least 60%, preferably at least 75%, more preferably at least 80%, even more preferably at least 90%, and can be at least 95%. Preferred proteins of the subject invention can also be defined in terms of more particular identity and/or similarity ranges. For example, the identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein. Any number listed above can be used to define the upper and lower limits.

Unless otherwise specified, as used herein, percent sequence identity and/or similarity of two nucleic acids is determined using the algorithm of Karlin and Altschul, 1990, modified as in Karlin and Altschul 1993. Such an algorithm is incorporated into the NBLAST and XBLAST programs of Altschul et al., 1990. BLAST nucleotide searches are performed with the NBLAST program, score=100, wordlength=12. Gapped BLAST can be used as described in Altschul et al., 1997. When utilizing BLAST and Gapped BLAST programs, the default parameters of the respective programs (NBLAST and XBLAST) are used. See NCBI/NIH website. To obtain gapped alignments for comparison purposes, the AlignX function of Vector NTI Suite 8 (InforMax, Inc., North Bethesda, Md., U.S.A.), was used employing the default parameters. These were: a Gap opening penalty of 15, a Gap extension penalty of 6.66, and a Gap separation penalty range of 8.

Various properties and three-dimensional features of the protein can also be changed without adversely affecting the activity/functionality of the protein. Conservative amino acid substitutions can be tolerated/made to not adversely affect the activity and/or three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 2 provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. However, preferred substitutions do not significantly detract from the functional/biological activity of the protein.

As used herein, reference to "isolated" polynucleotides and/or "purified" proteins refers to these molecules when they are not associated with the other molecules with which they would be found in nature. Thus, reference to "isolated" and/or "purified" signifies the involvement of the "hand of man" as described herein. For example, a bacterial "gene" of the subject invention put into a plant for expression is an "isolated polynucleotide." Likewise, a protein derived from a bacterial protein and produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, proteins. These variant DNA sequences are within the scope of the subject invention. This is also discussed in more detail below in the section entitled "Optimization of sequence for expression in plants."

Optimization of Sequence for Expression in Plants.

To obtain high expression of heterologous genes in plants it is generally preferred to reengineer the genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial protein is reengineering of a heterologous gene for optimal expression, using codon bias more closely aligned with the target plant sequence, whether a dicot or monocot species. Sequences can also be optimized for expression in any of the more particular types of plants discussed elsewhere herein.

Transgenic Hosts.

The protein-encoding genes of the subject invention can be introduced into a wide variety of microbial or plant hosts. The subject invention includes transgenic plant cells and transgenic plants. Preferred plants (and plant cells) are corn, *Arabidopsis*, tobacco, soybeans, cotton, canola, rice, wheat, turf, legume forages (e.g., alfalfa and clover), pasture grasses, and the like. Other types of transgenic plants can also be made according to the subject invention, such as fruits, vegetables, ornamental plants, and trees. More generally, dicots and/or monocots can be used in various aspects of the subject invention.

In preferred embodiments, expression of the gene results, directly or indirectly, in the intracellular production (and maintenance) of the protein(s) of interest. Plants can be rendered herbicide-resistant in this manner. Such hosts can be referred to as transgenic, recombinant, transformed, and/or transfected hosts and/or cells. In some aspects of this invention (when cloning and preparing the gene of interest, for example), microbial (preferably bacterial) cells can be produced and used according to standard techniques, with the benefit of the subject disclosure.

Plant cells transfected with a polynucleotide of the subject invention can be regenerated into whole plants. The subject invention includes cell cultures including tissue cell cultures, liquid cultures, and plated cultures. Seeds produced by and/or used to generate plants of the subject invention are also included within the scope of the subject invention. Other plant tissues and parts are also included in the subject invention. The subject invention likewise includes methods of producing plants or cells comprising a polynucleotide of the subject invention. One preferred method of producing such plants is by planting a seed of the subject invention.

Although plants are preferred, the subject invention also includes production of highly active recombinant AAD-13 in a *Pseudomonas fluorescens* (Pf) host strain, for example. The subject invention includes preferred growth temperatures for maintaining soluble active AAD-13 in this host and a formulation process that can store and restore AAD-13 activity in solution; and a lyophilization process that can retain AAD-13 activity for long-term storage and shelf life.

Insertion of Genes to Form Transgenic Hosts.

One aspect of the subject invention is the transformation/transfection of plants, plant cells, and other host cells with polynucleotides of the subject invention that express proteins of the subject invention. Plants transformed in this manner can be rendered resistant to a variety of herbicides with different modes of action.

A wide variety of methods are available for introducing a gene encoding a desired protein into the target host under conditions that allow for stable maintenance and expression of the gene. These methods are well known to those skilled in the art and are described, for example, in U.S. Pat. No. 5,135,867.

Vectors comprising an AAD-13 polynucleotide are included in the scope of the subject invention. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13 mp series, pACYC184, etc. Accordingly, the sequence encoding the protein can be inserted into the vector at a suitable restriction site. The resulting plasmid is used for transformation into *E. coli*. The *E. coli* cells are cultivated in a suitable nutrient medium, then harvested and lysed. The plasmid is recovered by purification away from genomic DNA. Sequence analysis, restriction analysis, electrophoresis, and other biochemical-molecular biological methods are generally carried out as methods of analysis. After each manipulation, the DNA sequence used can be restriction digested and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985); Fraley et al. (1986); and An et al. (1985).

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), silicon carbide whiskers, aerosol beaming, PEG, or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters, 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can be cultivated advantageously with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial protein are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. Plant selectable markers also typically can provide resistance to various herbicides such as glufosinate (e.g., PAT/bar), glyphosate (EPSPS), ALS-inhibitors (e.g., imidazolinone, sulfonylurea, triazolopyrimidine sulfonanilide, et al.), bromoxynil, HPPD-inhibitor resistance, PPO-inhibitors, ACC-ase inhibitors, and many others. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a protein expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945,050 to Cornell and U.S. Pat. No. 5,141,131 to DowElanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149,645, 5,469,976, 5,464,763 and 4,940,838 and 4,693,976 to Schilperoot; European Patent Applications 116718, 290799, 320500, all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Syngenta; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca, now Syngenta. Other direct DNA delivery transformation technology includes aerosol beam technology. See U.S. Pat. No. 6,809,232. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plants can be transformed with a viral vector using the methods described in U.S. Pat. No. 5,569,597 to Mycogen Plant Science and Ciba-Geigy (now Syngenta), as well as U.S. Pat. Nos. 5,589,367 and 5,316,931, both to Biosource, now Large Scale Biology.

As mentioned previously, the manner in which the DNA construct is introduced into the plant host is not critical to this invention. Any method that provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al. (1980) and EPO 0 120 515. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the Agrobacteria are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial protein is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue that is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G41; hygromycin resistance; methotrexate resistance, as well as those genes which encode for resistance or tolerance to glyphosate; phosphinothricin (bialaphos or glufosinate); ALS-inhibiting herbicides (imidazolinones, sulfonylureas and triazolopyrimidine herbicides), ACC-ase inhibitors (e.g., ayryloxypropionates or cyclohexanediones), and others such as bromoxynil, and HPPD-inhibitors (e.g., mesotrione) and the like.

In addition to a selectable marker, it may be desirous to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in Weising et al., 1988. Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, osmotin UTR sequences, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active (or inactive) during a certain stage of the plant's development as well as active in plant tissues and organs. Examples of such include but are not limited to pollen-specific, embryo-specific, corn-silk-specific, cotton-fiber-specific, root-specific, seed-endosperm-specific, or vegetative phase-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical (tetracycline responsive), and stress. Other desirable transcription and translation elements that function in plants may be used. Numerous plant-specific gene transfer vectors are known in the art.

Plant RNA viral based systems can also be used to express bacterial protein. In so doing, the gene encoding a protein can be inserted into the coat promoter region of a suitable plant virus which will infect the host plant of interest. The protein can then be expressed thus providing protection of the plant from herbicide damage. Plant RNA viral based systems are described in U.S. Pat. No. 5,500,360 to Mycogen Plant Sciences, Inc. and U.S. Pat. Nos. 5,316,931 and 5,589,367 to Biosource, now Large Scale Biology.

Means of Further Increasing Tolerance or Resistance Levels.

It is shown herein that plants of the subject invention can be imparted with novel herbicide resistance traits without observable adverse effects on phenotype including yield. Such plants are within the scope of the subject invention. Plants exemplified and suggested herein can withstand 2×, 3×, 4×, and 5× typical application levels, for example, of at least one subject herbicide. Improvements in these tolerance levels are within the scope of this invention. For example, various techniques are know in the art, and can forseeably be optimized and further developed, for increasing expression of a given gene.

One such method includes increasing the copy number of the subject AAD-13 genes (in expression cassettes and the like). Transformation events can also be selected for those having multiple copies of the genes.

Strong promoters and enhancers can be used to "supercharge" expression. Examples of such promoters include the preferred 35T promoter which uses 35S enhancers. 35S, maize ubiquitin, *Arabidopsis* ubiquitin, A.t. actin, and CSMV promoters are included for such uses. Other strong viral promoters are also preferred. Enhancers include 4 OCS and the 35S double enhancer. Matrix attachment regions (MARs) can also be used to increase transformation efficiencies and transgene expression, for example.

Shuffling (directed evolution) and transcription factors can also be used for embodiments according to the subject invention.

Variant proteins can also be designed that differ at the sequence level but that retain the same or similar overall essential three-dimensional structure, surface charge distribution, and the like. See e.g. U.S. Pat. No. 7,058,515; Larson et al., *Protein Sci.* 2002 11: 2804-2813, "Thoroughly sampling sequence space: Large-scale protein design of structural ensembles."; Crameri et al., *Nature Biotechnology* 15, 436-438 (1997), "Molecular evolution of an arsenate detoxification pathway by DNA shuffling."; Stemmer, W. P. C. 1994. DNA shuffling by random fragmentation and reassembly: in vitro recombination for molecular evolution. Proc. Natl. Acad. Sci. USA 91: 10747-10751; Stemmer, W. P. C. 1994. Rapid evolution of a protein in vitro by DNA shuffling. Nature 370: 389-391; Stemmer, W. P. C. 1995. Searching sequence space. Bio/Technology 13: 549-553; Crameri, A., Cwirla, S, and Stemmer, W. P. C. 1996. Construction and evolution of antibody-phage libraries by DNA shuffling. Nature Medicine 2: 100-103; and Crameri, A., Whitehorn, E. A., Tate, E. and Stemmer, W. P. C. 1996. Improved green fluorescent protein by molecular evolution using DNA shuffling. Nature Biotechnology 14: 315-319.

The activity of recombinant polynucleotides inserted into plant cells can be dependent upon the influence of endogenous plant DNA adjacent the insert. Thus, another option is taking advantage of events that are known to be excellent locations in a plant genome for insertions. See e.g. WO 2005/103266 A1, relating to cry1F and cry1Ac cotton events; the subject AAD-13 gene can be substituted in those genomic loci in place of the cry1F and/or cry1Ac inserts. Thus, targeted homologous recombination, for example, can be used according to the subject invention. This type of technology is the subject of, for example, WO 03/080809 A2 and the corresponding published U.S. application (USPA 20030232410), relating to the use of zinc fingers for targeted recombination. The use of recombinases (cre-10× and flp-frt for example) is also known in the art.

AAD-13 detoxification is believed to occur in the cytoplasm. Thus, means for further stabilizing this protein and mRNAs (including blocking mRNA degradation) are included in aspects of the subject invention, and art-known techniques can be applied accordingly. The subject proteins can be designed to resist degradation by proteases and the like (protease cleavage sites can be effectively removed by re-engineering the amino acid sequence of the protein). Such embodiments include the use of 5' and 3' stem loop structures like UTRs from osmotin, and per5 (AU-rich untranslated 5' sequences). 5' caps like 7-methyl or 2'-O-methyl groups, e.g., 7-methylguanylic acid residue, can also be used. See, e.g., Proc. Natl. Acad. Sci. USA Vol. 74, No. 7, pp. 2734-2738 (July 1977) *Importance of 5'-terminal blocking structure to stabilize mRNA in eukaryotic protein synthesis.* Protein complexes or ligand blocking groups can also be used.

Computational design of 5' or 3' UTR most suitable for AAD-13 (synthetic hairpins) can also be conducted within the scope of the subject invention. Computer modeling in general, as well as gene shuffling and directed evolution, are discussed elsewhere herein. More specifically regarding computer modeling and UTRs, computer modeling techniques for use in predicting/evaluating 5' and 3' UTR derivatives of the present invention include, but are not limited to: MFold version 3.1 available from Genetics Corporation Group, Madison, Wis. (see Zucker et al., Algorithms and Thermodynamics for RNA Secondary Structure Prediction: A Practical Guide. In *RNA Biochemistry and Biotechnology*, 11-43, J. Barciszewski & B. F. C. Clark, eds., NATO ASI Series, Kluwer Academic Publishers, Dordrecht, NL, (1999); Zucker et al., *Expanded Sequence Dependence of Thermodynamic Parameters Improves Prediction of RNA Secondary Structure. J. Mol. Biol.* 288, 911-940 (1999); Zucker et al., RNA Secondary Structure Prediction. In *Current Protocols in*

Nucleic Acid Chemistry S. Beaucage, D. E. Bergstrom, G. D. Glick, and R. A. Jones eds., John Wiley & Sons, New York, 11.2.1-11.2.10, (2000)), COVE (RNA structure analysis using covariance models (stochastic context free grammar methods)) v.2.4.2 (Eddy & Durbin, Nucl. Acids Res. 1994, 22: 2079-2088) which is freely distributed as source code and which can be downloaded by accessing the website genetics.wustl.edu/eddy/software/, and FOLDALIGN, also freely distributed and available for downloading at the website bioinf.au.dk. FOLDALIGN/ (see *Finding the most significant common sequence and structure motifs in a set of RNA sequences*. J. Gorodkin, L. J. Heyer and G. D. Stormo. Nucleic Acids Research, Vol. 25, no. 18 pp 3724-3732, 1997; *Finding Common Sequence and Structure Motifs in a set of RNA Sequences*. J. Gorodkin, L. J. Heyer, and G. D. Stormo. ISMB 5; 120-123, 1997).

Embodiments of the subject invention can be used in conjunction with naturally evolved or chemically induced mutants (mutants can be selected by screening techniques, then transformed with AAD-13 and possibly other genes). Plants of the subject invention can be combined with ALS resistance and/or evolved glyphosate resistance. Aminopyralid resistance, for example, can also be combined or "stacked" with an AAD-13 gene.

Traditional breeding techniques can also be combined with the subject invention to powerfully combine, introgress, and improve desired traits.

Further improvements also include use with appropriate safeners to further protect plants and/or to add cross resistance to more herbicides. (Safeners typically act to increase plants immune system by activating/expressing cP450. Safeners are chemical agents that reduce the phytotoxicity of herbicides to crop plants by a physiological or molecular mechanism, without compromising weed control efficacy.)

Herbicide safeners include benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, and oxabetrinil. Plant activators (a new class of compounds that protect plants by activating their defense mechanisms) can also be used in embodiments of the subject invention. These include acibenzolar and probenazole.

Commercialized safeners can be used for the protection of large-seeded grass crops, such as corn, grain sorghum, and wet-sown rice, against preplant-incorporated or preemergence-applied herbicides of the thiocarbamate and chloroacetanilide families. Safeners also have been developed to protect winter cereal crops such as wheat against postemergence applications of aryloxyphenoxypropionate and sulfonylurea herbicides. The use of safeners for the protection of corn and rice against sulfonylurea, imidazolinone, cyclohexanedione, isoxazole, and triketone herbicides is also well-established. A safener-induced enhancement of herbicide detoxification in safened plants is widely accepted as the major mechanism involved in safener action. Safeners induce cofactors such as glutathione and herbicide-detoxifying enzymes such as glutathione S-transferases, cytochrome P450 monooxygenases, and glucosyl transferases. Hatzios K K, Burgos N (2004) "Metabolism-based herbicide resistance: regulation by safeners," Weed Science: Vol. 52, No. 3 pp. 454-467.

Use of a cytochrome p450 monooxygenase gene stacked with AAD-13 is one preferred embodiment. There are P450s involved in herbicide metabolism; cP450 can be of mammalian or plant origin, for example. In higher plants, cytochrome P450 monooxygenase (P450) is known to conduct secondary metabolism. It also plays an important role in the oxidative metabolism of xenobiotics in cooperation with NADPH-cytochrome P450 oxidoreductase (reductase). Resistance to some herbicides has been reported as a result of the metabolism by P450 as well as glutathione S-transferase. A number of microsomal P450 species involved in xenobiotic metabolism in mammals have been characterized by molecular cloning. Some of them were reported to metabolize several herbicides efficiently. Thus, transgenic plants with plant or mammalian P450 can show resistance to several herbicides.

One preferred embodiment of the foregoing is the use cP450 for resistance to acetochlor (acetochlor-based products include Surpass®, Keystone®, Keystone LA, FulTime® and TopNotch® herbicides) and/or trifluralin (such as Treflan®). Such resistance in soybeans and/or corn is included in some preferred embodiments. For additional guidance regarding such embodiments, see e.g. Inui et al., "A selectable marker using cytochrome P450 monooxygenases for *Arabidopsis* transformation," *Plant Biotechnology* 22, 281-286 (2005) (relating to a selection system for transformation of *Arabidopsis thaliana* via *Agrobacterium tumefaciens* that uses human cytochrome P450 monooxygenases that metabolize herbicides; herbicide tolerant seedlings were transformed and selected with the herbicides acetochlor, amiprophos-methyl, chlorpropham, chlorsulfuron, norflurazon, and pendimethalin); Siminszky et al., "Expression of a soybean cytochrome P450 monooxygenase cDNA in yeast and tobacco enhances the metabolism of phenylurea herbicides," *PNAS* Vol. 96, Issue 4, 1750-1755, Feb. 16, 1999; Sheldon et al, *Weed Science*: Vol. 48, No. 3, pp. 291-295, "A cytochrome P450 monooxygenase cDNA (CYP71A10) confers resistance to linuron in transgenic *Nicotiana tabacum*"; and "Phytoremediation of the herbicides atrazine and metolachlor by transgenic rice plants expressing human CYP1A1, CYP2B6, and CYP2C19," *J Agric Food Chem*. 2006 Apr. 19; 54(8):2985-91 (relating to testing a human cytochrome p450 monooxygenase in rice where the rice plants reportedly showed high tolerance to chloroacetomides (acetochlor, alachlor, metoachlor, pretilachlor, and thenylchlor), oxyacetamides (mefenacet), pyridazinones (norflurazon), 2,6-dinitroanalines (trifluralin and pendimethalin), phosphamidates (amiprofos-methyl, thiocarbamates (pyributicarb), and ureas (chlortoluron)).

There is also the possibility of altering or using different 2,4-D chemistries to make the subject AAD-13 gene more efficient. Such possible changes include creating better substrates and better leaving groups (higher electronegativity).

Auxin transport inhibitors (e.g. diflufenzopyr) can also be used to increase herbicide activity with 2,4-D.

Unless specifically indicated or implied, the terms "a", "an", and "the" signify "at least one" as used herein.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Method for Identifying Genes that Impart Herbicide Resistance in Planta

As a way to identify genes which possess herbicide degrading activities in planta, it is possible to mine current public databases such as NCBI (National Center for Biotechnology Information). To begin the process, it is necessary to have a functional gene sequence already identified that encodes a protein with the desired characteristics (i.e., α-ketoglutarate dioxygenase activity). This protein sequence is then used as the input for the BLAST (Basic Local Alignment Search Tool) (Altschul et al., 1997) algorithm to compare against available NCBI protein sequences deposited. Using default settings, this search returns upwards of 100 homologous protein sequences at varying levels. These range from highly identical (85-98%) to very low identity (23-35%) at the amino acid level. Traditionally only sequences with high homology would be expected to retain similar properties to the input sequence. In this case, only sequences with ≤50% homology were chosen. As exemplified herein, cloning and recombinantly expressing homologues with as little as 35% amino acid conservation (relative to tfdA from *Ralstonia eutropha*) can be used to impart commercial levels of resistance not only to the intended herbicide, but also to substrates never previously tested with these enzymes.

A single gene (sdpA) was identified from the NCBI database (see the ncbi.nlm.nih.gov website; accession #AJ628860) as a homologue with only 35% amino acid identity to tfdA. Percent identity was determined by first translating both the sdpA and tfdA DNA sequences deposited in the database to proteins, then using ClustalW in the Vector NTI software package to perform the multiple sequence alignment.

Example 2

Optimization of Sequence for Expression in Plants and Bacteria 2.1—Background.

To obtain higher levels of expression of heterologous genes in plants, it may be preferred to re-engineer the protein encoding sequence of the genes so that they are more efficiently expressed in plant cells. Maize is one such plant where it may be preferred to re-design the heterologous protein coding region prior to transformation to increase the expression level of the gene and the level of encoded protein in the plant. Therefore, an additional step in the design of genes encoding a bacterial protein is re-engineering of a heterologous gene for optimal expression.

One reason for the re-engineering of a bacterial gene for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences such as AAUAAA, or sequences complementary to small nuclear RNAs involved in pre-mRNA splicing) may lead to RNA instability. Therefore, one goal in the design of genes encoding a bacterial protein for maize expression, more preferably referred to as plant optimized gene(s), is to generate a DNA sequence having a G+C content preferably close to that of maize genes coding for metabolic enzymes. Another goal in the design of the plant optimized gene(s) encoding a bacterial protein is to generate a DNA sequence in which the sequence modifications do not hinder translation.

Table Ex2-1 presents the G+C content of maize genes. For the data in Table Ex2-1, coding regions of the genes were extracted from GenBank (Release 71) entries, and base compositions were calculated using the MacVector™ program (Accelerys, San Diego, Calif.). Intron sequences were ignored in the calculations.

TABLE Ex2-1

Compilation of G + C contents of protein coding regions of maize genes

| Protein Class[a] | Range % G + C | Mean % G + C[b] |
|---|---|---|
| Metabolic Enzymes (76) | 44.4-75.3 | 59.0 (. ± .8.0) |
| Structural Proteins (18) | 48.6-70.5 | 63.6 (. ± .6.7) |
| Regulatory Proteins (5) | 57.2-68.8 | 62.0 (. ± .4.9) |
| Uncharacterized Proteins (9) | 41.5-70.3 | 64.3 (. ± .7.2) |
| All Proteins (108) | 44.4-75.3 | 60.8 (. ± .5.2)[c] |

[a]Number of genes in class given in parentheses.
[b]Standard deviations given in parentheses.
[c]Combined groups mean ignored in mean calculation Multiple publicly available DNA sequence databases exist wherein one may find information about the G+C contents of plant genomes or the protein coding regions of various plant genes. One such database is located on the World Wide Web at website kazusa.or.jp/codon/. At this site, one may find that the average G+C content of, for example, tobacco (*Nicotiana tabacum*) protein coding sequences is 43.3% (analysis of 1268 sequences comprising 453,797 codons). One may also find that the average G+C content of maize (*Zea mays*) protein coding sequences is 54.9% (analysis of 2280 sequences comprising 973,578 codons). In comparison, the G+C content of the *Sphingobium herbicidovorans* AAD-13 protein coding sequence disclosed in SEQ ID NO:2 is 67.2%. Thus, it may be advantageous when designing an AAD-13 gene for expression in maize or dicots to lower the G+C content of the protein coding region to a range of 40-55%. Therefore, one goal in the design of genes encoding a bacterial protein for plant expression, more preferably referred to as plant optimized gene(s), is to generate a DNA sequence having a G+C content preferably close to that of native host plant genes coding for metabolic enzymes.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within an mRNA may reduce the absolute translation rate of that mRNA, especially when the relative abundance of the charged tRNA corresponding to the minor codon is low. An extension of this is that the diminution of translation rate by individual minor codons would be at least an additive for multiple minor codons. Therefore, mRNAs having high relative contents of minor codons would have correspondingly low translation rates. This rate would be reflected by subsequent low levels of the encoded protein.

In engineering genes encoding a bacterial protein for expression in maize (or other plants, such as cotton or soybean), it is helpful if the codon bias of the prospective host plant(s) has been determined. The codon bias can be calculated as the frequency at which a single codon is used relative to the codons for all amino acids. Alternatively, as disclosed in Table Ex2-2, Columns C, D, I and J, the codon bias may be calculated as the frequency at which a single codon is used to encode a particular amino acid, relative to all the other codons for that amino acid (synonymous codons). The codon bias for maize is the statistical codon distribution that the plant uses for coding its proteins, and the codon usage calculated from 706 maize genes is shown in Table Ex2-2, Columns C and I. In designing coding regions for genes encoding bacterial proteins destined for plant expression, the primary ("first choice") codons preferred by the plant should be determined, as well as the second, third, fourth etc. choices of preferred codons when multiple choices exist. A new DNA sequence can then be designed which encodes the amino sequence of the bacterial protein, but the new DNA sequence differs from the native bacterial DNA sequence (encoding the protein) by the substitution of plant (first preferred, second preferred, third preferred, or fourth preferred, etc.) codons to specify the amino acid at each position within the protein amino acid sequence. The new sequence is then analyzed for restriction enzyme sites that might have been created by the modifications. The identified sites are further modified by replacing the codons with first, second, third, or fourth choice preferred codons. Other sites in the sequence which could affect transcription or translation of the gene of interest are the exon: intron junctions (5' or 3'), poly A addition signals, or RNA polymerase termination signals. The sequence is further analyzed and modified to reduce the frequency of TA or CG doublets. In addition to the doublets, G or C sequence blocks that have more than about six residues that are the same can affect transcription or translation of the sequence. Therefore, these blocks are advantageously modified by replacing the codons of first or second choice, etc. with the next preferred codon of choice.

Thus, in order to design plant optimized genes encoding a bacterial protein, a DNA sequence is designed to encode the amino acid sequence of said protein utilizing a redundant genetic code established from a codon bias table compiled from the gene sequences for the particular plant or plants. The resulting DNA sequence has a higher degree of codon diversity, a desirable base composition, can contain strategically placed restriction enzyme recognition sites, and lacks sequences that might interfere with transcription of the gene, or translation of the product mRNA. Such synthetic genes that are functionally equivalent to the genes/proteins of the subject invention can be used to transform hosts, including plants. Additional guidance regarding the production of synthetic genes can be found in, for example, U.S. Pat. No. 5,380,831 and PCT application WO 97/13402.

To engineer a plant-optimized gene encoding an AAD-13 protein, a DNA sequence was designed to encode the AAD-13 amino acid sequence, utilizing a redundant genetic code established from codon bias tables compiled from the protein coding sequences for the particular host plants (maize and dicots). In Table Ex2-2, Columns C, D, I, and J present the distributions (in % of usage for all codons for that amino acid) of synonymous codons for each amino acid, as found in 706 coding regions of *Zea mays* (maize) and 154 dicot genes [REF: Murray, E. E., Lotzer, J., Eberle, M. (1989) Codon usage in plant genes. Nucl. Acids Res. 17:477-497]. The codons most preferred by each plant type are indicated in bold font, and the second, third, or fourth choices of codons can be identified when multiple choices exist. It is evident that some synonymous codons for some amino acids are found only rarely in plant genes (e.g. AGT in maize and CCG in dicots). Also, maize and dicot plants differ in individual codon usage (e.g. Alanine codon GCG occurs more frequently in maize genes than in dicot genes, while Arginine codon AGA is more often used in dicot genes than in maize genes). Thus, it is obvious that a protein coding region designed to reflect the optimal codon composition of genes of one plant species may have a suboptimal codon composition for expression in another plant species. In the design process of creating a protein-encoding DNA sequence that approximates an average codon distribution of both maize and dicot genes, any codon that is used infrequently relative to the other synonymous codons for that amino acid in either type of plant was excluded (indicated by DNU in Columns F and L of Table Ex2-2). Usually, a codon was considered to be rarely used if it is represented at about 10% or less of the time to encode the relevant amino acid in genes of either plant type (indicated by NA in Columns E and K of Table Ex2-2). To balance the distribution of the remaining codon choices for an amino acid, a Weighted Average representation for each codon was calculated, using the formula:

Weighted Average % of C1=1/(% C1+% C2+% C3+etc.)×% C1×100 where C1 is the codon in question and % C2, % C3, etc. represent the % average values for maize and dicots of remaining synonymous codons (% average values for the relevant codons are taken from Columns E and K) of Table Ex2-2.

The Weighted Average % value for each codon is given in Columns F and L of Table Ex2-2.

TABLE Ex2-2

Synonymous codon representation in coding regions of 706 *Zea mays* (maize) genes (Columns C and I), and 154 dicot genes (Columns D and J). Values for a balanced-biased codon representation set for a plant-optimized synthetic gene design are in Columns F and L.

| A Amino Acid | B Codon | C Maize % | D Dicot % | E Maize-Dicot Average | F Weighted Average | G Amino Acid | H Codon | I Maize % | J Dicot % | K Maize-Dicot Average | L Weighted Average |
|---|---|---|---|---|---|---|---|---|---|---|---|
| ALA (A) | GCA | 18 | 25 | 21.7 | 25.5 | LEU (L) | CTA | 8 | 8 | NA | DNU |
|  | GCC | 34 | 27 | 30.3 | 35.6 |  | CTC | 26 | 19 | 22.5 | 34.3 |
|  | GCG | 24 | 6 | NA | DNU |  | CTG | 29 | 9 | NA | DNU |
|  | GCT | 24 | 42 | 33.2 | 39.0 |  | CTT | 17 | 28 | 22.5 | 34.3 |
| ARG (R) | AGA | 15 | 30 | 22.4 | 27.4 |  | TTA | 5 | 10 | NA | DNU |
|  | AGG | 26 | 25 | 25.7 | 31.5 |  | TTG | 15 | 26 | 20.6 | 31.4 |

TABLE Ex2-2-continued

Synonymous codon representation in coding regions of 706 Zea mays (maize) genes (Columns C and I), and 154 dicot genes (Columns D and J). Values for a balanced-biased codon representation set for a plant-optimized synthetic gene design are in Columns F and L.

| A Amino Acid | B Codon | C Maize % | D Dicot % | E Maize-Dicot Average | F Weighted Average | G Amino Acid | H Codon | I Maize % | J Dicot % | K Maize-Dicot Average | L Weighted Average |
|---|---|---|---|---|---|---|---|---|---|---|---|
| | CGA | 9 | 8 | NA | DNU | LYS (K) | AAA | 22 | 39 | 30.6 | 30.6 |
| | CGC | 24 | 11 | 17.7 | 21.7 | | AAG | 78 | 61 | 69.4 | 69.4 |
| | CGG | 15 | 4 | NA | DNU | MET (M) | ATG | 100 | 100 | 100 | 100 |
| | CGT | 11 | 21 | 15.8 | 19.4 | PHE (F) | TTC | 71 | 55 | 63.2 | 63.2 |
| ASN (N) | AAC | 68 | 55 | 61.4 | 61.4 | | TTT | 29 | 45 | 36.8 | 36.8 |
| | AAT | 32 | 45 | 38.6 | 38.6 | PRO (P) | CCA | 26 | 42 | 33.8 | 41.4 |
| ASP (D) | GAC | 63 | 42 | 52.6 | 52.6 | | CCC | 24 | 17 | 20.7 | 25.3 |
| | GAT | 37 | 58 | 47.4 | 47.4 | | CCG | 28 | 9 | NA | DNU |
| CYS (C) | TGC | 68 | 56 | 61.8 | 61.8 | | CCT | 22 | 32 | 27.2 | 33.3 |
| | TGT | 32 | 44 | 38.2 | 38.2 | SER (S) | AGC | 23 | 18 | 20.4 | 26.0 |
| END | TAA | 20 | 48 | 33.8 | | | AGT | 9 | 14 | NA | DNU |
| | TAG | 21 | 19 | 20.1 | | | TCA | 16 | 19 | 17.5 | 22.4 |
| | TGA | 59 | 33 | 46.1 | | | TCC | 23 | 18 | 20.6 | 26.3 |
| GLN (Q) | CAA | 38 | 59 | 48.4 | 48.4 | | TCG | 14 | 6 | NA | DNU |
| | CAG | 62 | 41 | 51.6 | 51.6 | | TCT | 15 | 25 | 19.9 | 25.4 |
| GLU (E) | GAA | 29 | 49 | 38.8 | 38.8 | THR (T) | ACA | 21 | 27 | 23.8 | 28.0 |
| | GAG | 71 | 51 | 61.2 | 61.2 | | ACC | 37 | 30 | 33.6 | 39.5 |
| GLY (G) | GGA | 19 | 38 | 28.5 | 28.5 | | ACG | 22 | 8 | NA | DNU |
| | GGC | 42 | 16 | 29.1 | 29.0 | | ACT | 20 | 35 | 27.7 | 32.5 |
| | GGG | 20 | 12 | 16.1 | 16.0 | TRP (W) | TGG | 100 | 100 | 100 | 100 |
| | GGT | 20 | 33 | 26.7 | 26.6 | TYR (Y) | TAC | 73 | 57 | 65.0 | 65.0 |
| HIS (H) | CAC | 62 | 46 | 54.1 | 54.1 | | TAT | 27 | 43 | 35.0 | 35.0 |
| | CAT | 38 | 54 | 45.9 | 45.9 | VAL (V) | GTA | 8 | 12 | NA | DNU |
| ILE (I) | ATA | 14 | 18 | 15.9 | 15.9 | | GTC | 32 | 20 | 25.8 | 28.7 |
| | ATC | 58 | 37 | 47.6 | 47.9 | | GTG | 39 | 29 | 34.1 | 38.0 |
| | ATT | 28 | 45 | 36.4 | 36.4 | | GTT | 21 | 39 | 29.9 | 33.3 |

A new DNA sequence which encodes essentially the amino acid sequence of the *Sphingobium herbicidovorans* AAD-13 protein of SEQ ID NO:2 was designed for optimal expression in both maize and dicot cells using a balanced codon distribution of frequently used codons found in maize and dicot genes.

2.2—AAD-13 Plant Rebuild Analysis.

Extensive analysis of the 861 base pairs (bp) of the coding region of the native DNA sequence of AAD-13 (SEQ ID NO:1) revealed the presence of several sequence motifs that are thought to be detrimental to optimal plant expression, as well as a non-optimal codon composition. The protein encoded by SEQ ID NO:1 (AAD-13) is presented as SEQ ID NO:2. To improve production of the recombinant protein in maize as well as dicots, a "plant-optimized" DNA sequence (AAD-13 v1) (SEQ ID NO:3) was developed that encodes a protein (SEQ ID NO:4) which is the same as the native protein disclosed in SEQ ID NO:2 except for the addition of an alanine residue at the second position (underlined in SEQ ID NO:4). The additional alanine codon (GCT; underlined in SEQ ID NO:3) encodes part of an Nco I restriction enzyme recognition site (CCATGG) spanning the ATG translational start codon. Thus, it serves the dual purpose of facilitating subsequent cloning operations while improving the sequence context surrounding the ATG start codon to optimize translation initiation. The proteins encoded by the native and plant-optimized (v1) coding regions are 99.3% identical, differing only at amino acid number 2. In contrast, the native and plant-optimized (v1) DNA sequences of the coding regions are only 77.3% identical. Table Ex2-3 shows the differences in codon compositions of the native (Columns A and D) and plant-optimized sequences (Columns B and E), and allows comparison to a theoretical plant-optimized sequence (Columns C and F) that would have precisely the codon composition dictated by columns F and L of Table Ex2-2.

TABLE Ex2-3

Codon composition comparisons of coding regions of Native AAD-13, Plant-Optimized version (v1) and a Theoretical Plant-Optimized version.

| Amino Acid | Codon | A Native | B Plant Opt v1 # | C Theor. Plant Opt. # | Amino Acid | Codon | D Native | E Plant Opt v1 # | F Theor. Plant Opt. # |
|---|---|---|---|---|---|---|---|---|---|
| ALA (A) | GCA | 1 | 10 | 9 | LEU (L) | CTA | 0 | 0 | 0 |
|  | GCC | 24 | 11 | 13 |  | CTC | 11 | 11 | 10 |
|  | GCG | 10 | 0 | 0 |  | CTG | 17 | 0 | 0 |
|  | GCT | 1 | 16 | 14 |  | CTT | 0 | 10 | 10 |
| ARG (R) | AGA | 0 | 4 | 4 |  | TTA | 0 | 0 | 0 |
|  | AGG | 0 | 5 | 5 |  | TTG | 2 | 9 | 9 |
|  | CGA | 1 | 0 | 0 | LYS (K) | AAA | 0 | 3 | 3 |
|  | CGC | 10 | 4 | 3 |  | AAG | 10 | 7 | 7 |
|  | CGG | 4 | 0 | 0 | MET (M) | ATG | 9 | 9 | 9 |
|  | CGT | 1 | 3 | 3 | PHE (F) | TTC | 8 | 6 | 6 |
| ASN (N) | AAC | 3 | 2 | 2 |  | TTT | 1 | 3 | 3 |
|  | AAT | 1 | 2 | 2 | PRO (P) | CCA | 2 | 7 | 7 |
| ASP (D) | GAC | 19 | 13 | 13 |  | CCC | 5 | 5 | 5 |
|  | GAT | 5 | 11 | 11 |  | CCG | 10 | 0 | 0 |
| CYS (C) | TGC | 2 | 1 | 1 |  | CCT | 1 | 6 | 6 |
|  | TGT | 0 | 1 | 1 | SER (S) | AGC | 9 | 4 | 4 |
| END | TAA | 0 | 0 |  |  | AGT | 1 | 0 | 0 |
|  | TAG | 0 | 0 |  |  | TCA | 1 | 3 | 3 |
|  | TGA | 1 | 1 | 1 |  | TCC | 1 | 4 | 4 |
| GLN (Q) | CAA | 0 | 7 | 7 |  | TCG | 3 | 0 | 0 |
|  | CAG | 14 | 7 | 7 |  | TCT | 0 | 4 | 4 |
| GLU (E) | GAA | 3 | 5 | 5 | THR (T) | ACA | 0 | 3 | 3 |
|  | GAG | 11 | 9 | 9 |  | ACC | 7 | 4 | 4 |
| GLY (G) | GGA | 1 | 6 | 6 |  | ACG | 4 | 0 | 0 |
|  | GGC | 16 | 6 | 6 |  | ACT | 0 | 4 | 4 |
|  | GGG | 3 | 3 | 3 | TRP (W) | TGG | 7 | 7 | 7 |
|  | GGT | 1 | 6 | 6 | TYR (Y) | TAC | 5 | 4 | 5 |
| HIS (H) | CAC | 7 | 7 | 8 |  | TAT | 2 | 3 | 2 |
|  | CAT | 7 | 7 | 6 | VAL (V) | GTA | 0 | 0 | 0 |
| ILE (I) | ATA | 0 | 2 | 2 |  | GTC | 6 | 4 | 4 |
|  | ATC | 10 | 5 | 5 |  | GTG | 7 | 6 | 6 |

TABLE Ex2-3-continued

Codon composition comparisons of coding regions of Native AAD-13,
Plant-Optimized version (v1) and a Theoretical Plant-Optimized version.

| Amino Acid | Codon | A Native | B Plant Opt v1 # | C Theor. Plant Opt. # | Amino Acid | Codon | D Native | E Plant Opt v1 # | F Theor. Plant Opt. # |
|---|---|---|---|---|---|---|---|---|---|
| | ATT | 1 | 4 | 4 | | GTT | 2 | 5 | 5 |
| | Totals | 157 | 158 | 158 | | Totals | 131 | 131 | 131 |

It is clear from examination of Table Ex2-3 that the native and plant-optimized coding regions, while encoding nearly identical proteins, are substantially different from one another. The Plant-Optimized version (v1) closely mimics the codon composition of a theoretical plant-optimized coding region encoding the AAD-13 protein.

2.3 Rebuild for E. coli Expression

Specially engineered strains of *Escherichia coli* and associated vector systems are often used to produce relatively large amounts of proteins for biochemical and analytical studies. It is sometimes found that a native gene encoding the desired protein is not well suited for high level expression in *E. coli*, even though the source organism for the gene may be another bacterial organism. In such cases it is possible and desirable to re-engineer the protein coding region of the gene to render it more suitable for expression in *E. coli*. *E. coli* Class II genes are defined as those that are highly and continuously expressed during the exponential growth phase of *E. coli* cells. [REF: Henaut, A. and Danchin, A. (1996) in *Escherichia coli and Salmonella typhimurium cellular and molecular biology, vol.* 2, pp. 2047-2066, Neidhardt, F., Curtiss III R., Ingraham, J., Lin, E., Low, B., Magasanik, B., Reznikoff, W. Riley, M., Schaechter, M. and Umbarger, H, (eds.) American Society for Microbiology, Washington, D.C.]. Through examination of the codon compositions of the coding regions of *E. coli* Class II genes, one can devise an average codon composition for these *E. coli* Class II gene coding regions. It is thought that a protein coding region having an average codon composition mimicking that of the Class II genes will be favored for expression during the exponential growth phase of *E. coli*. Using these guidelines, a new DNA sequence that encodes the AAD-13 protein (SEQ ID NO:4; including the additional alanine at the second position, as mentioned above), was designed according to the average codon composition of *E. coli* Class II gene coding regions. The initial sequence, whose design was based only on codon composition, was further engineered to include certain restriction enzyme recognition sequences suitable for cloning into *E. coli* expression vectors. Detrimental sequence features such as highly stable stemloop structures were avoided, as were intragenic sequences homologous to the 3' end of the 16S ribosomal RNA (i.e. Shine Dalgarno sequences) The *E. coli*-optimized sequence (v2) is disclosed as SEQ ID NO:5 and encodes the protein disclosed in SEQ ID NO:4.

The native and *E. coli*-optimized (v2) DNA sequences are 80.2% identical, while the plant-optimized (v1) and *E. coli*-optimized (v2) DNA sequences are 84.4% identical. Table Ex2-4 presents the codon compositions of the native AAD-13 coding region; Columns A and D), the AAD-13 coding region optimized for expression in *E. coli* (v2; Columns B and E) and the codon composition of a theoretical coding region for the AAD-13 protein having an optimal codon composition of *E. coli* Class II genes (Columns C and F).

TABLE Ex2-4

Codon composition comparisons of coding regions of Native AAD-13,
E. coli-Optimized version (v2) and a Theoretical E. coli Class
II-Optimized version.

| Amino Acid | Codon | A Native | B E. coli Opt v2 # | C Theor. Class II # | Amino Acid | Codon | D Native | E E. coli Opt v2 # | F Theor, Class II # |
|---|---|---|---|---|---|---|---|---|---|
| ALA (A) | GCA | 1 | 11 | 11 | LEU (L) | CTA | 0 | 0 | 0 |
| | GCC | 24 | 0 | 0 | | CTC | 11 | 0 | 0 |
| | GCG | 10 | 14 | 14 | | CTG | 17 | 30 | 30 |
| | GCT | 1 | 12 | 12 | | CTT | 0 | 0 | 0 |
| ARG (R) | AGA | 0 | 0 | 0 | | TTA | 0 | 0 | 0 |
| | AGG | 0 | 0 | 0 | | TTG | 2 | 0 | 0 |
| | CGA | 1 | 0 | 0 | LYS (K) | AAA | 0 | 8 | 8 |
| | CGC | 10 | 7 | 5 | | AAG | 10 | 2 | 2 |
| | CGG | 4 | 0 | 0 | MET (M) | ATG | 9 | 9 | 9 |
| | CGT | 1 | 9 | 11 | PHE (F) | TTC | 8 | 6 | 6 |

TABLE Ex2-4-continued

Codon composition comparisons of coding regions of Native AAD-13,
E. coli-Optimized version (v2) and a Theoretical E. coli Class
II-Optimized version.

| Amino Acid | Codon | A Native | B E. coli Opt v2 # | C Theor. Class II # | Amino Acid | Codon | D Native | E E. coli Opt v2 # | F Theor, Class II # |
|---|---|---|---|---|---|---|---|---|---|
| ASN (N) | AAC | 3 | 4 | 4 | | TTT | 1 | 3 | 3 |
| | AAT | 1 | 0 | 0 | PRO (P) | CCA | 2 | 3 | 3 |
| ASP (D) | GAC | 19 | 13 | 13 | | CCC | 5 | 0 | 0 |
| | GAT | 5 | 11 | 11 | | CCG | 10 | 15 | 15 |
| CYS (C) | TGC | 2 | 1 | 1 | | CCT | 1 | 0 | 0 |
| | TGT | 0 | 1 | 1 | SER (S) | AGC | 9 | 4 | 4 |
| END | TAA | 0 | 1 | 1 | | AGT | 1 | 0 | 0 |
| | TAG | 0 | 0 | 0 | | TCA | 1 | 0 | 0 |
| | TGA | 1 | 0 | 0 | | TCC | 1 | 5 | 5 |
| GLN (Q) | CAA | 0 | 3 | 3 | | TCG | 3 | 0 | 0 |
| | CAG | 14 | 11 | 11 | | TCT | 0 | 6 | 6 |
| GLU (E) | GAA | 3 | 10 | 11 | THR (T) | ACA | 0 | 0 | 0 |
| | GAG | 11 | 4 | 3 | | ACC | 7 | 7 | 7 |
| GLY (G) | GGA | 1 | 0 | 0 | | ACG | 4 | 0 | 0 |
| | GGC | 16 | 10 | 10 | | ACT | 0 | 4 | 4 |
| | GGG | 3 | 0 | 0 | TRP (W) | TGG | 7 | 7 | 7 |
| | GGT | 1 | 11 | 11 | TYR (Y) | TAC | 5 | 5 | 5 |
| HIS (H) | CAC | 7 | 10 | 10 | | TAT | 2 | 2 | 2 |
| | CAT | 7 | 4 | 4 | VAL (V) | GTA | 0 | 3 | 3 |
| ILE (I) | ATA | 0 | 0 | 0 | | GTC | 6 | 0 | 0 |
| | ATC | 10 | 7 | 7 | | GTG | 7 | 5 | 5 |
| | ATT | 1 | 4 | 4 | | GTT | 2 | 7 | 7 |
| | Totals | 157 | 158 | 158 | | Totals | 131 | 131 | 131 |

It is clear from examination of Table Ex2-4 that the native and E. coli-optimized coding regions, while encoding nearly identical proteins, are substantially different from one another. The E. coli-Optimized version (v2) closely mimics the codon composition of a theoretical E. coli-optimized coding region encoding the AAD-13 protein.

Example 3

Cloning of Expression and Transformation Vectors 3.1 Construction of E. coli, pET Expression Vector.

Using the restriction enzymes corresponding to the sites added with the additional cloning linkers (Xba 1, Xho 1) AAD-13 (v2) was cut out of the picoscript vector, and ligated into a pET280 streptomycin/spectinomycin resistant vector. Ligated products were then transformed into TOP10F' E. coli, and plated on to Luria Broth+50 µg/ml Streptomycin & Spectinomycin (LB S/S) agar plates.

To differentiate between AAD-13 (v2): pET280 and pCR2.1: pET280 ligations, approximately 20 isolated colonies were picked into 6 ml of LB-S/S, and grown at 37° C. for 4 hours with agitation. Each culture was then spotted onto LB+Kanamycin 50 µg/ml plates, which were incubated at 37° C. overnight. Colonies that grew on the LB-K were assumed to have the pCR2.1 vector ligated in, and were discarded. Plasmids were isolated from the remaining cultures as before, and checked for correctness with digestion by Fsp1. The final expression construct was given the designation pDAB4115.

3.3—Completion of Binary Vectors.

The plant optimized gene AAD-13 (v1) was received from Picoscript (the gene rebuild design was completed (see above) and out-sourced to Picoscript for construction) The AAD-13 (v1) gene was cloned into pDAB4055 as an Nco I-Sac I fragment. The resulting construct was designated pDAB4113, containing: [AtUbi10 promoter: AAD-13 (v1): AtuORF1 3'UTR] (verified with Nco I and Sac I restriction digests). A Not I-Not I fragment containing the described cassette was then cloned into the Not I site of the binary vector pDAB3038. The resulting binary vector, pDAB4114, containing the following cassette [AtUbi10 promoter: AAD-13

(v1): AtuORF1 3'UTR: CsVMV promoter: PAT: ORF25/26 3'UTR] was restriction digested (with SacI) for verification of the correct orientation. The verified completed construct (pDAB4114) was used for transformation into *Agrobacterium* (see Example 6).

Example 4

Recombinant AAD-13 Expression and Purification in *Pseudomonas fluorescens*

4.1—*Pseudomonas fluorescens* Fermentation

For shake flask experiment, 200 µl of the *Pseudomonas fluorescens* strain glycerol stock carrying the AAD-13 (v1) construct (sec 3.2) will be used to inoculate 50 ml fresh LB media supplemented with 30 µg/ml tetracycline/HCl. The culture (in a 250 ml baffled Erlenmeyer flask) will be incubated on a shaker (New Brunswick Scientific Model Innova 44) at 300 rpm and 30° C. for 16 hrs. 20 ml of seed culture will be transferred into 1 L *Pseudomonas fluorescens* culture media (Yeast extract, 5 g/L; $K_2HPO_4$, 5 g/L; $(NH_4)_2PO_4$, 7.5 g/L; $(NH_4)_2SO_4$; $MgSO_4$-$7H_2O$, 1 g/L; KCl, 0.5 g/L; $CaCl_2$-$2H_2O$, 0.5 g/L; NaCitrate-$2H_2O$, 15 g/L; Glycerol, 95 g/L; Trace element solution, 10 ml/L; Trace element solution: $FeCl_3$-$6H_2O$, 5.4 g/L; $MnCl_2$-$4H_2O$, 1 g/L; $ZnSO_4$-$7H_2O$, 1.45 g/L; $CuSO_4$-$5H_2O$, 0.25 g/L; $H_3BO_3$, 0.1 g/L; $(NH_4)_6MO_7O_{24}$, 0.1 g/L; concentrated HCl, 13 ml/L) supplemented with 20 µg/ml tetracycline/HCl and 250 µl of Pluronic L61 (anti-foam) in a 2.8 L baffled Erlenmeyer flask. The cultures are to be incubated at 30° C. and 300 rpm for 24 hrs. Isopropyl β-D-1-thiogalacto-pyranoside (IPTG) will be added to 1 mM final in the cultures and continued to incubate for approximately 48 hrs at 25° C. Cells are harvested by centrifugation at 7 krpm at 4° C. for 15 min, and cell paste is stored at −80° C. or immediately processed for purification.

For tank experiments, 1 ml each of the glycerol stock will be inoculated a 1 L baffled flask containing 200 ml of LB media supplemented with 30 µg/ml tetracycline/HCl at 300 rpm and 32° C. for 16-24 hrs. The combined culture from three flasks (600 ml) is then aseptically transferred to a 20 L fermentor (B. Braun Bioreactor Systems) containing 10 L of Dow proprietary defined medium (through Teknova, Hollister, Calif.) designed to support high cell density growth. Growth temperature is maintained at 32° C. and the pH is controlled at the desired set-point through the addition of aqueous ammonia. Dissolved oxygen will be maintained at a positive level in the liquid culture by regulating the sparged air flow and the agitation rates. The fed-batch fermentation process is carried out for approximately 24 hrs till cell density reaches 170-200 $OD_{575}$. IPTG is then added to 1 mM to induce the recombinant protein expression and the temperature is reduced and maintained at 25° C. using circulation of cold-water supply. The induction phase of the fermentation will be allowed to continue for another 24 hrs. Samples (30 ml) are collected for various analyses to determine cell density and protein expression level at 6, 12, and 18 hrs post-induction time points. At the end of a fermentation run, cells are harvested by centrifugation at 10 krpm for 30 min. The cell pellets are then frozen at −80° C. for further processing.

4.2—Purification of AAD-13 for Biochemical Characterization and Antibody Production Approximately 100-200 g of frozen (or fresh) *Pseudomonas* cells are thawed and resuspended in 1-2 L of extraction buffer containing 20 mM Tris-HCl, pH 8.5, and 25 ml of Protease inhibitor cocktail (Sigma cat#P8465). The cells are disrupted using Microfluidizer (model M110L or 110Y) (Microfluidics, Newton, Mass.) on ice with one pass at 11,000-12,000 psi. The lysate is centrifuged at 24,000 rpm for 20 min. The supernatant will be transferred and dialyzed against 10 volumes of 20 mM Tris-HCl, pH 8.5 overnight at 4° C., or diafiltrated with this buffer and filtered through a 0.45 µm membrane before applying to the column separations. All subsequent protein separations will be performed using Pharmacia AKTA Explorer 100 and operated at 4° C. Prior to loading, a Q Sepharose Fast Flow column (Pharmacia XK 50/00, 500 ml bed size) is equilibrated with 20 mM Tris-HCl, pH 8.5 buffer. The sample is applied to the column at 15 ml/min and then washed with this buffer until the eluate $OD_{280}$ returned to baseline. Proteins are eluted with 2 L of linear gradient from 0 to 0.3 M NaCl at a flow rate of 15 ml/min, while 45 ml fractions are collected. Fractions containing AAD-13 activity as determined by the colorimetric enzyme assay and also corresponding to the predicted molecular weight of AAD-13 protein (about 32 kDa band on SDS-PAGE) are to be pooled. Solid ammonium sulfate to final 0.5 M is added to the sample, and then applied to a Phenyl HP column (Pharmacia XK 50/20, 250 ml bed size) equilibrated in 0.5 M ammonium sulfate in 20 mM Tris-HCl, pH 8.0. This column is washed with the binding buffer at 10 ml/min until the $OD_{280}$ of the eluate returned to baseline, proteins are eluted within 2 column volumes at 10 ml/min by a linear gradient from 0.5 M to 0 Ammonium sulfate in 20 mM Tris-HCl, pH 8.0, and 12.5 ml fractions are collected. The main peak fractions containing AAD-13 will be pooled, and if necessary, concentrated using a MWCO 10 kDa cut-off membrane centrifugal filter device (Millipore). In some cases the sample is further applied to a Superdex 75 gel filtration column (Pharmacia XK 16/60, 110 ml bed size) with PBS buffer at a flow rate of 1 ml/min. Peak fractions containing pure AAD-13 are pooled and stored at −80° C. for future use.

Example 5

In Vitro Assays of AAD-13 Activity 5.1—Assay Via Colorimetric Phenol Detection.

Enzyme activity will be measured by colorimetric detection of the product phenol using a protocol modified from that of Fukumori and Hausinger (1993) (*J. Biol. Chem.* 268: 24311-24317) to enable deployment in a 96-well microplate format. The colorimetric assay has been described for use in measuring the activity of dioxygenases cleaving 2,4-D and dichlorprop to release the product 2,4-dichlorophenol. The color yield from several phenols was compared to that of 2,4-dichlorophenol using the detection method previously described to ascertain which phenol products could be readily detected. Phenols and phenol analogs were tested at a final concentration of 100 µM in 0.15 ml 20 mM MOPS pH 6.75 containing 200 µM $NH_4(FeSO_4)_2$, 200 µM sodium ascorbate. Pyridinols derived from fluoroxypyr and triclopyr produced no significant color. The color yield of 2,4-dichlorophenol was linear and proportional to the concentration of phenol in the assay up to ~500 µM. A calibration curve performed under standard assay conditions (160 µl final assay volume) indicated that an absorbance at 510 nm of 0.1 was obtained from 17.2 µM phenol.

Enzyme assays are performed in a total volume of 0.16 ml 20 mM MOPS pH 6.75 containing 200 µM $NH_4FeSO_4$, 200 µM sodium ascorbate, 1 mM α-ketoglutarate, the appropriate substrate (added from a 100 mM stock made up in DMSO), and enzyme. Assays are initiated by addition of the aryloxyalkanoate substrate, enzyme or α-ketoglutarate at time zero. After 5 minutes of incubation at 25° C., the reaction is terminated by addition of 30 µl of a 1:1:1 mix of 50 mM Na EDTA;

pH 10 buffer (3.09 g boric acid+3.73 g KCl+44 ml 1 N KOH) and 0.2% 4-aminoantipyrine. Then 10 µl 0.8% potassium ferricyanide is added and after 5 or 10 min, the absorbance at 510 nm was recorded in a spectrophotometric microplate reader. Blanks contained all reagents except for enzyme to account for the occasional slight contamination of some of the substrates by small amounts of phenols.

5.2—Assay Via Detection of Chloropyridinol

AAD-13 action on potential substrates such as the herbicide triclopyr containing a substituted pyridine (rather than benzene rings) will release a pyridinol on cleavage of the aryloxyalkanoate bond. Pyridinols were not detected using the aminoantipyrine/ferricyanide phenol detection described in the preceding section. However, it was found that product chloropyridinols absorb strongly in the near UV with $\lambda_{max}$ of 325 nm at pH 7 (extinction coefficient ~8,400 $M^{-1} \cdot cm^{-1}$). This was used to create a continuous microplate-based spectrophotometric assay. Assays are performed in a total volume of 0.2 ml 20 mM MOPS pH 6.75 containing 200 µM $NH_4FeSO_4$, 200 µM sodium ascorbate, 1 mM α-ketoglutarate, the appropriate substrate (added from a 100 mM stock made up in DMSO), and enzyme. Assays are initiated by addition of the aryloxyalkanoate substrate, enzyme or α-ketoglutarate at time zero and the increase in absorbance followed for 10 minutes at 325 nm in a microplate reader. The first 2 minutes of the reaction will be used to determine initial rates.

5.3—Colorimetric Assay Using 2-(2-chloro,4-nitrophenoxy)propionate

A convenient assay of AAD-13 was devised using 2-(2-chloro,4-nitrophenoxy)propionate (CNPP) as substrate. Cleavage of CNPP by AAD-13 will release 2-chloro,4-nitrophenol. This phenol has a bright yellow absorbance at 410 nm at pH 7 enabling the reaction to be followed continuously or by endpoint analysis. The presence of AAD-13 activity can be monitored visually without the need for addition of further reagents. Microplate-based spectrophotometric assays were performed in a total volume of 0.2 ml 20 mM MOPS pH 6.75 containing 200 µM $NH_4FeSO_4$, 200 µM sodium ascorbate, 1 mM α-ketoglutarate, the appropriate amount of CNPP (added from a 10 mM stock made up in DMSO), and enzyme. Assays are initiated by addition of CNPP, enzyme, or α-ketoglutarate at time zero and the increase in absorbance followed for 10 min at 410 nm in a microplate reader. The first 2 min of the reaction will be used to determine initial rates. A calibration curve performed under standard assay conditions (200 µl final assay volume) indicated that an absorbance at 410 nm of 0.1 was obtained from 25.1 µM 2-chloro, 4-nitrophenol. Using this assay, the kinetic constants for CNPP as a substrate were determined to be $K_m=31\pm5.5$ µM and $k_{cat}=16.2\pm0.79$ $min^{-1}$.

5.4—Coupled Assay

Figure 3:
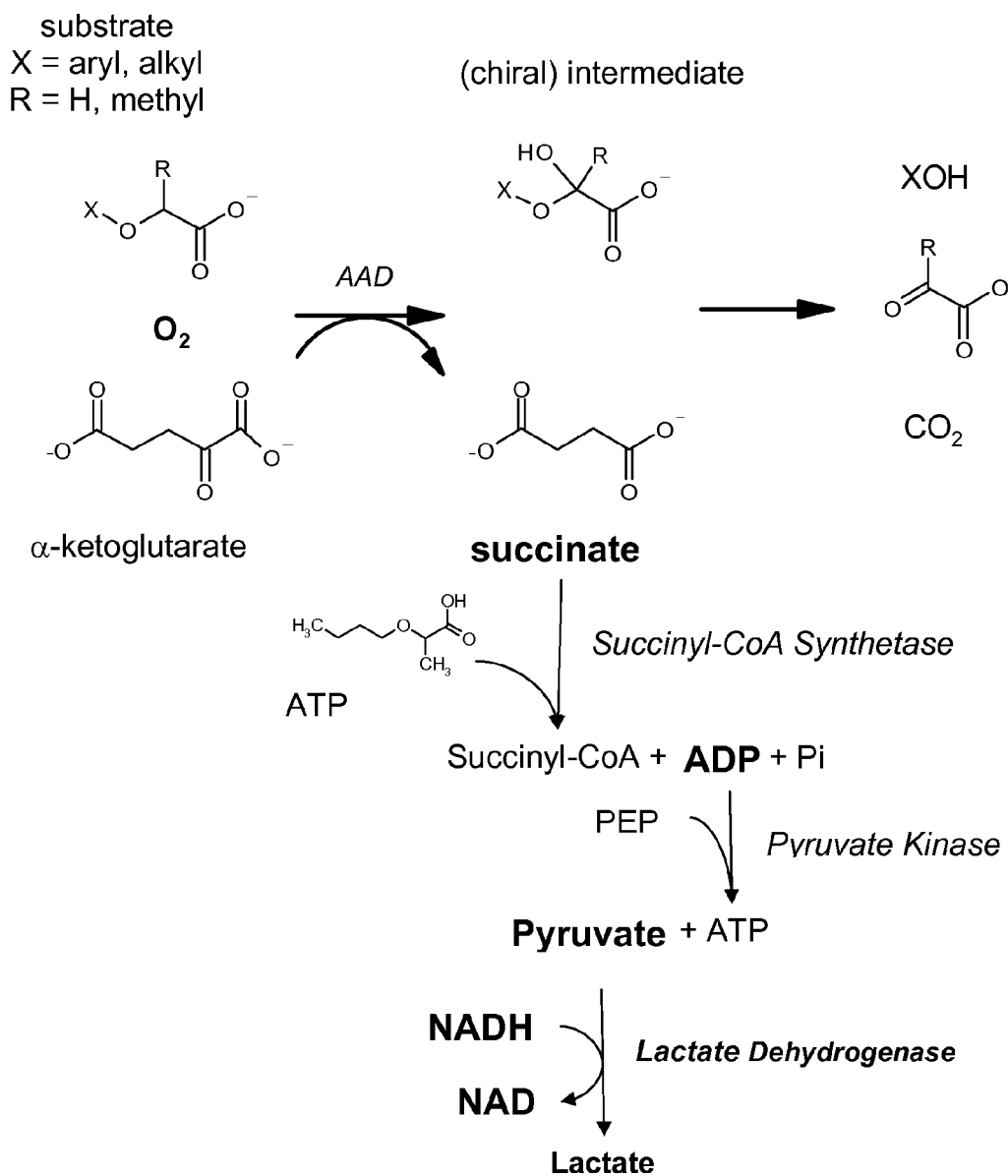
FIG. 3 illustrates the concomitant breakdown of α-ketoglutarate and the substrate of interest via AAD-13.

In order to test a broad range of substrates, the production of succinate from the breakdown of α-ketoglutarate was detected spectrophotometricly using a protocol based on the method of Luo et. al. (2006) (*Anal. Biochem.* 353: 69-74). As depicted in FIG. 3, the concomitant breakdown of α-ketoglutarate and the substrate of interest via AAD-13, results in the production of succinate. Succinate is further modified to succinyl-CoA by succinyl-CoA synthetase which consumes ATP and produces ADP. ADP is then consumed by the commonly employed pyruvate kinase/lactate dehydrogenase enzymatic coupling system (Sigma P0294). The resulting conversion of NADH to NAD is monitored spectrophotometrically at 340 nm.

5.4.1—Cloning and Expression of His-Tagged Succinyl-CoA Synthetase and AAD-13 (v2)

The two *E. coli* genes that encode the synthetase, sucC and sucD, were amplified out of the Top10 strain of *E. coli* from Invitrogen as a single amplicon. Genomic DNA was obtained by boiling an aliquot of cells for 10 min, then centrifuging, and retaining the supernatant containing the DNA. As template for AAD-13 (v2), the previously created pET clone pDAB4115 was used. To amplify the sucCD genes, the following primers were used: suc-Nde (SEQ ID 9) 5' CATATGAACTTACATGAATATCAGGCAAAAC 3' and suc-Xho (SEQ ID 10) 5' CTCGAGTTTCAGAACAGTTTTCAGTGCTTC 3'. For AAD-13 (v2), the following primers were used: aad-13F (SEQ ID 11) 5' CATATGGCGAGCCCGGCG 3' and aad-13R (SEQ ID 12) 5' CTCGAGGTGTGCCAGTGCGGTCTC 3'. These add suitable restriction sites for downstream cloning and remove the stop codon to permit His-tagging. For the reaction, thermal cycler conditions were: 96° C. 2 min, then 35 cycles of: 96° C. 30 sec, 53° C. 30 sec, 72° C. 1.5 min, followed by a one final cycle of 72° C. 5 min. The resulting amplicons were sub-cloned to verify correct sequence. Clones for each containing the correct insert were digested with Nde1/Xho1 and the inserts were then cloned into the pET-26b(+) expression vector. For expression, a lawn of transformed BL-21 *E. coli* was scraped into 50 ml of LB+Kan (50 ng/ml) and grown at 37° C. for 2 hrs. Two milliliters of this culture were transferred into 100 ml of LB+Kan. These flasks were grown at 37° C. for 4 hrs. Cells were induced with 50 µM IPTG, and grown overnight at 25° C. Cultures were centrifuged, and cell pellet used for protein purification.

5.4.2—Purification of AAD-13 and His-Tagged Succinyl CoA Synthetase for In Vitro Substrate Identification His-tagged AAD-13 was purified using metal affinity chromatography protocols based on the column manufacturer's directions. Cell pellets harvested from 1 L of culture and stored at −80° C. were thawed and resuspended in 20 mL of extraction buffer (100 mM Tris-HCl, pH 8; 200-300 µL protease inhibitor cocktail (Sigma P8849), 1 mg/mL lysozyme, and 1 mM $MgCl_2$). Resuspended cells incubated at room temperature for 10-15 min prior to treating with DNase to reduce viscosity. All subsequent steps were carried out at 4° C. The extract was centrifuged for 20 min at 20,000×g to clarify. Using a flow rate of 1 mL/min, the resulting supernatant was applied to 2 consecutive 1 mL Co-MAC™ Cartridges (EMD/Novagen 71650) previously equilibrated with buffer A (25 mM Tris pH 8.0, 0.5 M NaCl). After the extract was loaded, the column was washed with 5 mM imidazole in buffer A until the $OD_{280}$ returned to baseline. Protein was eluted with 50 mM imidazole in buffer A. Fractions containing predominantly AAD-13 as indicated by an approximately 30 kDa band on SDS-PAGE were exchanged into buffer C (20 mM Tris pH 8.0, 100 mM NaCl, 2 mM DTT) using BG-10 desalting columns (Bio-Rad). AAD-13 in buffer C was then assayed spectrophotometrically according to the in vitro coupled assay.

His-tagged succinyl CoA synthetase was purified utilizing consecutive 1 mL Co-MAC™ Cartridges (EMD/Novagen 71650) and protocols based on the manufacturer's directions. Cell pellets that had been stored at −80° C. were thawed and resuspended in 50 mL of extraction buffer (100 mM Tris pH 7.2, 200-300 µL protease inhibitor cocktail (Sigma P8849), 1 mg/mL lysozyme, and 1 mM $MgCl_2$) per L of cell culture. Resuspended cells were incubated at room temperature for 10-15 min prior to treating with DNase to reduce viscosity. All subsequent steps were carried out at 4° C. unless noted otherwise. The extract was centrifuged for 20 min at 20,000×g to clarify. At this point, supernatant can either be applied directly to Co-MAC™ Cartridges pre-equilibrated with binding buffer (0.5M NaCl, 20 mM Tris-HCl pH 7.9 and 5 mM imidazole) or brought to 80% ammonium sulfate. The ammonium sulfate treated sample was centrifuged for 20 min at 20,000×g to pellet protein. Pellet was resuspended in buffer A (20 mM Tris-HCl pH 8.0 and 0.5M NaCl) and residual ammonium sulfate was removed using BG-10 desalting columns (Bio-Rad) pre-equilibrated with buffer A. The resulting samples were applied to Co-MAC™ Cartridges pre-equilibrated with binding buffer and a flow rate of 1 mL/min. Following application of extracted protein, column was rinsed with 10 column volumes of 0.5% buffer B (20 mM Tris-HCl, 0.5M NaCl, and 1 M imidazole). This was followed by a 5 column volume step gradient of 6% buffer B and an additional 10 column volume step gradient of 50% buffer B. The majority of the desired protein eluted with the 6% buffer B gradient. Fractions containing succinyl CoA synthetase were identified by the presence of two bands corresponding to the succinyl CoA synthetase subunits (~40 & 33 kDa) via SDS PAGE and the detection of corresponding in vitro activity. Succinyl CoA synthetase activity was confirmed using a modified version of the in vitro coupled assay below. Briefly, reaction progress was monitored spectrophotometrically at 340 nm in the presence of 100 mM tris pH 8.0, 1 mM PEP 0.4 mM NADH 10 mM $MgCl_2$, 0.2 mM CoA, 0.2 mM ATP, 3.5 U/mL PK, 5 U/mL LDH, and SCS. Reaction was initiated by the addition of 1 mM succinate.

5.4.3—In Vitro Coupled Assay

Identification of AAD-13 (v2) substrates in vitro was based on enzymatic activity detected during continuous spectrophotometric monitoring of a 0.2 mL reaction volume in a 96 well microtiter plate. Reaction conditions were as follows: 100 mM MOPS pH 7.0, 0.4 mM NADH, 0.4 mM ATP, 0.4 mM CoA, 1 mM PEP, 10 mM $MgCl_2$, 0.1 mM $FeSO_2$ (solubilized in HCl), and 0.1 mM ascorbate, 1 mM α-ketoglutarate and sufficient AAD-13 (v2) to produce an observable rate in the presence of 2,4-D. Coupling enzymes (SCS/PK/LDH) were adjusted by batch to ensure adequate coupling, and potential substrates were generally assayed at 1 mM. Alterations in substrate concentrations were made as needed to adjust for solubility. Reactions were initiated by either the addition of AAD-13 (v2) or potential substrate. The rate of substrate independent conversion of α-ketoglutarate to succinate by AAD was monitored under the above assay conditions and subtracted from the observed reaction rates. Reaction rates observed with propionate substrates were divided by two to adjust for the production of pyruvate resulting from the cleavage of these compounds via AAD. Additionally, propionate compounds were checked for pyruvate contamination by spectrophotometrically monitoring the consumption of NADH in the presence of compound and PK/LDH.

5.4.4 In Vitro Screening Results

Table Ex5 displays the AAD-13 (v2) reaction rate observed with multiple chemistries via the in vitro coupled assay. Reaction rates are reported as a percentage of the 2,4-D reaction rate obtained in the same sample set. This data can be used to qualitatively segregate substrates from non-substrates, as well as identify trends in substrate efficiency. It should be noted that faster rates can be more difficult to accurately compare depending on the percentage of available substrate consumed. This is particularly true of propionate compounds which display twice the rate as non-propionate compounds for the equivalent number of enzyme turnovers. As a result, highly efficient substrates will be properly grouped when compared to low efficiency substrates. Within the grouping of highly efficient substrates however, compounds may not be quantitatively separated by a screen using single rates of substrate and AAD. Compounds denoted with an asterisk were tested at 0.5 mM instead of 1 mM due to absorbance interference at higher concentrations.

TABLE EX5

| Name | X# | substrate Y/N | % of 24D activity | MOL. STRUCTURE |
|------|-----|---------------|-------------------|----------------|
|      | 191716 | y | 66 | |
|      | 571320 | y | 39 | |
|      | 93116 | y | 128 | |
|      | 475726 | y | 112 | |

TABLE EX5-continued
| Name | X# | substrate Y/N | % of 24D activity | MOL. STRUCTURE |
|---|---|---|---|---|
| | 118942 | y | 46 | 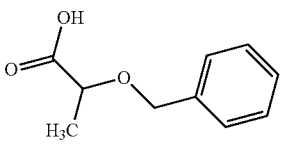 |
| | 470901 | y | 30 | 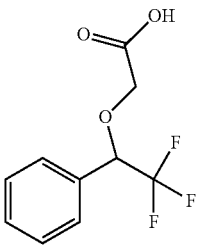 [SMILES: O=C(O)COC(c1ccccc1)C(F)(F)F] |
| R-fenoxaprop | 11044492 | N | 2 | 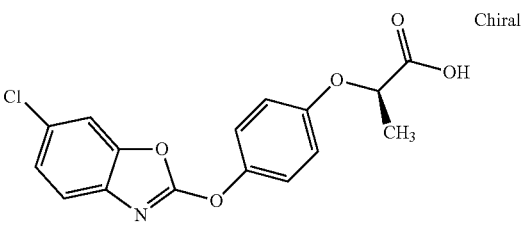 [SMILES: C[C@@H](Oc1ccc(Oc2nc3ccc(Cl)cc3o2)cc1)C(=O)O] Chiral |
| Mecoprop | 188874 | y | 169 | 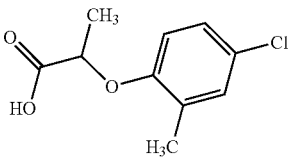 |
| r dichlorprop | | | 19 | |
| r,s dichlorprop | 117613 | Y | 195 | 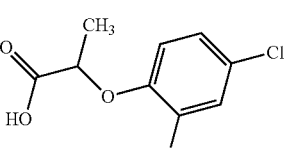 |
| S-dichlorprop | | y | 233 | |
| 2,4-D | 195517 | y | 100 | 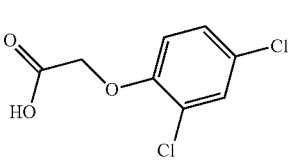 [SMILES: O=C(O)COc1ccc(Cl)cc1Cl] |
| 24DB | 178577 | N | 2 | 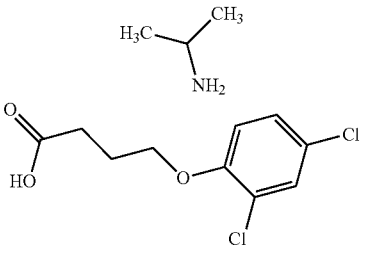 |

TABLE EX5-continued

| Name | X# | substrate Y/N | % of 24D activity | MOL. STRUCTURE |
|---|---|---|---|---|
| 3-amino 24D | 11263526 | y | 151 | |
| | 11113675 | y | 113 | |
| | 124988 | y | 44 | |
| | 83293 | y | 106 | |
| alpha methyl floroxypyr | 11182286 | y | 43 | |
| fluoroxypyr | 68316 | y | 67 | |
| triclopyr | 156136 | N | 6 | |
| | 93833 | y | 33 | |

TABLE EX5-continued

| Name | X# | substrate Y/N | % of 24D activity | MOL. STRUCTURE |
|---|---|---|---|---|
| | 66357 | y | 24 | |
| | 91767 | y | 88 | |
| | 116844 | y | 25 | |
| diclofop | 460511 | y | >100 | |
| fluazifop | 67131 | y | ~50 | |
| quizalofop | 44936* | Y | | |
| cyhalofop | 7466 | y | | |
| | 66732 | y | >100 | |

TABLE EX5-continued

| Name | X# | substrate Y/N | % of 24D activity | MOL. STRUCTURE |
|---|---|---|---|---|
| | 8563 | y | 64 | |
| | 193908 | y | 56 | |
| | 761310* | | Not Detected | |
| | 11077344* | | Not Detected | |
| | 198167 | | Not Detected | |
| | 11077347* | | Not Detected | |
| | 238166* | | Not Detected | |
| | 657338 | N | 5 | |

TABLE EX5-continued

| Name | X# | substrate Y/N | % of 24D activity | MOL. STRUCTURE |
|------|-----|---|---|---|
| | 657339 | N | 5 | |
| | 11213586 | N | 2 | |
| | 11453845 | N | 13 | |
| | 187507 | N | 10 | |
| | 204558* | | Not Detected | |
| | 188495 | M | 19 | |

TABLE EX5-continued

| Name | X# | substrate Y/N | % of 24D activity | MOL. STRUCTURE |
|------|-----|---|---|---|
| | 187439 | | Not Detected | 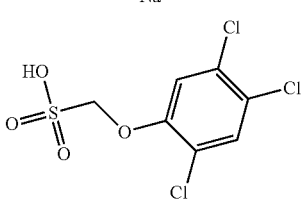 |
| | 1190305 | | Not Detected | 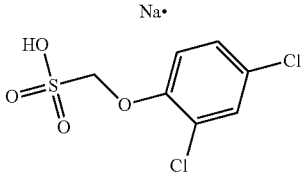 |

AAD-13 is unlike other reported α-ketoglutarate-dependent dioxygenases who have 2,4-D-degrading activity. A key distinction is the broad array of aryloxy and alkyloxy-alkanoate substrates, but a number of pyridyloxysubstitutes are effective herbicides and substrates (e.g., fluoroxypyr) but other herbicides like triclopyr are considerably poorer substrates. This creates a new opportunity to use alternative herbicides for control of transgenic plants with AAD-13 substrates. It also provides opportunity to complement similar genes in planta to broaden tolerance or improve the breadth of substrates to which the plants are tolerant.

Example 6

Transformation into *Arabidopsis* and Selection 6.1—*Arabidopsis thaliana* Growth Conditions.

Wildtype *Arabidopsis* seed was suspended in a 0.1% Agarose (Sigma Chemical Co., St. Louis, Mo.) solution. The suspended seed was stored at 4° C. for 2 days to complete dormancy requirements and ensure synchronous seed germination (stratification).

Sunshine Mix LP5 (Sun Gro Horticulture, Bellevue, Wash.) was covered with fine vermiculite and sub-irrigated with Hoagland's solution until wet. The soil mix was allowed to drain for 24 hours. Stratified seed was sown onto the vermiculite and covered with humidity domes (KORD Products, Bramalea, Ontario, Canada) for 7 days.

Seeds were germinated and plants were grown in a Conviron (models CMP4030 and CMP3244, Controlled Environments Limited, Winnipeg, Manitoba, Canada) under long day conditions (16 hours light/8 hours dark) at a light intensity of 120-150 µmol/m²sec under constant temperature (22° C.) and humidity (40-50%). Plants were initially watered with Hoagland's solution and subsequently with deionized water to keep the soil moist but not wet.

6.2—*Agrobacterium* Transformation.

An LB+agar plate with erythromycin (Sigma Chemical Co., St. Louis, Mo.) (200 mg/L) or spectinomycin (100 mg/L) containing a streaked DH5α colony was used to provide a colony to inoculate 4 ml mini prep cultures (liquid LB+erythromycin). The cultures were incubated overnight at 37° C. with constant agitation. Qiagen (Valencia, Calif.) Spin Mini Preps, performed per manufacturer's instructions, were used to purify the plasmid DNA.

Electro-competent *Agrobacterium tumefaciens* (strains Z707s, EHA101s, and LBA4404s) cells were prepared using a protocol from Weigel and Glazebrook (2002). The competent *Agrobacterium* cells were transformed using an electroporation method adapted from Weigel and Glazebrook (2002). 50 µl of competent agro cells were thawed on ice, and 10-25 ng of the desired plasmid was added to the cells. The DNA and cell mix was added to pre-chilled electroporation cuvettes (2 mm) An Eppendorf Electroporator 2510 was used for the transformation with the following conditions, Voltage: 2.4 kV, Pulse length: 5 msec.

After electroporation, 1 ml of YEP broth (per liter: 10 g yeast extract, 10 g Bacto-peptone, 5 g NaCl) was added to the cuvette, and the cell-YEP suspension was transferred to a 15 ml culture tube. The cells were incubated at 28° C. in a water bath with constant agitation for 4 hours. After incubation, the culture was plated on YEP+agar with erythromycin (200 mg/L) or spectinomycin (100 mg/L) and streptomycin (Sigma Chemical Co., St. Louis, Mo.) (250 mg/L). The plates were incubated for 2-4 days at 28° C.

Colonies were selected and streaked onto fresh YEP+agar with erythromycin (200 mg/L) or spectinomycin (100 mg/L) and streptomycin (250 mg/L) plates and incubated at 28° C. for 1-3 days. Colonies were selected for PCR analysis to verify the presence of the gene insert by using vector specific primers. Qiagen Spin Mini Preps, performed per manufacturer's instructions, were used to purify the plasmid DNA from selected *Agrobacterium* colonies with the following exception: 4 ml aliquots of a 15 ml overnight mini prep culture (liquid YEP+erythromycin (200 mg/L) or spectinomycin (100 mg/L)) and streptomycin (250 mg/L)) were used for the DNA purification. An alternative to using Qiagen Spin Mini Prep DNA was lysing the transformed *Agrobacterium* cells, suspended in 10 µl of water, at 100° C. for 5 minutes. Plasmid DNA from the binary vector used in the *Agrobacterium* transformation was included as a control. The PCR reaction was completed using Taq DNA polymerase from Takara Minis Bio Inc. (Madison, Wis.) per manufacturer's instructions at 0.5× concentrations. PCR reactions were carried out in a MJ Research Peltier Thermal Cycler programmed with the following conditions; 1) 94° C. for 3 minutes, 2) 94° C. for 45 seconds, 3) 55° C. for 30 seconds, 4) 72° C. for 1 minute, for 29 cycles then 1 cycle of 72° C. for 10 minutes. The reaction was maintained at 4° C. after cycling. The amplification was analyzed by 1% agarose gel electrophoresis and visualized by ethidium bromide staining. A colony was selected whose PCR product was identical to the plasmid control.

6.3—*Arabidopsis* Transformation.

*Arabidopsis* was transformed using the floral dip method. The selected colony was used to inoculate one or more 15-30 ml pre-cultures of YEP broth containing erythromycin (200 mg/L) or spectinomycin (100 mg/L) and streptomycin (250 mg/L). The culture(s) was incubated overnight at 28° C. with constant agitation at 220 rpm. Each pre-culture was used to inoculate two 500 ml cultures of YEP broth containing erythromycin (200 mg/L) or spectinomycin (100 mg/L) and streptomycin (250 mg/L) and the cultures were incubated overnight at 28° C. with constant agitation. The cells were then pelleted at approx. 8700×g for 10 minutes at room temperature, and the resulting supernatant discarded. The cell pellet was gently resuspended in 500 ml infiltration media containing: ½× Murashige and Skoog salts/Gamborg's B5 vitamins, 10% (w/v) sucrose, 0.044 µM benzylamino purine (10 µl/liter of 1 mg/ml stock in DMSO) and 300 µl/liter Silwet L-77. Plants approximately 1 month old were dipped into the media for 15 seconds, being sure to submerge the newest inflorescence. The plants were then laid down on their sides and covered (transparent or opaque) for 24 hours, then washed with water, and placed upright. The plants were grown at 22° C., with a 16-hour light/8-hour dark photoperiod. Approximately 4 weeks after dipping, the seeds were harvested.

6.4—Selection of Transformed Plants.

Freshly harvested $T_1$ seed [AAD-13 (v1) gene] was allowed to dry for 7 days at room temperature. $T_1$ seed was sown in 26.5×51-cm germination trays (T.O. Plastics Inc., Clearwater, Minn.), each receiving a 200 mg aliquots of stratified $T_1$ seed (~10,000 seed) that had previously been suspended in 40 ml of 0.1% agarose solution and stored at 4° C. for 2 days to complete dormancy requirements and ensure synchronous seed germination.

Sunshine Mix LP5 (Sun Gro Horticulture Inc., Bellevue, Wash.) was covered with fine vermiculite and subirrigated with Hoagland's solution until wet, then allowed to gravity drain. Each 40 ml aliquot of stratified seed was sown evenly onto the vermiculite with a pipette and covered with humidity domes (KORD Products, Bramalea, Ontario, Canada) for 4-5 days. Domes were removed 1 day prior to initial transformant selection using glufosinate postemergence spray (selecting for the co-transformed PAT gene).

Seven days after planting (DAP) and again 11 DAP, $T_1$ plants (cotyledon and 2-4-lf stage, respectively) were sprayed with a 0.2% solution of Liberty herbicide (200 g ai/L glufosinate, Bayer Crop Sciences, Kansas City, Mo.) at a spray volume of 10 ml/tray (703 L/ha) using a DeVilbiss compressed air spray tip to deliver an effective rate of 280 g ai/ha glufosinate per application. Survivors (plants actively growing) were identified 4-7 days after the final spraying and transplanted individually into 3-inch pots prepared with potting media (Metro Mix 360). Transplanted plants were covered with humidity domes for 3-4 days and placed in a 22° C. growth chamber as before or moved to directly to the greenhouse. Domes were subsequently removed and plants reared in the greenhouse (22±5° C., 50±30% RH, 14 h light:10 dark, minimum 500 µE/m²s¹ natural+supplemental light) at least 1 day prior to testing for the ability of AAD-13 (v1) to provide phenoxy auxin herbicide resistance.

$T_1$ plants were then randomly assigned to various rates of 2,4-D. For *Arabidopsis,* 50 g ae/ha 2,4-D is an effective dose to distinguish sensitive plants from ones with meaningful levels of resistance. Elevated rates were also applied to determine relative levels of resistance (280, 560, 1120, or 2240 g ae/ha). Tables 11 and 12 show comparisons drawn to an aryloxyalkanoate herbicide resistance gene (AAD-12 (v1)) previously described in PCT/US2006/042133.

All auxin herbicide applications were made using the DeVilbiss sprayer as described above to apply 703 L/ha spray volume (0.4 ml solution/3-inch pot) or applied by track sprayer in a 187 L/ha spray volume. 2,4-D used was either technical grade (Sigma, St. Louis, Mo.) dissolved in DMSO and diluted in water (<1% DMSO final concentration) or the commercial dimethylamine salt formulation (456 g ae/L, NuFarm, St Joseph, Mo.). Dichlorprop used was commercial grade formulated as potassium salt of R-dichlorprop (600 g ai/L, AH Marks). As herbicide rates increased beyond 800 g ae/ha, the pH of the spray solution became exceedingly acidic, burning the leaves of young, tender *Arabidopsis* plants and complicating evaluation of the primary effects of the herbicides.

Some $T_1$ individuals were subjected to alternative commercial herbicides instead of a phenoxy auxin. One point of interest was determining whether the pyridyloxyacetate auxin herbicides, triclopyr and fluoroxypyr, could be effectively degraded in planta. Herbicides were applied to $T_1$ plants with use of a track sprayer in a 187 L/ha spray volume. $T_1$ plants that exhibited tolerance to 2,4-D DMA were further accessed in the $T_2$ generation.

6.5—Results of Selection of Transformed Plants.

The first *Arabidopsis* transformations were conducted using AAD-13 (v1) (plant optimized gene). $T_1$ transformants were first selected from the background of untransformed seed using a glufosinate selection scheme. Over 160,000 $T_1$ seed were screened and 238 glufosinate resistant plants were identified (PAT gene), equating to a transformation/selection frequency of 0.15% which lies in the normal range of selection frequency of constructs where PAT+Liberty are used for selection. $T_1$ plants selected above were subsequently transplanted to individual pots and sprayed with various rates of commercial aryloxyalkanoate herbicides. Table 11 compares the response of AAD-13 (v1) and control genes to impart 2,4-D resistance to *Arabidopsis* $T_1$ transformants. Response is presented in terms of % visual injury 2 WAT. Data are presented as a histogram of individuals exhibiting little or no injury (<20%), moderate injury (20-40%), or severe injury (>40%). An arithmetic mean and standard deviation is presented for each treatment. The range in individual response is also indicated in the last column for each rate and transformation. PAT/Cry1F-transformed *Arabidopsis* served as an auxin-sensitive transformed control. The AAD-13 (v1) gene imparted herbicide resistance to individual $T_1$ *Arabidopsis* plants. Within a given treatment, the level of plant response varied greatly and can be attributed to the fact each plant represents an independent transformation event. Of important note, at each 2,4-D rate tested, there were individuals that were unaffected while some were severely affected. An overall population injury average by rate is presented in Table 11 simply to demonstrate the significant difference between the plants transformed with AAD-13 (v1) versus the AAD-12 (v1) or PAT/Cry1F-transformed controls. At high rates the spray solution becomes highly acidic unless buffered therefore some of the injury may be attributed to the acidity of the spray solution. *Arabidopsis* grown mostly in the growth chamber has a very thin cuticle and severe burning effects can complicate testing at these elevated rates. Nonetheless, many individuals have survived 2,240 g ae/ha 2,4-D with little or no injury.

TABLE 11

AAD-13 (v1) transformed T1 *Arabidopsis* response to a range of 2,4-D rates applied postemergence, compared to an AAD-12 v1 (T4) homozygous resistant population, or a Pat-Cry1F transformed, auxin-sensitive control (14 DAT).

| Averages | % Injury <20% | % Injury 20-40% | % Injury >40% | Ave | Std dev | Range (%) |
|---|---|---|---|---|---|---|
| AAD-13 (v1) gene $T_1$ plants | | | | | | |
| 0 g ae/ha 2,4-D DMA | 20 | 0 | 0 | 0 | 0 | 0 |
| 280 g ae/ha 2,4-D DMA | 12 | 4 | 4 | 21 | 31 | 0-90 |
| 560 g ae/ha 2,4-D DMA | 17 | 2 | 0 | 2 | 6 | 0-20 |
| 1120 g ae/ha 2,4-D DMA | 20 | 0 | 0 | 2 | 4 | 0-10 |
| 2240 g ae/ha 2,4-D DMA | 14 | 3 | 3 | 15 | 23 | 0-70 |
| PAT/Cry1F (transformed control) | | | | | | |
| 0 g ae/ha 2,4-D DMA | 20 | 0 | 0 | 0 | 0 | 0 |
| 280 g ae/ha 2,4-D DMA | 0 | 0 | 20 | 100 | 0 | 100 |
| 560 g ae/ha 2,4-D DMA | 0 | 0 | 20 | 100 | 0 | 100 |
| 1120 g ae/ha 2,4-D DMA | 0 | 0 | 20 | 100 | 0 | 100 |
| 2240 g ae/ha 2,4-D DMA | 0 | 0 | 20 | 100 | 0 | 100 |
| Homozygous AAD-12 (v1) gene $T_4$ plants | | | | | | |
| 0 g ae/ha 2,4-D DMA | 20 | 0 | 0 | 0 | 0 | 0 |
| 280 g ae/ha 2,4-D DMA | 20 | 0 | 0 | 0 | 0 | 0 |
| 560 g ae/ha 2,4-D DMA | 20 | 0 | 0 | 1 | 3 | 0-10 |
| 1120 g ae/ha 2,4-D DMA | 20 | 0 | 0 | 2 | 4 | 0-15 |
| 2240 g ae/ha 2,4-D DMA | 16 | 3 | 1 | 13 | 13 | 0-50 |

Table 12 shows a similarly conducted dose response of $T_1$ *Arabidopsis* to the phenoxypropionic acid, dichlorprop. The data shows that the herbicidally active (R-) isomer of dichlorprop does not serve as a suitable substrate for AAD-13 (v1) or AAD-12 (v1). The fact that AAD-1 (v3) will metabolize R-dichlorprop well enough to impart commercially acceptable tolerance is one distinguishing characteristic that separates the three genes (Table 12 and Example 7 of PCT/US2006/042133 (Wright et al., filed Oct. 27, 2006). AAD-1 and AAD-13 are considered R- and S-specific α-ketoglutarate dioxygenases, respectively.

TABLE 12

T1 *Arabidopsis* response to a range of R-dichlorprop rates applied postemergence. (14 DAT)

| Averages | % Injury <20% | % Injury 20-40% | % Injury >40% | Ave | Std dev | Range (%) |
|---|---|---|---|---|---|---|
| AAD-13 (v1) gene $T_1$ plants | | | | | | |
| 0 g ae/ha | 20 | 0 | 0 | 0 | 0 | 0 |
| 800 g ae/ha R-dichloroprop | 0 | 0 | 20 | 100 | 0 | 100 |
| Wildtype (untransformed control) | | | | | | |
| 0 g ae/ha | 20 | 0 | 0 | 0 | 0 | 0 |
| 800 g ae/ha R-dichloroprop | 0 | 0 | 20 | 100 | 0 | 100 |
| Homozygous AAD-12 (v1) gene $T_4$ plants | | | | | | |
| 0 g ae/ha | 20 | 0 | 0 | 0 | 0 | 0 |
| 800 g ae/ha R-dichloroprop | 0 | 0 | 20 | 100 | 0 | 100 |

6.6—AAD-13 (v1) as a Selectable Marker.

The ability to use AAD-13 (v1) as a selectable marker using 2,4-D as the selection agent will be was analyzed with *Arabidopsis* transformed as described above. Approximately 50 $T_4$ generation *Arabidopsis* seed (homozygous for AAD-13 (v1)) will be spiked into approximately 5,000 wildtype (sensitive) seed. Several treatments will be compared, each tray of plants will receive either one or two application timings of 2,4-D in one of the following treatment schemes: 7 DAP, 11 DAP, or 7 followed by 11 DAP. Since all individuals also contain the PAT gene in the same transformation vector, AAD-13 selected with 2,4-D can be directly compared to PAT selected with glufosinate.

Treatments will be applied with a DeVilbiss spray tip as previously described. Plants will be identified as Resistant or Sensitive 17 DAP. The optimum treatment of 75 g ae/ha 2,4-D applied 7 and 11 days after planting (DAP), is equally effective in selection frequency, and results in less herbicidal injury to the transformed individuals than the Liberty selection scheme. These results will indicate that AAD-13 (v1) can be effectively used as an alternative selectable marker for a population of transformed *Arabidopsis*.

6.7—Heritability.

A variety of $T_1$ events were self-pollinated to produce $T_2$ seed. These seed were progeny tested by applying Liberty (280 g ae/ha) to 100 random $T_2$ siblings. Each individual $T_2$ plant was transplanted to 7.5-cm square pots prior to spray application (track sprayer at 187 L/ha applications rate). Fifty percent of the $T_1$ families ($T_2$ plants) segregated in the anticipated 3 Resistant:1 Sensitive model for a dominantly inherited single locus with Mendelian inheritance as determined by Chi square analysis (P>0.05).

Seed were collected from 12 to 20 $T_2$ individuals ($T_3$ seed). Twenty-five $T_3$ siblings from each of eight randomly-selected $T_2$ families were progeny tested as previously described. Half of the $T_2$ families tested were homozygous (non-segregating populations) in each line. These data show will show that AAD-13 (v1) is stably integrated and inherited in a Mendelian fashion to at least three generations.

6.8—Additional Foliar Applications Herbicide Resistance in AAD-13 *Arabidopsis*.

The ability of AAD-13 (v1) to provide resistance to other aryloxyalkanoate auxin herbicides in transgenic *Arabidopsis* was determined by foliar application of various substrates. $T_2$ generation *Arabidopsis* seed was stratified, and sown into selection trays much like that of *Arabidopsis* (Example 6.4). A transformed-control line containing PAT and the insect resistance gene Cry1F was planted in a similar manner. Seedlings were transferred to individual 3-inch pots in the greenhouse. All plants were sprayed with the use of a track sprayer set at 187 L/ha. The plants were sprayed with a range of pyridyloxyacetate herbicides: 200-800 g ae/ha triclopyr (Garlon 3A, Dow AgroSciences) and 200-800 g ae/ha fluroxypyr (Starane, Dow AgroSciences). The 2,4-D metabolite resulting from AAD-13 activity, 2,4-dichlorophenol (DCP, Sigma) (at a molar equivalent to 280-2240 g ae/ha of 2,4-D, technical grade will also be tested. All applications were formulated in water. Each treatment was replicated 3-4 times. Plants were evaluated at 3 and 14 days after treatment.

AAD-13-transformed plants were also clearly protected from the fluroxypyr herbicide injury that was seen in the transformed control line, Pat/Cry1F (see Table 13); however, AAD-13-transformed plants were severely injured by triclopyr. These results confirm that AAD-13 (v1) in *Arabidopsis* provides resistance to the pyridyloxyacetic auxins tested. The AAD-13 (v1) gene provided robust resistance up to 400 g ae/ha fluroxypyr, whereas the AAD-12 (v1) gene provided only modest level of tolerance as low as 200 g/ha. The AAD-13 (v1) gene provided significantly less tolerance to triclopyr than the AAD-12 (v1) gene. The significantly greater tolerance to fluroxypyr is unexpected and allows distinction of AAD-13 (v1)-type activity from AAD-12 (v1) and is supported by the enzymatic data of Example 5.

TABLE 13

Comparison of T2 AAD-13 (v1) and transformed control *Arabidopsis* plant response to various foliar-applied auxinic herbicides.
Pyridyloxyacetic auxins

| | Ave. % Injury 14DAT | | |
|---|---|---|---|
| Herbicide Treatment | Segregating T2 AAD-13 (v1) plants (pDAB4114.01.094) | Homozygous T4 AAD-12 (v1) plants | Pat/Cry1f-Control |
| 200 g ae/ha triclopyr | 75 | 25 | 100 |
| 400 g ae/ha triclopyr | 90 | 33 | 100 |
| 800 g ae/ha triclopyr | 100 | 79 | 100 |

TABLE 13-continued

Comparison of T2 AAD-13 (v1) and transformed control *Arabidopsis* plant response to various foliar-applied auxinic herbicides.
Pyridyloxyacetic auxins

| | Ave. % Injury 14DAT | | |
|---|---|---|---|
| Herbicide Treatment | Segregating T2 AAD-13 (v1) plants (pDAB4114.01.094) | Homozygous T4 AAD-12 (v1) plants | Pat/Cry1f-Control |
| 200 g ae/ha fluroxypyr | 10 | 48 | 100 |
| 400 g ae/ha fluroxypyr | 16 | 55 | 100 |
| 800 g ae/ha fluroxypyr | 55 | 60 | 100 |

Example 7

Transformation of Additional Crop Species

Corn may be transformed to provide high levels resistance to 2,4-D and fluroxypyr by utilizing the same techniques previously described in Example #8 of WO 2007/053482 (PCT/US2006/042133 (Wright et al.).

Soybean may be transformed to provide high levels resistance to 2,4-D and fluroxypyr by utilizing the same techniques previously described in Example #11 or Example #13 of WO 2007/053482 (PCT/US2006/042133 (Wright et al.)).

Cotton may be transformed to provide high levels resistance to 2,4-D and fluroxypyr by utilizing the same techniques previously described in Examples #14 of patent application PCT/US2005/014737 (Wright et al., filed May 2, 2005) or Example #12 of WO 2007/053482 (Wright et al.).

Canola may be transformed to provide high levels resistance to 2,4-D and fluroxypyr by utilizing the same techniques previously described in Example #26 of patent application PCT/US2005/014737 (Wright et al., filed May 2, 2005) or Example #22 of WO 2007/053482 (Wright et al.).

Example 8

Protein Detection from Transformed Plants Via Antibody

Antibodies and subsequent ELISA assays can be developed and implemented as described in Example 9 of WO 2007/053482 (Wright et al.), for example.

Example 9

Tobacco Transformation

Tobacco transformation with *Agrobacterium tumefaciens* was carried out by a method similar, but not identical, to published methods (Horsch et al., 1988). To provide source tissue for the transformation, tobacco seed (*Nicotiana tabacum* cv. KY160) was surface sterilized and planted on the surface of TOB-medium, which is a hormone-free Murashige and Skoog medium (Murashige and Skoog, 1962) solidified with agar. Plants were grown for 6-8 weeks in a lighted incubator room at 28-30° C. and leaves collected sterilely for use in the transformation protocol. Pieces of approximately one square centimeter were sterilely cut from these leaves, excluding the midrib. Cultures of the *Agrobacterium* strains (EHA101S containing pDAB3278, aka pDAS1580, AAD-13 (v1)+PAT), grown overnight in a flask on a shaker set at 250 rpm at 28° C., was pelleted in a centrifuge and resuspended in sterile Murashige & Skoog salts, and adjusted to a final optical density of 0.5 at 600 nm. Leaf pieces were dipped in this bacterial suspension for approximately 30 seconds, then blotted dry on sterile paper towels and placed right side up on TOB+medium (Murashige and Skoog medium containing 1 mg/L indole acetic acid and 2.5 mg/L benzyladenine) and incubated in the dark at 28° C. Two days later the leaf pieces were moved to TOB+medium containing 250 mg/L cefotaxime (Agri-Bio, North Miami, Fla.) and 5 mg/L glufosinate ammonium (active ingredient in Basta, Bayer Crop Sciences) and incubated at 28-30° C. in the light. Leaf pieces were moved to fresh TOB+medium with cefotaxime and Basta twice per week for the first two weeks and once per week thereafter. Four to six weeks after the leaf pieces were treated with the Agrobacteria; small plants arising from transformed foci were removed from this tissue preparation and planted into medium TOB-containing 250 mg/L cefotaxime and 10 mg/L Basta in Phytatray™ II vessels (Sigma). These plantlets were grown in a lighted incubator room. After 3 weeks, stem cuttings were taken and re-rooted in the same media. Plants were ready to send out to the greenhouse after 2-3 additional weeks.

Plants were moved into the greenhouse by washing the agar from the roots, transplanting into soil in 13.75 cm square pots, placing the pot into a Ziploc® bag (SC Johnson & Son, Inc.), placing tap water into the bottom of the bag, and placing in indirect light in a 30° C. greenhouse for one week. After 3-7 days, the bag was opened; the plants were fertilized and allowed to grow in the open bag until the plants were greenhouse-acclimated, at which time the bag is removed. Plants were grown under ordinary warm greenhouse conditions (30° C., 16 hour day, 8 hour night, minimum natural+supplemental light=500 $\mu E/m^2 s^1$).

Prior to propagation, $T_0$ plants were sampled for DNA analysis to determine the insert copy number. The PAT gene which was molecularly linked to AAD-13 (v1) was assayed for convenience. Fresh tissue was placed into tubes and lyophilized at 4° C. for 2 days. After the tissue was fully dried, a tungsten bead (Valenite) was placed in the tube and the samples were subjected to 1 minute of dry grinding using a Kelco bead mill. The standard DNeasy DNA isolation procedure was then followed (Qiagen, DNeasy 69109). An aliquot of the extracted DNA was then stained with Pico Green (Molecular Probes P7589) and read in the fluorometer (BioTek) with known standards to obtain the concentration in ng/µl.

The DNA samples were diluted to approximately 9 ng/µl and then denatured by incubation in a thermocycler at 95° C. for 10 minutes. Signal Probe mix is then prepared using the provided oligo mix and $MgCl_2$ (Third Wave Technologies). An aliquot of 7.5 µl is placed in each well of the Invader assay plate followed by an aliquot of 7.5 µl of controls, standards, and 20 ng/µl diluted unknown samples. Each well was overlaid with 15 µl of mineral oil (Sigma). The plates were incubated at 63° C. for 1.5 hours and read on the fluorometer (Biotek). Calculation of % signal over background for the target probe divided by the % signal over background internal control probe will calculate the ratio. The ratio of known copy standards developed and validated with southern blot analysis was used to identify the estimated copy of the unknown events.

All events were also assayed for the presence of the AAD-13 (v1) gene by PCR using the same extracted DNA samples. A total of 100 ng of total DNA was used as template. 20 mM of each primer was used with the Takara Ex Taq PCR Polymerase kit. Primers for the Plant Transcription Unit (PTU) PCR AAD-13 were (SdpacodF: ATGGCTCA TGCTGC-CCTCAGCC) (SEQ ID NO:6) and (SdpacodR: CGGGCAG-GCCTAACTCCACC AA) (SEQ ID NO:7). The PCR reaction was carried out in the 9700 Geneamp thermocycler (Applied Biosystems), by subjecting the samples to 94° C. for 3 minutes and 35 cycles of 94° C. for 30 seconds, 64° C. for 30 seconds, and 72° C. for 1 minute and 45 seconds followed by 72° C. for 10 minutes. PCR products were analyzed by electrophoresis on a 1% agarose gel stained with EtBr.

9.1—Selection of Transformed Plants.

Following the acclimation in the greenhouse $T_0$ plants were then randomly assigned to various rates of 2,4-D DMA ranging from 140 to 2240 g ae/ha at 4-fold increments. For tobacco, 140 g ae/ha 2,4-D is an effective dose to distinguish sensitive plants from ones with meaningful levels of resistance. Table 14 shows comparisons drawn to $T_0$ plants transformed with a glufosinate herbicide resistance gene (PAT/Cry1F-transformed tobacco). Data demonstrated that AAD-13 (v1) when transformed in tobacco plants provides robust tolerance to 2,4-D DMA to at least 2240 g ae/ha.

TABLE 14

Comparison of $T_0$ AAD-13 (v1) and transformed (PAT) control tobacco plant respose to various rates of 2,4-D DMA 14 days after application.

| Averages | % Injury | | | % Injury | | |
|---|---|---|---|---|---|---|
| | <20% | 20-40% | >40% | Ave | Std dev | Range (%) |
| PAT/Cry1F (transformed controls) | | | | | | |
| 0 g ae/ha 2,4-D DMA | 3 | 0 | 0 | 0.0 | 0.0 | 0 |
| 140 g ae/ha 2,4-D DMA | 0 | 1 | 2 | 47.0 | 6.0 | 40-50 |
| 560 g ae/ha 2,4-D DMA | 0 | 0 | 3 | 75.0 | 0.0 | 75 |
| 2240 g ae/ha 2,4-D DMA | 0 | 0 | 3 | 97.0 | 8.0 | 90-100 |
| AAD-13 (v1) gene T0 plants | | | | | | |
| 0 g ae/ha 2,4-D DMA | 2 | 0 | 0 | 0.0 | 0.0 | 0 |
| 140 g ae/ha 2,4-D DMA | 2 | 0 | 0 | 8.0 | 11.0 | 0-15 |
| 560 g ae/ha 2,4-D DMA | 2 | 0 | 0 | 3.0 | 4.0 | 0-5 |
| 2240 g ae/ha 2,4-D DMA | 2 | 0 | 0 | 5.0 | 0.0 | 5 |

T1 seed from individual T0 transformants were saved and seed was stratified and sown onto selection trays in the greenhouse much like that of Example 5 Prior to testing elevated rates of 2,4-D DMA, each $T_1$ line were progeny tested by applying 2,4-D DMA (560 g ae/ha) to 100 random $T_1$ siblings. Spray applications were made as previous described with a track sprayer calibrated to an application rate of 187 L/ha. Forty-three percent of the $T_0$ families ($T_1$ plants) segregated in the anticipated 3 Resistant:1 Sensitive model for a dominantly inherited single locus with Mendelian inheritance as determined by Chi square analysis (P>0.05).

Seed were collected from 12 to 20 $T_2$ individuals ($T_2$ seed). Twenty-five $T_3$ siblings from each of eight randomly-selected $T_2$ families will be progeny tested as previously described. Approximately one-third of the $T_2$ families are anticipated to be homozygous (non-segregating populations) in each line. These data show will show that AAD-13 (v1) is stably integrated and inherited in a Mendelian fashion to at least three generations.

Surviving $T_1$ plants were then randomly assigned to various rates of 2,4-D. For tobacco, 140 g ae/ha 2,4-D is an effective dose to distinguish sensitive plants from ones with meaningful levels of resistance. Elevated rates were also applied to determine relative levels of resistance (140, 560, or 2240 g ae/ha). Table 15 shows the comparisons drawn to an untransformed control (KY160) variety of tobacco.

All auxin herbicide applications were applied by track sprayer in a 187 L/ha spray volume. 2,4-D used was the commercial dimethylamine salt formulation (456 g ae/L, NuFarm, St Joseph, Mo.). Some $T_1$ individuals were subjected to alternative commercial herbicides instead of a phenoxy auxin. One point of interest was determining whether the pyridyloxyacetate auxin herbicides, triclopyr and fluoroxypyr, could be effectively degraded in planta. Herbicides were applied to $T_1$ plants with use of a track sprayer in a 187 L/ha spray volume. $T_1$ plants that exhibited tolerance to 2,4-D DMA were further accessed in the $T_2$ generation.

9.2—Results of Selection of Transformed Plants.

$T_1$ transformants were first selected from the background of untransformed plants using a 2,4-D selection scheme. Table 15 compares the response of AAD-13 (v1) and control genes to impart 2,4-D resistance to tobacco $T_1$ transformants. Response is presented in terms of % visual injury 2 WAT. Data are presented as a histogram of individuals exhibiting little or no injury (<20%), moderate injury (20-40%), or severe injury (>40%). An arithmetic mean and standard deviation is presented for each treatment. The range in individual response is also indicated in the last column for each rate and transformation. KY160 untransformed tobacco served as an auxin-sensitive control. The AAD-13 (v1) gene imparted herbicide resistance to individual $T_1$ tobacco plants.

9.3—Additional Foliar Applications Herbicide Resistance in AAD-13 Tobacco.

The ability of AAD-13 (v1) to provide resistance to other aryloxyalkanoate auxin herbicides in transgenic tobacco was determined by foliar application of various substrates. Extra $T_1$ generation plants following the T1 progeny testing were sprayed with the use of a track sprayer set at 187 L/ha. The plants were sprayed with a range of pyridyloxyacetate herbicides: 140-1120 g ae/ha triclopyr (Garlon 3A, Dow AgroSciences) and 280-1120 g ae/ha fluoroxypyr (Starane, Dow AgroSciences). All applications were formulated in water. Each treatment was replicated 3 times. Plants were evaluated at 3 and 14 days after treatment.

AAD-13-transformed plants were poorly protected from the triclopyr but were well protected from fluoroxypyr herbicide injury that was seen in the untransformed control line (see Table 16). These results confirm that AAD-13 (v1) in tobacco provides resistance to certain selected pyridyloxyacetic auxin tested. The AAD-13 (v1) gene provided significant tolerance up to 1120 g ae/ha fluoroxypyr, whereas the gene provided only modest level of tolerance to triclopyr as low as 280 g/ha. These data confirm that AAD-13 (v1) provides a selectivity bias toward fluoroxypyr over triclopyr of the pyridyloxy auxins in multiple species. This unexpected observation further distinguishes the AAD-13 (v1) gene from other herbicide tolerance enzymes of similar mechanism and is observed in multiple plant species.

TABLE 16

Comparison of $T_1$ AAD-13 (v1) and untransformed control tobacco plant response to various foliar applied auxinic herbicides 14 days after application.

Pyridyloxyacetic auxins

| Herbicide Treatment | Segregating T1 AAD-13 (v1) plants (pDAB4114[1]003.006) | KY160 (untransformed control) |
|---|---|---|
| 280 g ae/ha triclopyr | 53.0 | 82.0 |
| 560 g ae/ha triclopyr | 65.0 | 88.0 |
| 1120 g ae/ha triclopyr | 75.0 | 92.0 |
| 280 g ae/ha fluroxypyr | 7.0 | 100.0 |

TABLE 15

AAD-13 (v1) transformed $T_1$ tobacco response to a range of 2,4-D rates applied postemergence, compared to an untransformed, auxin-sensitive control.

| Averages | % Injury | | | % Injury | | |
|---|---|---|---|---|---|---|
| | <20% | 20-40% | >40% | Ave | Std dev | Range (%) |
| Wildtype (untransformed control) | | | | | | |
| Untreated control | 3 | 0 | 0 | 0.0 | 0.0 | 0 |
| 140 g ae/ha 2,4-DMA | 0 | 0 | 3 | 80.0 | 0.0 | 80 |
| 560 g ae/ha 2,4-DMA | 0 | 0 | 3 | 88.0 | 1.0 | 88-89 |
| 2240 g ae/ha 2,4-DMA | 0 | 0 | 3 | 92.0 | 3.0 | 90-95 |
| AAD-13 (v1) gene $T_1$ plants | | | | | | |
| Untreated control | 3 | 0 | 0 | 0.0 | 0.0 | 0 |
| 140 g ae/ha 2,4-DMA | 3 | 0 | 0 | 0.0 | 0.0 | 0 |
| 560 g ae/ha 2,4-DMA | 3 | 0 | 0 | 0.0 | 0.0 | 0 |
| 2240 g ae/ha 2,4-DMA | 3 | 0 | 0 | 2.0 | 3.0 | 0-5 |

TABLE 16-continued

Comparison of $T_1$ AAD-13 (v1) and untransformed control tobacco plant response to various foliar applied auxinic herbicides 14 days after application.
Pyridyloxyacetic auxins

| Herbicide Treatment | Segregating T1 AAD-13 (v1) plants (pDAB4114[1]003.006) | KY160 (untransformed control) |
|---|---|---|
| 560 g ae/ha fluroxypyr | 25.0 | 100.0 |
| 1120 g ae/ha fluroxypyr | 37.0 | 100.0 |

Example 10

AAD-13 (v1) in Canola and Transformation of Other Crops 10.1—Canola Transformation.

The AAD-13 (v1) gene conferring resistance to 2,4-D can be used to transform *Brassica napus* with *Agrobacterium*-mediated transformation using PAT as a selectable marker.

Seeds can be surface-sterilized with 10% commercial bleach for 10 minutes and rinsed 3 times with sterile distilled water. The seeds will be placed on one half concentration of MS basal medium (Murashige and Skoog, 1962) and maintained under growth regime set at 25° C., and a photoperiod of 16 hrs light/8 hrs dark.

Hypocotyl segments (3-5 mm) would be excised from 5-7 day old seedlings and placed on callus induction medium K1D1 (MS medium with 1 mg/L kinetin and 1 mg/L 2,4-D) for 3 days as pre-treatment. The segments will then be transferred into a petri plate, treated with *Agrobacterium* Z707S or LBA4404 strain containing pDAB3759. The *Agrobacterium* shall be grown overnight at 28° C. in the dark on a shaker at 150 rpm and subsequently re-suspended in the culture medium.

After 30 min treatment of the hypocotyl segments with *Agrobacterium*, these would be placed back on the callus induction medium for 3 days. Following co-cultivation, the segments will be placed on K1D1TC (callus induction medium containing 250 mg/L Carbenicillin and 300 mg/L Timentin) for one week or two weeks of recovery. Alternately, the segments would be placed directly on selection medium K1D1H1 (above medium with 1 mg/L Herbiace). Carbenicillin and Timentin antibiotics would be used to kill the *Agrobacterium*. The selection agent Herbiace allows the growth of the transformed cells.

Callused hypocotyl segments would be placed on B3Z1H1 (MS medium, 3 mg/L benzylamino purine, 1 mg/L Zeatin, 0.5 gm/L MES [2-(N-morpholino) ethane sulfonic acid], 5 mg/L silver nitrate, 1 mg/L Herbiace, Carbenicillin and Timentin) shoot regeneration medium. After 2-3 weeks shoots regenerate and hypocotyl segments along with the shoots are transferred to B3Z1H3 medium (MS medium, 3 mg/L benzylamino purine, 1 mg/L Zeatin, 0.5 gm/L MES [2-(N-morpholino) ethane sulfonic acid], 5 mg/L silver nitrate, 3 mg/L Herbiace, Carbenicillin and Timentin) for another 2-3 weeks.

Shoots would be excised from the hypocotyl segments and transferred to shoot elongation medium MESH5 or MES10 (MS, 0.5 gm/L MES, 5 or 10 mg/L Herbiace, Carbenicillin, Timentin) for 2-4 weeks. The elongated shoots are cultured for root induction on MSI.1 (MS with 0.1 mg/L Indolebutyric acid). Once the plants are well established root system, these will be transplanted into soil. The plants are acclimated under controlled environmental conditions in the Conviron for 1-2 weeks before transfer to the greenhouse.

10.2—*Agrobacterium* Transformation of Other Crops

In light of the subject disclosure, additional crops can be transformed according to the subject invention using techniques that are known in the art. For *Agrobacterium*-mediated trans-formation of rye, see, e.g., Popelka and Altpeter (2003)., see, e.g., Hinchee et al., 1988. For *Agrobacterium*-mediated transformation of sorghum, see, e.g., Zhao et al., 2000. For *Agrobacterium*-mediated transformation of barley, see, e.g., Tingay et al., 1997. For *Agrobacterium*-mediated transformation of wheat, see, e.g., Cheng et al., 1997. For *Agrobacterium*-mediated transformation of rice, see, e.g., Hiei et al., 1997.

The Latin names for these and other plants are given below. It should be clear that these and other (non-*Agrobacterium*) transformation techniques can be used to transform AAD-13 (v1), for example, into these and other plants, including but not limited to Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa, Solanum incanum* and other spp., and *Cyphomandra betacea*), Potato (*Solanum tubersoum*), Sweet potato (*Ipomoea betatas*), Rye (*Secale* spp.), Peppers (*Capsicum annuum, sinense*, and *frutescens*), Lettuce (*Lactuca sativa, perennis*, and *pulchella*), Cabbage (*Brassica* spp), Celery (*Apium graveolens*), Eggplant (*Solanum melongena*), Peanut (*Arachis hypogea*), Sorghum (all *Sorghum* species), Alfalfa (*Medicago sativua*), Carrot (*Daucus carota*), Beans (*Phaseolus* spp. and other genera), Oats (*Avena sativa* and *strigosa*), Peas (*Pisum, Vigna*, and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynadon*, and other genera), Clover (*Tifolium*), Vetch (*Vicia*). Such plants, with AAD-13 (v1) genes, for example, are included in the subject invention.

AAD-13 (v1) has the potential to increase the applicability of key auxinic herbicides for in-season use in many deciduous and evergreen timber cropping systems. Triclopyr, 2,4-D, and/or fluoroxypyr resistant timber species would increase the flexibility of over-the-top use of these herbicides without injury concerns. These species would include, but not limited to: Alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp), and pine (*Pinus* spp). Use of auxin resistance for the selective weed control in ornamental and fruit-bearing species is also within the scope of this invention. Examples could include, but not be limited to, rose (*Rosa* spp.), burning bush (*Euonymus* spp.), petunia (*Petunia* spp) begonia (*Begonia* spp.), rhododendron (*Rhododendron* spp), crabapple or apple (*Malus* spp.), pear (*Pyrus* spp.), peach (*Prunus* spp), and marigolds (*Tagetes* spp.).

Example 11

Further Evidence of Surprising Results: AAD-13 vs. AAD-2

Freshly harvested $T_1$ *Arabidopsis* seed transformed with a plant optimized AAD-13 (v1) or native AAD-2 (v1) gene (see PCT/US2005/014737) were planted and selected for resistance to glufosinate as previously described Plants were then randomly assigned to various rates of 2,4-D (50-3200 g ae/ha). Herbicide applications were applied by track sprayer in a 187 L/ha spray volume. 2,4-D used was the commercial dimethylamine salt formulation (456 g ae/L, NuFarm, St Joseph, Mo.) mixed in 200 mM Tris buffer (pH 9.0) or 200 mM HEPES buffer (pH7.5).

AAD-13 (v1) and AAD-2 (v1) did provide detectable 2,4-D resistance versus the transformed and untransformed control lines; however, individuals varied in their ability to impart 2,4-D resistance to individual $T_1$ Arabidopsis plants. Surprisingly, AAD-2 (v1) and AAD-2 (v2) transformants were far less resistant to 2,4-D than the AAD-13 (v1) gene, both from a frequency of highly tolerant plants as well as overall average injury. No plants transformed with AAD-2 (v1) survived 200 g ae/ha 2,4-D relatively uninjured (<20% visual injury), and overall population injury was about 83% (see PCT/US2005/014737). Conversely, AAD-13 (v1) had a population injury average of about 15% when treated with 2,240 g ae/ha 2,4-D (Table 11). Comparison of both AAD-13 and AAD-2 plant optimized genes indicates a significant advantage for AAD-13 (v1) in planta.

These results are unexpected given that the in vitro comparison of AAD-2 (v1) (see PCT/US2005/014737) and AAD-13 (v2) indicated both were highly efficacious at degrading 2,4-D and both shared an S-type specificity with respect to chiral aryloxyalkanoate substrates. AAD-2 (v1) is expressed in individual $T_1$ plants to varying levels; however, little protection from 2,4-D injury is afforded by this expressed protein. No substantial difference was evident in protein expression level (in planta) for the native and plant optimized AAD-2 genes (see PCT/US2005/014737). These data corroborate earlier findings that make the functional expression of AAD-13 (v1) in planta, and resulting herbicide resistance to 2,4-D and selected pyridyloxyacetate herbicides, is unexpected.

Example 12

Preplant Burndown Applications

This and the following Examples are specific examples of novel herbicide uses made possible by the subject AAD-13 invention.

Preplant burndown herbicide applications are intended to kill weeds that have emerged over winter or early spring prior to planting a given crop. Typically these applications are applied in no-till or reduced tillage management systems where physical removal of weeds is not completed prior to planting. An herbicide program, therefore, must control a very wide spectrum of broadleaf and grass weeds present at the time of planting. Glyphosate, gramoxone, and glufosinate are examples of non-selective, non-residual herbicides widely used for preplant burndown herbicide applications. Some weeds, however, are difficult to control at this time of the season due to one or more of the following: inherent insensitivity of the weed species or biotype to the herbicide, relatively large size of winter annual weeds, and cool weather conditions limiting herbicide uptake and activity. Several herbicide options are available to tankmix with these herbicides to increase spectrum and activity on weeds where the non-selective herbicides are weak. An example would be 2,4-D tankmix applications with glyphosate to assist in the control of Conyza canadensis (horseweed). Glyphosate can be used from 420 to 1680 g ae/ha, more typically 560 to 840 g ae/ha, for the preplant burndown control of most weeds present; however, 280-1120 g ae/ha of 2,4-D can be applied to aid in control of many broadleaf weed species (e.g., horseweed).

2,4-D is an herbicide of choice because it is effective on a very wide range of broadleaf weeds, effective even at low temperatures, and extremely inexpensive. However, if the subsequent crop is a sensitive dicot crop, 2,4-D residues in the soil (although short-lived) can negatively impact the crop. Soybeans are a sensitive crop and require a minimum time period of 7 days (for 280 g ae/ha 2,4-D rate) to at least 30 days (for 2,4-D applications of 1120 g ae/ha) to occur between burndown applications and planting. 2,4-D is prohibited as a burndown treatment prior to cotton planting (see federal labels, most are available through CPR, 2005 or online at cdms.net/manuf/manuf.asp). With AAD-13 (v1) transformed cotton or soybeans, these crops should be able to survive 2,4-D residues in the soil from burndown applications applied right up to and even after planting before emergence of the crop. The increased flexibility and reduced cost of tankmix (or commercial premix) partners will improve weed control options and increase the robustness of burndown applications in important no-till and reduced tillage situations. This example is one of many options that will be available. Those skilled in the art of weed control will note a variety of other applications including, but not limited to gramoxone+2,4-D or glufosinate+2,4-D by utilizing products described in federal herbicide labels (CPR, 2005) and uses described in Agriliance Crop Protection Guide (2005), as examples. Those skilled in the art will also recognize that the above example can be applied to any 2,4-D-sensitive (or other phenoxy auxin herbicide) crop that would be protected by the AAD-13 (v1) gene if stably transformed. Likewise, the unique attributes of AAD-13 allowing degradation of fluoroxypyr increase utility by allowing substitution or tank mixes of 35-560 g ae/ha fluoroxypyr to increase spectrum and/or increase the ability to control perennial or viney weed species.

Example 13

In-Crop Use of Auxin Herbicides in Soybeans, Cotton, and Other Dicot Crops Transformed Only with AAD-13 (v1)

AAD-13 (v1) can enable the use of phenoxy auxin herbicides (e.g., 2,4-D and MCPA) and pyridyloxy auxins (fluoroxypyr) for the control of a wide spectrum of broadleaf weeds directly in crops normally sensitive to 2,4-D. Application of 2,4-D at 280 to 2240 g ae/ha would control most broadleaf weed species present in agronomic environments. More typically, 560-1120 g ae/ha is used. For fluoroxypyr, application rates would typically range from 35-560 g ae/ha, more typically 70-280 ae/ha.

An advantage to this additional tool is the extremely low cost of the broadleaf herbicide component and potential short-lived residual weed control provided by higher rates of 2,4-D and fluoroxypyr when used at higher rates, whereas a non-residual herbicide like glyphosate would provide no control of later germinating weeds. This tool also provides a mechanism to combine herbicide modes of action with the convenience of HTC as an integrated herbicide resistance and weed shift management strategy.

A further advantage this tool provides is the ability to tankmix broad spectrum broadleaf weed control herbicides (e.g., 2,4-D and fluoroxypyr) with commonly used residual weed control herbicides. These herbicides are typically applied prior to or at planting, but often are less effective on emerged, established weeds that may exist in the field prior to planting. By extending the utility of these aryloxy auxin herbicides to include at-plant, preemergence, or pre-plant applications, the flexibility of residual weed control programs increases. One skilled in the art would recognize the residual herbicide program will differ based on the crop of interest, but typical programs would include herbicides of the chloracetmide and dinitroaniline herbicide families, but also including herbicides such as clomazone, sulfentrazone, and a variety of ALS-inhibiting, PPO-inhibiting, and HPPD-inhibiting herbicides.

Further benefits could include tolerance to 2,4-D or fluoroxypyr required before planting following aryloxyacetic acid auxin herbicide application (see previous example); and fewer problems from contamination injury to dicot crops resulting from incompletely cleaned bulk tanks that had contained 2,4-D or fluoroxypyr. Dicamba, R-dhichlorprop, and many other herbicides can still be used for the subsequent control of AAD-13 (v1)-transformed dicot crop volunteers.

Those skilled in the art will also recognize that the above example can be applied to any 2,4-D-sensitive (or other aryloxy auxin herbicide) crop that would be protected by the AAD-13 (v1) gene if stably transformed. One skilled in the art of weed control will now recognize that use of various commercial phenoxy or pyridyloxy auxin herbicides alone or in combination with an herbicide is enabled by AAD-13 (v1) transformation. Specific rates of other herbicides representative of these chemistries can be determined by the herbicide labels compiled in the CPR (Crop Protection Reference) book or similar compilation or any commercial or academic crop protection references such as the Crop Protection Guide from Agriliance (2005). Each alternative herbicide enabled for use in HTCs by AAD-13 (v1), whether used alone, tank mixed, or sequentially, is considered within the scope of this invention.

Example 14

In-Crop Use of Phenoxy Auxin and Pyridyloxy Auxin Herbicides in AAD-13 (v1) Only Transformed Corn, Rice, and Other Monocot Species In an analogous fashion, transformation of grass species (such as, but not limited to, corn, rice, wheat, barley, or turf and pasture grasses) with AAD-13 (v1) would allow the use of highly efficacious phenoxy and pyridyloxy auxins in crops where normally selectivity is not certain. Most grass species have a natural tolerance to auxinic herbicides such as the phenoxy auxins (i.e., 2,4-D.). However, a relatively low level of crop selectivity has resulted in diminished utility in these crops due to a shortened window of application timing or unacceptable injury risk. AAD-13 (v1)-transformed monocot crops would, therefore, enable the use of a similar combination of treatments described for dicot crops such as the application of 2,4-D at 280 to 2240 g ae/ha to control most broadleaf weed species. More typically, 560-1120 g ae/ha is used. For fluoroxypyr, application rates would typically range from 35-560 g ae/ha, more typically 70-280 ae/ha.

An advantage to this additional tool is the extremely low cost of the broadleaf herbicide component and potential short-lived residual weed control provided by higher rates of 2,4-D or fluoroxypyr. In contrast, a non-residual herbicide like glyphosate would provide no control of later-germinating weeds. This tool would also provide a mechanism to rotate herbicide modes of action with the convenience of HTC as an integrated-herbicide-resistance and weed-shift-management strategy in a glyphosate tolerant crop/AAD-13 (v1) HTC combination strategy, whether one rotates crops species or not.

A further advantage this tool provides is the ability to tankmix broad spectrum broadleaf weed control herbicides (e.g., 2,4-D and fluoroxypyr) with commonly used residual weed control herbicides. These herbicides are typically applied prior to or at planting, but often are less effective on emerged, established weeds that may exist in the field prior to planting. By extending the utility of these aryloxy auxin herbicides to include at-plant, preemergence, or pre-plant applications, the flexibility of residual weed control programs increases. One skilled in the art would recognize the residual herbicide program will differ based on the crop of interest, but typical programs would include herbicides of the chloracetmide and dinitroaniline herbicide families, but also including herbicides such as clomazone, sulfentrazone, and a variety of ALS-inhibiting, PPO-inhibiting, and HPPD-inhibiting herbicides.

The increased tolerance of corn, rice, and other monocots to the phenoxy or pyridyloxy auxins shall enable use of these herbicides in-crop without growth stage restrictions or the potential for crop leaning; unfurling phenomena such as "rattailing," growth regulator-induced stalk brittleness in corn, or deformed brace roots. Each alternative herbicide enabled for use in HTCs by AAD-13 (v1), whether used alone, tank mixed, or sequentially, is considered within the scope of this invention.

Example 15

AAD-13 (v1) Stacked with Glyphosate Tolerance Trait in any Crop

The vast majority of cotton, canola, corn, and soybean acres planted in North America contain a glyphosate tolerance (GT) trait, and adoption of GT corn is on the rise. Additional GT crops (e.g., wheat, rice, sugar beet, and turf) have been under development but have not been commercially released to date. Many other glyphosate resistant species are in experimental to development stage (e.g., alfalfa, sugar cane, sunflower, beets, peas, carrot, cucumber, lettuce, onion, strawberry, tomato, and tobacco; forestry species like poplar and sweetgum; and horticultural species like marigold, petunia, and begonias; isb.vt.edu/cfdocs/fieldtests1.cfm, 2005 on the World Wide Web). GTC's are valuable tools for the sheer breadth of weeds controlled and convenience and cost effectiveness provided by this system. However, glyphosate's utility as a now-standard base treatment is selecting for glyphosate resistant weeds. Furthermore, weeds that glyphosate is inherently less efficacious on are shifting to the predominant species in fields where glyphosate-only chemical programs are being practiced. By stacking AAD-13 (v1) with a GT trait, either through conventional breeding or jointly as a novel transformation event, weed control efficacy, flexibility, and ability to manage weed shifts and herbicide resistance development could be improved. As mentioned in previous examples, by transforming crops with AAD-13 (v1), monocot crops will have a higher margin of phenoxy or pyridyloxy auxin safety, and phenoxy auxins can be selectively applied in dicot crops. Several scenarios for improved weed control options can be envisioned where AAD-13 (v1) and a GT trait are stacked in any monocot or dicot crop species:

a) Glyphosate can be applied at a standard postemergent application rate (420 to 2160 g ae/ha, preferably 560 to 840 g ae/ha) for the control of most grass and broadleaf weed species. For the control of glyphosate resistant broadleaf weeds like *Conyza canadensis* or weeds inherently difficult to control with glyphosate (e.g., *Commelina* spp, *Ipomoea* spp, etc), 280-2240 g ae/ha (preferably 560-1120 g ae/ha) 2,4-D can be applied sequentially, tank mixed, or as a premix with glyphosate to provide effective control. For fluoroxypyr, application rates would typically range from 35-560 g ae/ha, more typically 70-280 ae/ha.

b) Currently, glyphosate rates applied in GTC's generally range from 560 to 2240 g ae/ha per application timing. Glyphosate is far more efficacious on grass species than broadleaf weed species. AAD-13 (v1)+GT stacked traits would allow grass-effective rates of glyphosate (105-840 g ae/ha, more preferably 210-420 g ae/ha). 2,4-D (at 280-2240 g ae/ha, more preferably 560-1120 g ae/ha) could then be applied sequentially, tank mixed, or as a premix with grass-effective rates of glyphosate to provide necessary broadleaf weed control. Fluoroxypyr at rates mentioned above would be acceptable components in the treatment regimin. The low rate of glyphosate would also provide some benefit to the broadleaf weed control; however, primary control would be from the 2,4-D or fluoroxypyr.

One skilled in the art of weed control will recognize that use of one or more commercial aryloxy auxin herbicides alone or in combination (sequentially or independently) is enabled by AAD-13 (v1) transformation into crops. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-13 (v1), whether used alone, tank mixed, or sequentially, is considered within the scope of this invention.

Example 16

AAD-13 (v1) Stacked with Glufosinate Tolerance Trait in any Crop

Glufosinate tolerance (PAT, bar) is currently present in a number of crops planted in North America either as a selectable marker for an input trait like insect resistance proteins or specifically as an HTC trait. Crops include, but are not limited to, glufosinate tolerant canola, corn, and cotton. Additional glufosinate tolerant crops (e.g., rice, sugar beet, soybeans, and turf) have been under development but have not been commercially released to date. Glufosinate, like glyphosate, is a relatively non-selective, broad spectrum grass and broadleaf herbicide. Glufosinate's mode of action differs from glyphosate. It is faster acting, resulting in desiccation and "burning" of treated leaves 24-48 hours after herbicide application. This is advantageous for the appearance of rapid weed control. However, this also limits translocation of glufosinate to meristematic regions of target plants resulting in poorer weed control as evidenced by relative weed control performance ratings of the two compounds in many species (Agriliance, 2005).

By stacking AAD-13 (v1) with a glufosinate tolerance trait, either through conventional breeding or jointly as a novel transformation event, weed control efficacy, flexibility, and ability to manage weed shifts and herbicide resistance development could be improved. Several scenarios for improved weed control options can be envisioned where AAD-13 (v1) and a glufosinate tolerance trait are stacked in any monocot or dicot crop species:

a) Glufosinate can be applied at a standard postemergent application rate (200 to 1700 g ae/ha, preferably 350 to 500 g ae/ha) for the control of many grass and broadleaf weed species. To date, no glufosinate-resistant weeds have been confirmed; however, glufosinate has a greater number of weeds that are inherently more tolerant than does glyphosate.

i) Inherently tolerant broadleaf weed species (e.g., *Cirsium arvensis Apocynum cannabinum*, and *Conyza candensis*) could be controlled by tank mixing 280-2240 g ae/ha, more preferably 560-2240 g ae/ha, 2,4-D for effective control of these more difficult-to-control perennial species and to improve the robustness of control on annual broadleaf weed species. Fluoroxypyr would be acceptable components to consider in the weed control regimen. For fluoroxypyr, application rates would typically range from 35-560 g ae/ha, more typically 70-280 ae/ha.

b) A multiple combination of glufosinate (200-500 g ae/ha)+/−2,4-D (280-1120 g ae/ha)+/−fluoroxypyr (at rates listed above), for example, could provide more robust, overlapping weed control spectrum. Additionally, the overlapping spectrum provides an additional mechanism for the management or delay of herbicide resistant weeds.

One skilled in the art of weed control will recognize that use of one or more commercial aryloxyacetic auxin herbicides alone or in combination (sequentially or independently) is enabled by AAD-13 (v1) transformation into crops. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-13 (v1), whether used alone, tank mixed, or sequentially, is considered within the scope of this invention.

The subject invention thus includes a transgenic plant (and plant cells) comprising an AAD-13 gene of the subject invention "stacked" with a DSM-2 gene of PCT/US2007/086813 (filed Dec. 7, 2007). Such DSM-2 genes include SEQ ID NOS:1 and 3 of that application. Those genes encode proteins comprising SEQ ID NOS:2 and 4 of that application. Still further, additional herbicide tolerance genes can be included in multiple "stacks" comprising three or more such genes.

Example 17

AAD-13 (v1) Stacked with the AAD-1 (v3) Trait in any Crop

Homozygous AAD-13 (v1) and AAD-1 (v3) plants (see PCT/US2005/014737 for the latter) can be both reciprocally crossed and $F_1$ seed collected. The $F_1$ seed from two reciprocal crosses of each gene were stratified and treated 4 reps of each cross were treated under the same spray regimine as used for the other testing with one of the following treatments: 70, 140, 280 g ae/ha fluoroxypyr (selective for the AAD-12 (v1) gene); 280, 560, 1120 g ae/ha R-dichloroprop (selective for the AAD-1 (v3) gene); or 560, 1120, 2240 g ae/ha 2,4-D DMA (to confirm 2,4-D tolerance). Homozygous $T_2$ plants of each gene were also planted for use as controls. Plants were graded at 3 and 14 DAT. Spray results are shown in Table 24.

The results confirm AAD-13 (v1) can be successfully stacked with AAD-1 (v3), thus increasing the spectrum herbicides that may be applied to the crop of interest (phenoxyactetic acids+phenoxypropionic acids vs penoxyacetic acids+pyridyloxyacetic acids for AAD-1 and AAD-13, respectively). The complementary nature of herbicide cross resistance patterns allows convenient use of these two genes as complementary and stackable field-selectable markers. In crops where tolerance with a single gene may be marginal, one skilled in the art recognizes that one can increase tolerance by stacking a second tolerance gene for the same herbicide. Such can be done using the same gene with the same or different promoters; however, as observed here, stacking and tracking two completmentary traits can be facilitated by the distinguishing cross protection to phenoxypropionic acids [from AAD-1 (v3)] or pyidyloxyacetic acids [AAD-13 (v1)].

The subject invention thus includes a transgenic plant (and plant cells) comprising an AAD-13 gene of the subject invention "stacked" with an AAD-1 gene of WO 2005/107437 (*published* Nov. 17, 2005; PCT/US2005/014737 (filed May 2, 2005)). Such AAD-1 genes include SEQ ID NOS:3, 4, 5, and 12 of that application. These genes encode proteins comprising SEQ ID NOS:9, 10, 11, and 13 of that application. Still further, additional herbicide tolerance genes can be included in multiple "stacks" comprising three or more such genes.

Example 18

AAD-13 (v1) Stacked with the AAD-12 (v1) Trait in any Crop

Homozygous AAD-13 (v1) and AAD-12 (v1) plants (see WO 2007/053482 for the latter) can be crossed and $F_1$ seed was collected. The $F_1$ seed from two reciprocal crosses of each gene can be sown and F1 plants treated under the same spray regimine as used for the other testing with one of the following treatments: 70, 280, 1120 g ae/ha fluoroxypyr (selective for the AAD-12 (v1) gene); 70, 280, 1120 g ae/ha triclopyr (selective for the AAD-13 (v1) gene); or 560, 1120, 2240 g ae/ha 2,4-D DMA (to confirm 2,4-D tolerance).

AAD-13 (v1) can be stacked with AAD-12 (v1), thus increasing the spectrum herbicides that may be applied to the crop of interest (phenoxyactetic acids+triclopyr vs phenoxyacetic acids+fluoroxypyr for AAD-12 and AAD-13, respectively). The complementary nature of herbicide cross resistance patterns allows convenient use of these two genes as complementary and stackable field-selectable markers. In crops where tolerance with a single gene may be marginal, one skilled in the art recognizes that one can increase tolerance by stacking a second tolerance gene for the same herbicide. Such can be done using the same gene with the same or different promoters; however, as observed here, stacking and tracking two complementary traits can be facilitated by the distinguishing cross protection to fluoroxypyr [from AAD-13 (v1)] and triclopyr [AAD-12 (v1)].

The subject invention thus includes a transgenic plant (and plant cells) comprising an AAD-13 gene of the subject invention "stacked" with an AAD-12 gene of WO 2007/053482 (published May 10, 2007; PCT/US2006/042133 (filed Oct. 27, 2006)). Such AAD-12 genes include SEQ ID NOS:1, 3, and 5 of that application. Those genes encode proteins comprising SEQ ID NOS:2 and 4 of that application. Still further, additional herbicide tolerance genes can be included in multiple "stacks" comprising three or more such genes.

Example 19

AAD-13 (v1) Stacked with AHAS Trait in any Crop

Imidazolinone herbicide tolerance (AHAS, et al.) is currently present in a number of crops planted in North America including, but not limited to, corn, rice, and wheat. Additional imidazolinone tolerant crops (e.g., cotton and sugar beet) have been under development but have not been commercially released to date. Many imidazolinone herbicides (e.g., imazamox, imazethapyr, imazaquin, and imazapic) are currently used selectively in various conventional crops. The use of imazethapyr, imazamox, and the non-selective imazapyr has been enabled through imidazolinone tolerance traits like AHAS et al. This chemistry class also has significant soil residual activity, thus being able to provide weed control extended beyond the application timing, unlike glyphosate or glufosinate-based systems. However, the spectrum of weeds controlled by imidazolinone herbicides is not as broad as glyphosate (Agriliance, 2005). Additionally, imidazolinone herbicides have a mode of action (inhibition of acetolactate synthase, ALS) to which many weeds have developed resistance (Heap, 2007). By stacking AAD-13 (v1) with an imidazolinone tolerance trait, either through conventional breeding or jointly as a novel transformation event, weed control efficacy, flexibility, and ability to manage weed shifts and herbicide resistance development could be improved. As mentioned in previous examples, by transforming crops with AAD-13 (v1), monocot crops will have a higher margin of phenoxy or pyridyloxy auxin safety, and these auxins can be selectively applied in dicot crops. Several scenarios for improved weed control options can be envisioned where AAD-13 (v1) and an imidazolinone tolerance trait are stacked in any monocot or dicot crop species:

a) Imazethapyr can be applied at a standard postemergent application rate of (35 to 280 g ae/ha, preferably 70-140 g ae/ha) for the control of many grass and broadleaf weed species.
  i) ALS-inhibitor resistant broadleaf weeds like *Amaranthus rudis, Ambrosia trifida, Chenopodium album* (among others, Heap, 2005) could be controlled by tank mixing 280-2240 g ae/ha, more preferably 560-1120 g ae/ha, 2,4-D. For fluoroxypyr, application rates would typically range from 35-560 g ae/ha, more typically 70-280 ae/ha.
  ii) Inherently more tolerant broadleaf species to imidazolinone herbicides like *Ipomoea* spp. can also be controlled by tank mixing 280-2240 g ae/ha, more preferably 560-1120 g ae/ha, 2,4-D. See rates above for triclopyr or fluoroxypyr.
b) A multiple combination of imazethapyr (35 to 280 g ae/ha, preferably 70-140 g ae/ha)+/−2,4-D (280-1120 g ae/ha)+/−fluoroxypyr (at rates listed above), for example, could provide more robust, overlapping weed control spectrum. Additionally, the overlapping spectrum provides an additional mechanism for the management or delay of herbicide resistant weeds.

One skilled in the art of weed control will recognize that use of any of various commercial imidazolinone herbicides, phenoxyacetic or pyridyloxyacetic auxin herbicides, alone or in multiple combinations, is enabled by AAD-13 (v1) transformation and stacking with any imidazolinone tolerance trait either by conventional breeding or genetic engineering. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-13 (v1), whether used alone, tank mixed, or sequentially, is considered within the scope of this invention.

Example 20

AAD-13 (v1) Stacked with Insect Resistance (IR) or Other Input Traits in any Crop Insect resistance in crops supplied by a transgenic trait is prevelant in corn and cotton production in North America and across the globe. Commercial products having combined IR and HT traits have been developed by multiple seed companies. These include Bt IR traits (e.g. Bt toxins listed at the website lifesci.sussex.ac.uk, 2006) and any or all of the HTC traits mentioned above. The value this offering brings is the ability to control multiple pest problems through genetic means in a single offering. The convenience of this offering will be restricted if weed control and insect control are accomplished independent of each other. AAD-13 (v1) alone or stacked with one or more additional HTC traits can be stacked with one or more additional input traits (e.g., insect resistance, fungal resistance, or stress tolerance, et al.) (isb.vt.edu/cfdocs/fieldtests1.cfm, 2005) either through conventional breeding or jointly as a novel transformation event. Benefits include the convenience and flexibility described in previous examples together with the ability to manage insect pests and/or other agronomic stresses in addition to the improved weed control offered by AAD-13 and associated herbicide tolerance. Thus, the subject invention can be used to provide a complete agronomic package of improved crop quality with the ability to flexibly and cost effectively control any number of agronomic issues.

Combined traits of IR and HT have application in most agronomic and horticultural/ornamental crops and forestry. The combination of AAD-13 and its commensurate herbicide tolerance and insect resistance afforded by any of the number of Bt or non-Bt IR genes are can be applied to the crop species listed (but not limited to) in Example 13. One skilled in the art of weed control will recognize that use of any of various commercial herbicides described in Examples 18-20, phenoxyacetic or pyridyloxyacetic auxin herbicides, alone or in multiple combinations, is enabled by AAD-13 (v1) transformation and stacking with the corresponding HT trait or IR trait either by conventional breeding or genetic engineering. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2005). Each alternative herbicide enabled for use in HTCs by AAD-13 (v1), whether used alone, tank mixed, or sequentially, is considered within the scope of this invention.

Example 21

AAD-13 (v1) as an In Vitro Dicot Selectable Marker

Genetic engineering of plant cell, tissue, organ, and plant or organelle such as plastid starts with the process of inserting genes of interest into plant cells using a suitable delivery method. However, when a gene is delivered to plant cells, only an extremely small percentage of cells integrate the heterogeneous gene into their genome. In order to select those few cells that have incorporated the gene of interest, researchers link a selectable or screenable "marker gene" to the gene of interest (GOI) in the vector. Cells that contain these markers are identified from the whole population of cells/tissue to which the DNA plasmid vector was delivered. By selecting those cells that express the marker gene, researchers are able to identify those few cells that may have incorporated the GOI into their genome. AAD-13 (v1) can function as a selectable marker when used as in Example #24 of patent application WO 2007/053482 (Wright et al.).

---

We claim:

1. A method of detecting whether a plant comprises a polynucleotide for herbicide tolerance, said method comprising collecting a sample from said plant, and assaying said sample for the presence of said polynucleotide or said polynucleotide encoded protein, wherein said polynucleotide encodes a protein that enzymatically degrades an aryloxyalkanoate chemical substructure of an aryloxyalkanoate herbicide, wherein said polynucleotide is operably linked to a promoter that is functional in a plant cell, and wherein said protein is at least 95% identical to a sequence selected from the group consisting of SEQ ID NO:2 and SEQ ID NO:4.

2. The method of 1 wherein said method comprises using a PCR primer or probe to detect for presence of said polynucleotide.

3. The method of 1 wherein said method comprises using an antibody to detect for presence of said protein.

4. A method of controlling glyphosate-resistant, naturally glyphosate tolerant, and/or naturally glufosinate tolerant weeds in a field of glyphosate and/or glufosinate tolerant crop plants, wherein said plants comprise a polynucleotide for herbicide tolerance, said method comprising applying an aryloxyalkanoate herbicide to at least a portion of said field, wherein said polynucleotide encodes a protein that enzymatically degrades an aryloxyalkanoate chemical substructure of an aryloxyalkanoate herbicide, wherein said polynucleotide is operably linked to a promoter that is functional in a plant cell, and wherein said protein is at least 95% identical to a sequence selected from the group consisting of SEQ ID NO:2 and SEQ ID NO:4.

5. The method of claim 4 wherein said aryloxyalkanoate herbicide is a phenoxy auxin.

6. The method of claim 5 wherein said phenoxy auxin is 2,4-D.

7. A method of controlling weeds in a field of crop plants, wherein said weeds are resistant to a herbicide, and said crop plants comprise a polynucleotide for herbicide tolerance, said method comprising applying an aryloxyalkanoate herbicide to at least a portion of said field, wherein said polynucleotide encodes a protein that enzymatically degrades an aryloxyalkanoate chemical substructure of an aryloxyalkanoate herbicide, wherein said polynucleotide is operably linked to a promoter that is functional in a plant cell, and wherein said protein is at least 95% identical to a sequence selected from the group consisting of SEQ ID NO:2 and SEQ ID NO:4.

8. The method of claim 7 wherein said weeds are resistant to an ALS-inhibiting herbicide.

9. The method of claim 7 wherein said weeds are glyphosate-resistant weeds and said crop plants are glyphosate tolerant crop plants.

10. The method of claim 7 wherein said aryloxyalkanoate herbicide is a phenoxy auxin.

11. The method of claim 7, said method comprising applying a 2,4-D herbicide to said crop plant and to a weed, wherein said weed is resistant to glyphosate.

12. The method of claim 11 wherein said method is used to control at least one glyphosate resistant volunteer plant of a different species than said crop plant.

* * * * *

SEQUENCE LISTING

```
<160> NUMBER OF SEQ ID NOS: 16

<210> SEQ ID NO 1
<211> LENGTH: 864
<212> TYPE: DNA
<213> ORGANISM: Sphingobium herbicidovorans

<400> SEQUENCE: 1
atgtcacccg ccttcgacat cgccccgctc gacgccacgt tcggcgccgt cgtcaccggc       60
gtgaagctcg ccgatctcga tgatgccgga tggctcgacc tgcaggctgc ctggctcgag      120
tacgcactcc tcgtttttccc cgatcagcat ctcacgcgcg agcagcagat cgcctttgcc      180
cgtcgcttcg ggccactcga gttcgagatg gccgcgatca gcaacgtgcg gcccgacggc      240
agcctgcggg tcgagagcga caacgacgac atgatgaaga tcctgaaggg caacatgggc      300
tggcatgccg acagcaccta catgccggtc caggccaagg gcgcggtgtt cagtgccgaa      360
gtggttccta gcgtcggcgg ccagaccggc ttcgccgaca tgcgcgcggc ctacgacgcg      420
ctcgacgagg atctgaaggc gcgcgtcgag acgctgcagg cccggcactc gctgcattac      480
agccagtcga agctcggcca ccagaccaag gcggccgacg gtgaatatag cggctacggg      540
ctgcatgacg ggccggtgcc gctgcggccg ctggtgaaga tccatcccga gaccggccgc      600
aagtcgctgc tgatcggccg ccacgcccac gccattcccg gcttggagcc agccgagtcc      660
gaacgcttgc tgcagcagct gatcgacttc gcctgccagc cgccgcgaat ctatcatcac      720
```

```
gactgggcgc cgggcgacgc cgtgctgtgg gacaatcgct gcctgctgca ccaggcgacg      780
ccgtgggaca tgacccagaa gcgcatcatg tggcacagcc gcatcgccgg cgacccggcc      840
agcgagaccg cgctggcgca ttga                                             864
```

<210> SEQ ID NO 2
<211> LENGTH: 287
<212> TYPE: PRT
<213> ORGANISM: Sphingobium herbicidovorans

<400> SEQUENCE: 2

```
Met Ser Pro Ala Phe Asp Ile Ala Pro Leu Asp Ala Thr Phe Gly Ala
1               5                   10                  15

Val Val Thr Gly Val Lys Leu Ala Asp Leu Asp Asp Ala Gly Trp Leu
            20                  25                  30

Asp Leu Gln Ala Ala Trp Leu Glu Tyr Ala Leu Leu Val Phe Pro Asp
        35                  40                  45

Gln His Leu Thr Arg Glu Gln Gln Ile Ala Phe Ala Arg Arg Phe Gly
    50                  55                  60

Pro Leu Glu Phe Glu Met Ala Ala Ile Ser Asn Val Arg Pro Asp Gly
65                  70                  75                  80

Ser Leu Arg Val Glu Ser Asp Asn Asp Met Met Lys Ile Leu Lys
                85                  90                  95

Gly Asn Met Gly Trp His Ala Asp Ser Thr Tyr Met Pro Val Gln Ala
            100                 105                 110

Lys Gly Ala Val Phe Ser Ala Glu Val Val Pro Ser Val Gly Gly Gln
        115                 120                 125

Thr Gly Phe Ala Asp Met Arg Ala Ala Tyr Asp Ala Leu Asp Glu Asp
    130                 135                 140

Leu Lys Ala Arg Val Glu Thr Leu Gln Ala Arg His Ser Leu His Tyr
145                 150                 155                 160

Ser Gln Ser Lys Leu Gly His Gln Thr Lys Ala Ala Asp Gly Glu Tyr
                165                 170                 175

Ser Gly Tyr Gly Leu His Asp Gly Pro Val Pro Leu Arg Pro Leu Val
            180                 185                 190

Lys Ile His Pro Glu Thr Gly Arg Lys Ser Leu Leu Ile Gly Arg His
        195                 200                 205

Ala His Ala Ile Pro Gly Leu Glu Pro Ala Glu Ser Glu Arg Leu Leu
    210                 215                 220

Gln Gln Leu Ile Asp Phe Ala Cys Gln Pro Arg Ile Tyr His His
225                 230                 235                 240

Asp Trp Ala Pro Gly Asp Ala Val Leu Trp Asp Asn Arg Cys Leu Leu
                245                 250                 255

His Gln Ala Thr Pro Trp Asp Met Thr Gln Lys Arg Ile Met Trp His
            260                 265                 270

Ser Arg Ile Ala Gly Asp Pro Ala Ser Glu Thr Ala Leu Ala His
        275                 280                 285
```

<210> SEQ ID NO 3
<211> LENGTH: 867
<212> TYPE: DNA
<213> ORGANISM: Artificial Sequence
<220> FEATURE:
<223> OTHER INFORMATION: Plant optimized (v1)

<400> SEQUENCE: 3

```
atggcttcac ctgccttcga cattgcccca cttgatgcca catttggggc agttgtcact      60
```

```
ggggtcaagt tggctgatct tgatgacgct ggatggttgg acctccaagc tgcctggctt    120
gaatatgccc tccttgtctt ccctgaccag cacttgacaa gggaacagca aatagctttc    180
gctcgcagat tcggaccact tgagttcgag atggcagcca tctccaatgt tagacccgat    240
ggcagcttga gggttgagtc tgacaatgat gacatgatga agatcctcaa aggcaacatg    300
ggatggcacg ctgacagcac ctacatgcca gtgcaagcaa agggtgcagt gttctcagct    360
gaagtggttc cctctgtggg tggccagact ggttttgctg acatgagagc tgcctatgat    420
gcacttgatg aagacttgaa ggctcgtgtc gagacattgc aagcccgtca ctccctccat    480
tactcccaga gcaagctcgg acaccagacc aaggctgcag atggtgagta ctctggttat    540
ggcctccatg atgggcctgt tccttgaggg ccacttgtga agatccatcc agagactggc    600
agaaaatccc ttctcatagg ccgtcatgcc catgccattc ctggattgga gccagctgag    660
tcagaaaggt tgctccagca actcattgat tttgcttgtc aaccccctag gatctaccac    720
catgactggg ctcctggaga tgcagtgctc tgggacaacc gctgcctcct tcaccaagcc    780
actccctggg acatgaccca gaaacgcatc atgtggcaca gccgcattgc tggtgaccca    840
gcatctgaga ccgcacttgc acattga                                        867
```

<210> SEQ ID NO 4
<211> LENGTH: 288
<212> TYPE: PRT
<213> ORGANISM: Artificial Sequence
<220> FEATURE:
<223> OTHER INFORMATION: Plant optimized (v1)

<400> SEQUENCE: 4

```
Met Ala Ser Pro Ala Phe Asp Ile Ala Pro Leu Asp Ala Thr Phe Gly
1               5                   10                  15

Ala Val Val Thr Gly Val Lys Leu Ala Asp Leu Asp Asp Ala Gly Trp
            20                  25                  30

Leu Asp Leu Gln Ala Ala Trp Leu Glu Tyr Ala Leu Leu Val Phe Pro
        35                  40                  45

Asp Gln His Leu Thr Arg Glu Gln Gln Ile Ala Phe Ala Arg Arg Phe
    50                  55                  60

Gly Pro Leu Glu Phe Glu Met Ala Ala Ile Ser Asn Val Arg Pro Asp
65                  70                  75                  80

Gly Ser Leu Arg Val Glu Ser Asp Asn Asp Met Met Lys Ile Leu
                85                  90                  95

Lys Gly Asn Met Gly Trp His Ala Asp Ser Thr Tyr Met Pro Val Gln
            100                 105                 110

Ala Lys Gly Ala Val Phe Ser Ala Glu Val Val Pro Ser Val Gly Gly
        115                 120                 125

Gln Thr Gly Phe Ala Asp Met Arg Ala Ala Tyr Asp Ala Leu Asp Glu
    130                 135                 140

Asp Leu Lys Ala Arg Val Glu Thr Leu Gln Ala Arg His Ser Leu His
145                 150                 155                 160

Tyr Ser Gln Ser Lys Leu Gly His Gln Thr Lys Ala Ala Asp Gly Glu
                165                 170                 175

Tyr Ser Gly Tyr Gly Leu His Asp Gly Pro Val Pro Leu Arg Pro Leu
            180                 185                 190

Val Lys Ile His Pro Glu Thr Gly Arg Lys Ser Leu Leu Ile Gly Arg
        195                 200                 205

His Ala His Ala Ile Pro Gly Leu Glu Pro Ala Glu Ser Glu Arg Leu
```

Leu Gln Gln Leu Ile Asp Phe Ala Cys Gln Pro Pro Arg Ile Tyr His
225                 230                 235                 240

His Asp Trp Ala Pro Gly Asp Ala Val Leu Trp Asp Asn Arg Cys Leu
            245                 250                 255

Leu His Gln Ala Thr Pro Trp Asp Met Thr Gln Lys Arg Ile Met Trp
        260                 265                 270

His Ser Arg Ile Ala Gly Asp Pro Ala Ser Glu Thr Ala Leu Ala His
    275                 280                 285

<210> SEQ ID NO 5
<211> LENGTH: 867
<212> TYPE: DNA
<213> ORGANISM: Artificial Sequence
<220> FEATURE:
<223> OTHER INFORMATION: E. coli optimized (v2)

<400> SEQUENCE: 5
atggcgagcc cggcgttcga cattgcgcca ctgatgctac cctttggcgc agttgtaact    60
ggcgtaaaac tggcggatct ggatgacgct ggctggctgg acctgcaggc tgcgtggctg   120
gaatatgcac tgctggtatt cccggaccag cacctgaccc gtgaacagca gatcgctttc   180
gcacgccgct ccggtccact ggagttcgaa atggcagcga tctccaacgt tcgtccggat   240
ggcagcctgc gtgttgaatc tgacaacgat gacatgatga aaatcctgaa aggcaacatg   300
ggttggcacg ctgactctac ctacatgcca gttcaggcaa agggtgcagt gttcagcgct   360
gaagtggttc gtctgtgggt ggccagact ggttttgcgg acatgcgcgc tgcttatgat   420
gcactggatg aagacctgaa agctcgtgtt gaaaccctgc aagcgcgtca ctccctgcat   480
tactcccagt ccaagctggg tcaccagacc aaagctgcgg atggtgagta ctctggttac   540
ggcctgcatg atggtccggt tccgctgcgt ccgctggtga aaatccatcc ggaaactggc   600
cgcaaatccc tgctgatcgg ccgtcatgcg cacgcgattc cgggcctgga accggctgag   660
tctgaacgtc tgctgcaaca gctgattgat tttgcttgtc agccgccgcg tatctaccac   720
cacgactggg cgccgggtga tgcagtgctg tgggacaacc gctgcctgct caccaagcg   780 actccgtggg acatgaccca gaaacgcatc atgtggcaca gccgcattgc gggtgacccg   840
gcatctgaga ccgcactggc acactaa                                       867

<210> SEQ ID NO 6
<211> LENGTH: 22
<212> TYPE: PRT
<213> ORGANISM: Artificial Sequence
<220> FEATURE:
<223> OTHER INFORMATION: AAD-13 PTU primer

<400> SEQUENCE: 6

Ala Thr Gly Gly Cys Thr Cys Ala Thr Gly Cys Thr Gly Cys Cys Cys
1               5                   10                  15

Thr Cys Ala Gly Cys Cys
            20

<210> SEQ ID NO 7
<211> LENGTH: 22
<212> TYPE: DNA
<213> ORGANISM: Artificial Sequence
<220> FEATURE:
<223> OTHER INFORMATION: AAD-13 PTU primer

<400> SEQUENCE: 7

```
cgggcaggcc taactccacc aa                                              22

<210> SEQ ID NO 8
<211> LENGTH: 31
<212> TYPE: DNA
<213> ORGANISM: Artificial Sequence
<220> FEATURE:
<223> OTHER INFORMATION: suc-Nde forward primer

<400> SEQUENCE: 8
catatgaact tacatgaata tcaggcaaaa c                                    31

<210> SEQ ID NO 9
<211> LENGTH: 30
<212> TYPE: DNA
<213> ORGANISM: Artificial Sequence
<220> FEATURE:
<223> OTHER INFORMATION: suc-Xho reverse primer

<400> SEQUENCE: 9
ctcgagtttc agaacagttt tcagtgcttc                                      30

<210> SEQ ID NO 10
<211> LENGTH: 18
<212> TYPE: DNA
<213> ORGANISM: Artificial Sequence
<220> FEATURE:
<223> OTHER INFORMATION: aad-13 forward primer

<400> SEQUENCE: 10
catatggcga gcccggcg                                                   18

<210> SEQ ID NO 11
<211> LENGTH: 24
<212> TYPE: DNA
<213> ORGANISM: Artificial Sequence
<220> FEATURE:
<223> OTHER INFORMATION: aad-13 reverse primer

<400> SEQUENCE: 11
ctcgaggtgt gccagtgcgg tctc                                            24

<210> SEQ ID NO 12
<211> LENGTH: 292
<212> TYPE: PRT
<213> ORGANISM: Delftia acidovorans

<400> SEQUENCE: 12
```

Met Gln Thr Thr Leu Gln Ile Thr Pro Thr Gly Ala Thr Leu Gly Ala
 1               5                  10                  15

Thr Val Thr Gly Val His Leu Ala Thr Leu Asp Asp Ala Gly Phe Ala
             20                  25                  30

Ala Leu His Ala Ala Trp Leu Gln His Ala Leu Leu Ile Phe Pro Gly
         35                  40                  45

Gln His Leu Ser Asn Asp Gln Gln Ile Thr Phe Ala Lys Arg Phe Gly
     50                  55                  60

Ala Ile Glu Arg Ile Gly Gly Gly Asp Ile Val Ala Ile Ser Asn Val
 65                  70                  75                  80

Lys Ala Asp Gly Thr Val Arg Gln His Ser Pro Ala Glu Trp Asp Asp
                 85                  90                  95

Met Met Lys Val Ile Val Gly Asn Met Ala Trp His Ala Asp Ser Thr
            100                 105                 110

```
Tyr Met Pro Val Met Ala Gln Gly Ala Val Phe Ser Ala Glu Val Val
            115                 120                 125

Pro Ala Val Gly Gly Arg Thr Cys Phe Ala Asp Met Arg Ala Ala Tyr
130                 135                 140

Asp Ala Leu Asp Glu Ala Thr Arg Ala Leu Val His Gln Arg Ser Ala
145                 150                 155                 160

Arg His Ser Leu Val Tyr Ser Gln Ser Lys Leu Gly His Val Gln Gln
                165                 170                 175

Ala Gly Ser Ala Tyr Ile Gly Tyr Gly Met Asp Thr Thr Ala Thr Pro
            180                 185                 190

Leu Arg Pro Leu Val Lys Val His Pro Glu Thr Gly Arg Pro Ser Leu
            195                 200                 205

Leu Ile Gly Arg His Ala His Ala Ile Pro Gly Met Asp Ala Ala Glu
210                 215                 220

Ser Glu Arg Phe Leu Glu Gly Leu Val Asp Trp Ala Cys Gln Ala Pro
225                 230                 235                 240

Arg Val His Ala His Gln Trp Ala Ala Gly Asp Val Val Trp Asp
                245                 250                 255

Asn Arg Cys Leu Leu His Arg Ala Glu Pro Trp Asp Phe Lys Leu Pro
            260                 265                 270

Arg Val Met Trp His Ser Arg Leu Ala Gly Arg Pro Glu Thr Glu Gly
            275                 280                 285

Ala Ala Leu Val
            290

<210> SEQ ID NO 13
<211> LENGTH: 295
<212> TYPE: PRT
<213> ORGANISM: Sphingobium herbicidovorans

<400> SEQUENCE: 13

Met His Ala Ala Leu Ser Pro Leu Ser Gln Arg Phe Glu Arg Ile Ala
1               5                   10                  15

Val Gln Pro Leu Thr Gly Val Leu Gly Ala Glu Ile Thr Gly Val Asp
            20                  25                  30

Leu Arg Glu Pro Leu Asp Asp Ser Thr Trp Asn Glu Ile Leu Asp Ala
            35                  40                  45

Phe His Thr Tyr Gln Val Ile Tyr Phe Pro Gly Gln Ala Ile Thr Asn
        50                  55                  60

Glu Gln His Ile Ala Phe Ser Arg Arg Phe Gly Pro Val Asp Pro Val
65                  70                  75                  80

Pro Leu Leu Lys Ser Ile Glu Gly Tyr Pro Glu Val Gln Met Ile Arg
                85                  90                  95

Arg Glu Ala Asn Glu Ser Gly Arg Val Ile Gly Asp Asp Trp His Thr
            100                 105                 110

Asp Ser Thr Phe Leu Asp Ala Pro Pro Ala Ala Val Val Met Arg Ala
            115                 120                 125

Ile Asp Val Pro Glu His Gly Gly Asp Thr Gly Phe Leu Ser Met Tyr
130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
```

```
                    180                 185                 190
Asp Ala Gly Asp Arg Glu Thr Val His Pro Leu Val Val Thr His Pro
            195                 200                 205
Gly Ser Gly Arg Lys Gly Leu Tyr Val Asn Gln Val Tyr Cys Gln Arg
        210                 215                 220
Ile Glu Gly Met Thr Asp Ala Glu Ser Lys Pro Leu Leu Gln Phe Leu
225                 230                 235                 240
Tyr Glu His Ala Thr Arg Phe Asp Phe Thr Cys Arg Val Arg Trp Lys
                245                 250                 255
Lys Asp Gln Val Leu Val Trp Asp Asn Leu Cys Thr Met His Arg Ala
            260                 265                 270
Val Pro Asp Tyr Ala Gly Lys Phe Arg Tyr Leu Thr Arg Thr Thr Val
        275                 280                 285
Gly Gly Val Arg Pro Ala Arg
        290                 295

<210> SEQ ID NO 14
<211> LENGTH: 295
<212> TYPE: PRT
<213> ORGANISM: Bradyrhizobium japonicum USDA 110

<400> SEQUENCE: 14

Met Thr Ile Ala Ile Arg Gln Leu Gln Thr His Phe Val Gly Gln Val
1               5                   10                  15
Ser Gly Leu Asp Leu Arg Lys Pro Leu Thr Pro Gly Glu Ala Arg Glu
            20                  25                  30
Val Glu Ser Ala Met Asp Lys Tyr Ala Val Leu Val Phe His Asp Gln
        35                  40                  45
Asp Ile Thr Asp Glu Gln Gln Met Ala Phe Ala Leu Asn Phe Gly Gln
    50                  55                  60
Arg Glu Asp Ala Arg Gly Gly Thr Val Thr Lys Glu Lys Asp Tyr Arg
65                  70                  75                  80
Leu Gln Ser Gly Leu Asn Asp Val Ser Asn Leu Gly Lys Asp Gly Lys
                85                  90                  95
Pro Leu Ala Lys Asp Ser Arg Thr His Leu Phe Asn Leu Gly Asn Cys
            100                 105                 110
Leu Trp His Ser Asp Ser Ser Phe Arg Pro Ile Pro Ala Lys Phe Ser
        115                 120                 125
Leu Leu Ser Ala Arg Val Val Asn Pro Thr Gly Gly Asn Thr Glu Phe
    130                 135                 140
Ala Asp Met Arg Ala Ala Tyr Asp Ala Leu Asp Asp Glu Thr Lys Ala
145                 150                 155                 160
Glu Ile Glu Asp Leu Val Cys Glu His Ser Leu Met Tyr Ser Arg Gly
                165                 170                 175
Ser Leu Gly Phe Thr Glu Tyr Thr Asp Glu Glu Lys Gln Met Phe Lys
            180                 185                 190
Pro Val Leu Gln Arg Leu Val Arg Thr His Pro Val His Arg Arg Lys
        195                 200                 205
Ser Leu Tyr Leu Ser Ser His Ala Gly Lys Ile Ala Ser Met Ser Val
    210                 215                 220
Pro Glu Gly Arg Leu Leu Leu Arg Asp Leu Asn Glu His Ala Thr Gln
225                 230                 235                 240
Pro Glu Phe Val Tyr Val His Lys Trp Lys Leu His Asp Leu Val Met
                245                 250                 255
```

Trp Asp Asn Arg Gln Thr Met His Arg Val Arg Arg Tyr Asp Gln Ser
            260                 265                 270

Gln Pro Arg Asp Met Arg Arg Ala Thr Val Ala Gly Thr Glu Pro Thr
        275                 280                 285

Val Gln Gln Gln Ala Ala Glu
    290                 295

<210> SEQ ID NO 15
<211> LENGTH: 287
<212> TYPE: PRT
<213> ORGANISM: Cupriavidus Necator

<400> SEQUENCE: 15

Met Ser Val Val Ala Asn Pro Leu His Pro Leu Phe Ala Ala Gly Val
1               5                   10                  15

Glu Asp Ile Asp Leu Arg Glu Ala Leu Gly Ser Thr Glu Val Arg Glu
            20                  25                  30

Ile Glu Arg Leu Met Asp Glu Lys Ser Val Leu Val Phe Arg Gly Gln
        35                  40                  45

Pro Leu Ser Gln Asp Gln Gln Ile Ala Phe Ala Arg Asn Phe Gly Pro
    50                  55                  60

Leu Glu Gly Gly Phe Ile Lys Val Asn Gln Arg Pro Ser Arg Phe Lys
65                  70                  75                  80

Tyr Ala Glu Leu Ala Asp Ile Ser Asn Val Ser Leu Asp Gly Lys Val
                85                  90                  95

Ala Gln Arg Asp Ala Arg Glu Val Val Gly Asn Phe Ala Asn Gln Leu
            100                 105                 110

Trp His Ser Asp Ser Ser Phe Gln Gln Pro Ala Ala Arg Tyr Ser Met
        115                 120                 125

Leu Ser Ala Val Val Pro Pro Ser Gly Gly Asp Thr Glu Phe Cys
    130                 135                 140

Asp Met Arg Ala Ala Tyr Asp Ala Leu Pro Arg Asp Leu Gln Ser Glu
145                 150                 155                 160

Leu Glu Gly Leu Arg Ala Glu His Tyr Ala Leu Asn Ser Arg Phe Leu
                165                 170                 175

Leu Gly Asp Thr Asp Tyr Ser Glu Ala Gln Arg Asn Ala Met Pro Pro
            180                 185                 190

Val Asn Trp Pro Leu Val Arg Thr His Ala Gly Ser Gly Arg Lys Phe
        195                 200                 205

Leu Phe Ile Gly Ala His Ala Ser His Val Glu Gly Leu Pro Val Ala
    210                 215                 220

Glu Gly Arg Met Leu Leu Ala Glu Leu Leu Glu His Ala Thr Gln Arg
225                 230                 235                 240

Glu Phe Val Tyr Arg His Arg Trp Asn Val Gly Asp Leu Val Met Trp
                245                 250                 255

Asp Asn Arg Cys Val Leu His Arg Gly Arg Arg Tyr Asp Ile Ser Ala
            260                 265                 270

Arg Arg Glu Leu Arg Arg Ala Thr Thr Leu Asp Asp Ala Val Val
        275                 280                 285

<210> SEQ ID NO 16
<211> LENGTH: 283
<212> TYPE: PRT
<213> ORGANISM: Escherichia coli

<400> SEQUENCE: 16

-continued

```
Met Ser Glu Arg Leu Ser Ile Thr Pro Leu Gly Pro Tyr Ile Gly Ala
1               5                   10                  15

Gln Ile Ser Gly Ala Asp Leu Thr Arg Pro Leu Ser Asn Gln Phe
            20                  25              30

Glu Gln Leu Tyr His Ala Val Leu Arg His Gln Val Val Phe Leu Arg
        35              40              45

Asp Gln Ala Ile Thr Pro Gln Gln Arg Ala Leu Ala Gln Arg Phe
    50              55              60

Gly Glu Leu His Ile His Pro Val Tyr Pro His Ala Glu Gly Val Asp
65              70              75              80

Glu Ile Ile Val Leu Asp Thr His Asn Asp Asn Pro Pro Asp Asn Asp
                85              90              95

Asn Trp His Thr Asp Val Thr Phe Ile Glu Thr Pro Pro Ala Gly Ala
            100             105             110

Ile Leu Ala Ala Lys Glu Leu Pro Ser Thr Gly Gly Asp Thr Leu Trp
        115             120             125

Thr Ser Gly Ile Ala Ala Tyr Glu Ala Leu Ser Val Pro Phe Arg Gln
    130             135             140

Leu Leu Ser Gly Leu Arg Ala Glu His Asp Phe Arg Lys Ser Phe Pro
145             150             155             160

Glu Tyr Lys Tyr Arg Lys Thr Glu Glu Glu His Gln Arg Trp Arg Glu
                165             170             175

Ala Val Ala Lys Asn Pro Pro Leu Leu His Pro Val Val Arg Thr His
            180             185             190

Pro Val Ser Gly Lys Gln Ala Leu Phe Val Asn Glu Gly Phe Thr Thr
            195             200             205

Arg Ile Val Asp Val Ser Glu Lys Glu Ser Glu Ala Leu Leu Ser Phe
210             215             220

Leu Phe Ala His Ile Thr Lys Pro Glu Phe Gln Val Arg Trp Arg Trp
225             230             235             240

Gln Pro Asn Asp Ile Ala Ile Trp Asp Asn Arg Val Thr Gln His Tyr
            245             250             255

Ala Asn Ala Asp Tyr Leu Pro Gln Arg Arg Ile Met His Arg Ala Thr
            260             265             270

Ile Leu Gly Asp Lys Pro Phe Tyr Arg Ala Gly
        275             280
```